United States Patent
Bishop et al.

(10) Patent No.: US 8,562,559 B2
(45) Date of Patent: Oct. 22, 2013

(54) EXPANDABLE ILIAC SHEATH AND METHOD OF USE

(75) Inventors: Joseph Bishop, Irvine, CA (US); Jay Lenker, Laguna Beach, CA (US); Edward J. Nance, Corona, CA (US)

(73) Assignee: Onset Medical Corporation, Irvine, CA (US)

( * ) Notice: Subject to any disclaimer, the term of this patent is extended or adjusted under 35 U.S.C. 154(b) by 199 days.

(21) Appl. No.: 12/945,801

(22) Filed: Nov. 12, 2010

(65) Prior Publication Data

US 2011/0152763 A1 Jun. 23, 2011

Related U.S. Application Data

(63) Continuation-in-part of application No. PCT/US2009/044031, filed on May 14, 2009, which is a continuation-in-part of application No. 12/258,233, filed on Oct. 24, 2008.

(60) Provisional application No. 61/326,567, filed on Apr. 21, 2010, provisional application No. 61/127,619, filed on May 14, 2008.

(51) Int. Cl.
*A61M 31/00* (2006.01)
*A61M 37/00* (2006.01)
*A61M 5/178* (2006.01)

(52) U.S. Cl.
USPC .................. 604/103.06; 604/164.1; 604/509

(58) Field of Classification Search
USPC .................. 604/509, 101.01, 103.01–103.14, 604/96.01, 99.04, 264, 274, 270
See application file for complete search history.

(56) References Cited

U.S. PATENT DOCUMENTS

| 4,338,942 A | 7/1982 | Fogarty |
| 4,401,433 A | 8/1983 | Luther |

(Continued)

FOREIGN PATENT DOCUMENTS

| EP | 0206553 | 1/1991 |
| WO | WO/99/17665 | 4/1999 |

(Continued)

OTHER PUBLICATIONS

Sep. 15, 2011 Extended Search Report for Application No. 09747627.9 filed on May 14, 2009 (European Counterpart of the present application).

(Continued)

*Primary Examiner* — Nicholas Lucchesi
*Assistant Examiner* — Rebecca E Eisenberg
(74) *Attorney, Agent, or Firm* — Knobbe, Martens, Olson & Bear LLP

(57) ABSTRACT

Disclosed is an expandable transluminal sheath, for introduction into the body while in a first, collapsed cross-sectional configuration, subsequent expansion of at least a part of the distal end of the sheath to a second, enlarged cross-sectional configuration, and subsequent removal in a third, collapsed cross-sectional configuration. The sheath is configured for use in the vascular system and has utility in the introduction and removal of implant delivery catheters. The access route is through the femoral arteries and the iliac arteries into the aorta. The distal end of the sheath is maintained in the first, collapsed cross-sectional configuration during advancement to the arteries into the aorta. The distal end of the sheath is then expanded using a radial dilatation device, which is removed prior to the introduction of implant delivery catheters. The distal end of the sheath is subsequently reduced to a diametrically small size for removal.

19 Claims, 30 Drawing Sheets

(56) References Cited

U.S. PATENT DOCUMENTS

| | | | |
|---|---|---|---|
| 4,738,666 A | 4/1988 | Fuqua | |
| 4,753,221 A | 6/1988 | Kensey et al. | |
| 4,919,647 A | 4/1990 | Nash | |
| 5,053,007 A * | 10/1991 | Euteneuer | 604/103.11 |
| 5,059,183 A | 10/1991 | Semrad | |
| 5,092,839 A | 3/1992 | Kipperman | |
| 5,201,901 A | 4/1993 | Harada et al. | |
| 5,250,025 A | 10/1993 | Sosnowski et al. | |
| 5,263,964 A | 11/1993 | Purdy | |
| 5,295,994 A | 3/1994 | Bonutti | |
| 5,320,611 A | 6/1994 | Bonutti | |
| 5,358,495 A | 10/1994 | Lynn | |
| 5,395,349 A | 3/1995 | Quiachon et al. | |
| 5,458,574 A | 10/1995 | Machold et al. | |
| 5,514,091 A | 5/1996 | Yoon | |
| 5,527,336 A | 6/1996 | Rosenbluth | |
| 5,662,614 A | 9/1997 | Edoga | |
| 5,669,936 A | 9/1997 | Lazarus | |
| 5,766,151 A | 6/1998 | Valley et al. | |
| 5,766,203 A | 6/1998 | Imran et al. | |
| 5,772,631 A | 6/1998 | Lepor | |
| 5,776,141 A | 7/1998 | Klein et al. | |
| 5,807,311 A | 9/1998 | Palestrant | |
| 5,814,016 A | 9/1998 | Valley et al. | |
| 5,824,002 A * | 10/1998 | Gentelia et al. | 604/164.11 |
| 5,868,702 A | 2/1999 | Stevens et al. | |
| 5,885,238 A | 3/1999 | Stevens et al. | |
| 5,908,448 A | 6/1999 | Roberts et al. | |
| 5,911,702 A | 6/1999 | Romley et al. | |
| 5,928,181 A | 7/1999 | Coleman et al. | |
| 6,090,096 A | 7/2000 | St. Goar et al. | |
| 6,129,707 A | 10/2000 | Cryer | |
| 6,139,517 A | 10/2000 | Macoviak et al. | |
| 6,149,578 A | 11/2000 | Downey et al. | |
| 6,152,141 A | 11/2000 | Stevens et al. | |
| 6,156,053 A | 12/2000 | Gandhi et al. | |
| 6,168,579 B1 | 1/2001 | Tsugita | |
| 6,183,443 B1 | 2/2001 | Kratoska et al. | |
| 6,197,016 B1 | 3/2001 | Fourkas et al. | |
| 6,231,498 B1 | 5/2001 | Pfeiffer et al. | |
| 6,231,551 B1 | 5/2001 | Barbut | |
| 6,234,995 B1 | 5/2001 | Peacock, III | |
| 6,254,563 B1 | 7/2001 | Macoviak et al. | |
| 6,264,633 B1 | 7/2001 | Knorig | |
| 6,299,628 B1 * | 10/2001 | Harrison et al. | 606/194 |
| 6,312,443 B1 | 11/2001 | Stone | |
| 6,338,725 B1 | 1/2002 | Hermann et al. | |
| 6,346,092 B1 | 2/2002 | Leschinsky | |
| 6,358,238 B1 | 3/2002 | Sherry | |
| 6,368,345 B1 | 4/2002 | Dehdashtian et al. | |
| 6,375,675 B2 | 4/2002 | Dehdashtian et al. | |
| 6,451,053 B1 | 9/2002 | Dehdashtian et al. | |
| 6,530,894 B1 | 3/2003 | Barbut | |
| 6,537,247 B2 | 3/2003 | Shannon | |
| 6,547,760 B1 | 4/2003 | Samson et al. | |
| 6,565,552 B1 | 5/2003 | Barbut | |
| 6,576,007 B2 | 6/2003 | Dehdashtian et al. | |
| 6,579,259 B2 | 6/2003 | Stevens et al. | |
| 6,582,388 B1 | 6/2003 | Kadan et al. | |
| 6,592,557 B2 | 7/2003 | Barbut | |
| 6,616,678 B2 | 9/2003 | Nishtala et al. | |
| 6,626,899 B2 | 9/2003 | Houser et al. | |
| 6,635,046 B1 | 10/2003 | Barbut | |
| 6,638,268 B2 | 10/2003 | Niazi | |
| 6,669,687 B1 | 12/2003 | Saadat | |
| 6,679,871 B2 * | 1/2004 | Hahnen | 604/509 |
| 6,692,512 B2 | 2/2004 | Jang | |
| 6,695,810 B2 | 2/2004 | Peacock, III et al. | |
| 6,695,811 B2 | 2/2004 | Samson et al. | |
| 6,695,864 B2 | 2/2004 | Macoviak et al. | |
| 6,706,013 B1 | 3/2004 | Bhat et al. | |
| 6,706,017 B1 | 3/2004 | Dulguerov | |
| 6,712,806 B2 | 3/2004 | St. Germain et al. | |
| 6,726,651 B1 | 4/2004 | Robinson et al. | |
| 6,743,196 B2 | 6/2004 | Barbut et al. | |
| 6,746,431 B2 | 6/2004 | Pfeiffer et al. | |
| 6,767,345 B2 | 7/2004 | St. Germain et al. | |
| 6,793,647 B1 | 9/2004 | Cryer | |
| 6,796,992 B2 | 9/2004 | Barbut | |
| 6,848,448 B1 | 2/2005 | St. Germain et al. | |
| 6,866,647 B2 | 3/2005 | Barbut | |
| 6,866,650 B2 | 3/2005 | Stevens et al. | |
| 6,872,223 B2 | 3/2005 | Roberts et al. | |
| 6,913,600 B2 | 7/2005 | Valley et al. | |
| 6,932,792 B1 | 8/2005 | St. Goar et al. | |
| 7,150,736 B2 | 12/2006 | Barbut et al. | |
| 7,229,403 B2 | 6/2007 | Schock et al. | |
| 7,635,386 B1 | 12/2009 | Gammie | |
| 7,699,864 B2 | 4/2010 | Kick et al. | |
| 7,713,193 B2 | 5/2010 | Nance et al. | |
| 7,722,568 B2 | 5/2010 | Lenker et al. | |
| 7,780,692 B2 | 8/2010 | Nance et al. | |
| 7,892,203 B2 | 2/2011 | Lenker et al. | |
| 7,951,110 B2 | 5/2011 | Bishop et al. | |
| 2001/0012950 A1 | 8/2001 | Nishtala et al. | |
| 2002/0009535 A1 | 1/2002 | Michal et al. | |
| 2002/0077653 A1 | 6/2002 | Hudson et al. | |
| 2002/0099431 A1 | 7/2002 | Armstrong et al. | |
| 2003/0114913 A1 | 6/2003 | Spenser et al. | |
| 2004/0006344 A1 | 1/2004 | Nguyen et al. | |
| 2005/0049667 A1 | 3/2005 | Arbefeuille et al. | |
| 2005/0085842 A1 | 4/2005 | Eversull et al. | |
| 2005/0124937 A1 | 6/2005 | Kick et al. | |
| 2005/0149105 A1 | 7/2005 | Leeflang et al. | |
| 2005/0154442 A1 | 7/2005 | Eidenschink et al. | |
| 2005/0222576 A1 | 10/2005 | Kick et al. | |
| 2005/0251094 A1 | 11/2005 | Peterson | |
| 2006/0074476 A1 | 4/2006 | Holman et al. | |
| 2006/0074484 A1 | 4/2006 | Huber | |
| 2006/0135962 A1 * | 6/2006 | Kick et al. | 606/108 |
| 2006/0135981 A1 | 6/2006 | Lenker et al. | |
| 2007/0060880 A1 | 3/2007 | Gregorich et al. | |
| 2007/0135793 A1 | 6/2007 | Barbut et al. | |
| 2008/0082079 A1 | 4/2008 | Braga et al. | |
| 2008/0109065 A1 | 5/2008 | Bowe | |
| 2008/0177142 A1 | 7/2008 | Roskopf | |
| 2008/0183136 A1 | 7/2008 | Lenker et al. | |
| 2009/0287182 A1 | 11/2009 | Bishop et al. | |
| 2009/0287183 A1 | 11/2009 | Bishop et al. | |
| 2010/0228077 A1 | 9/2010 | Lenker et al. | |
| 2011/0144690 A1 | 6/2011 | Bishop et al. | |

FOREIGN PATENT DOCUMENTS

| | | |
|---|---|---|
| WO | WO/03/090834 | 11/2003 |
| WO | WO 2006/029370 | 3/2006 |

OTHER PUBLICATIONS

Dec. 28, 2011 International Search Report and Written Opinion of PCT Application No. PCT/US2011/032995 filed on Apr. 19, 2011.

International Search Report for Application No. PCT/US2009/044031, the PCT counterpart of the present application, mailed Dec. 22, 2009.

* cited by examiner

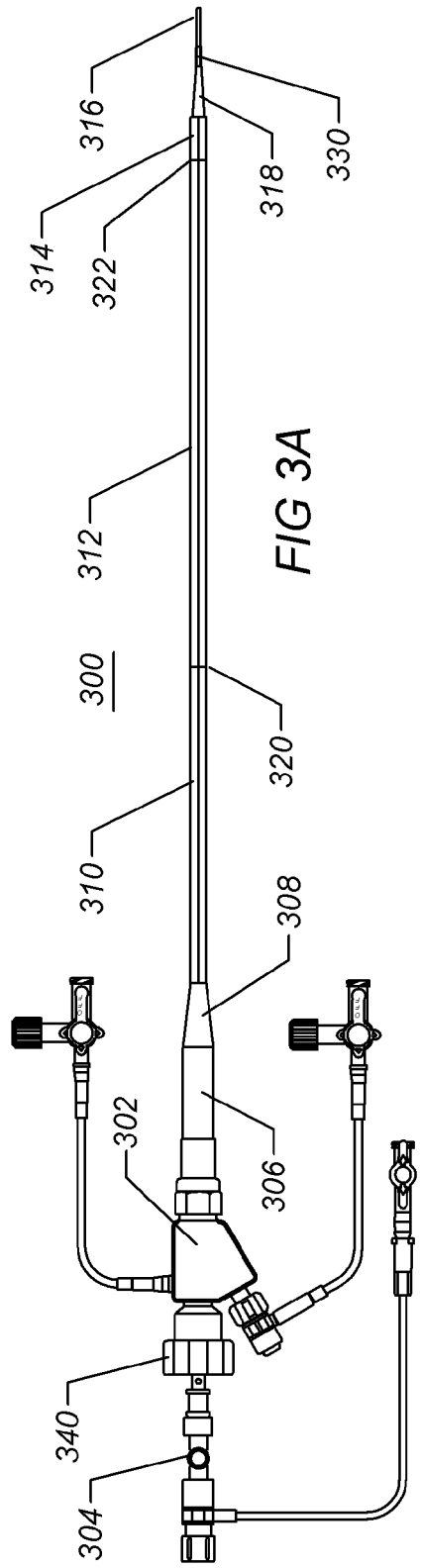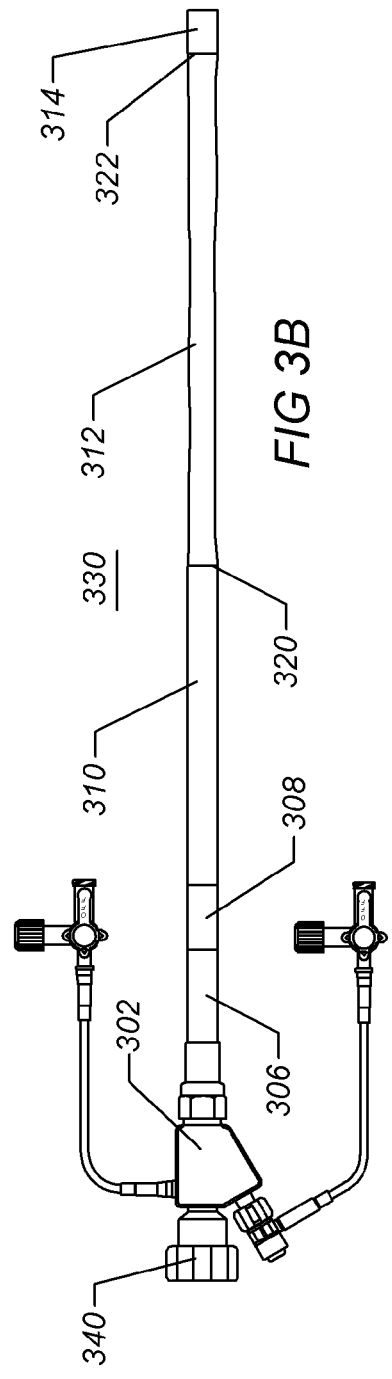

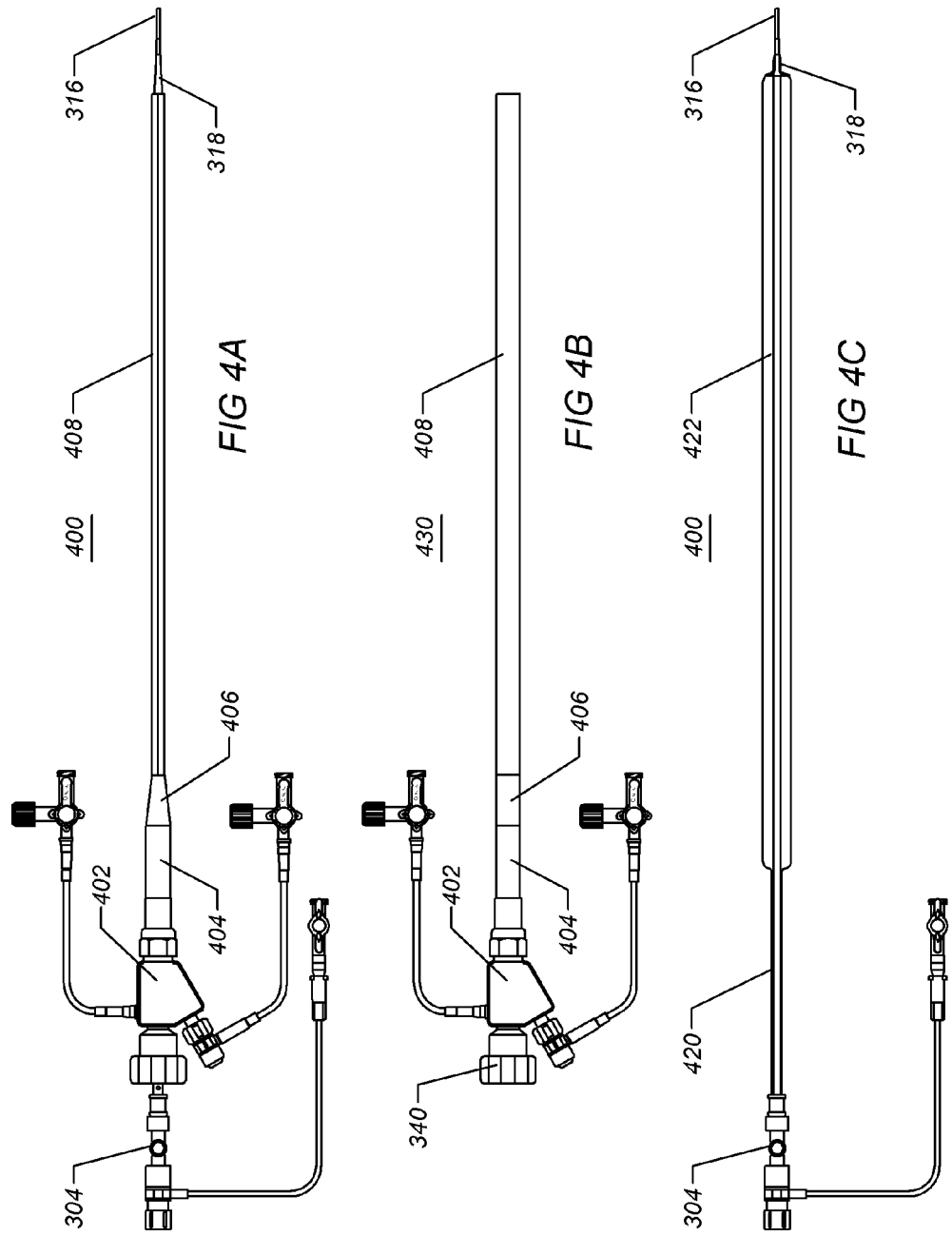

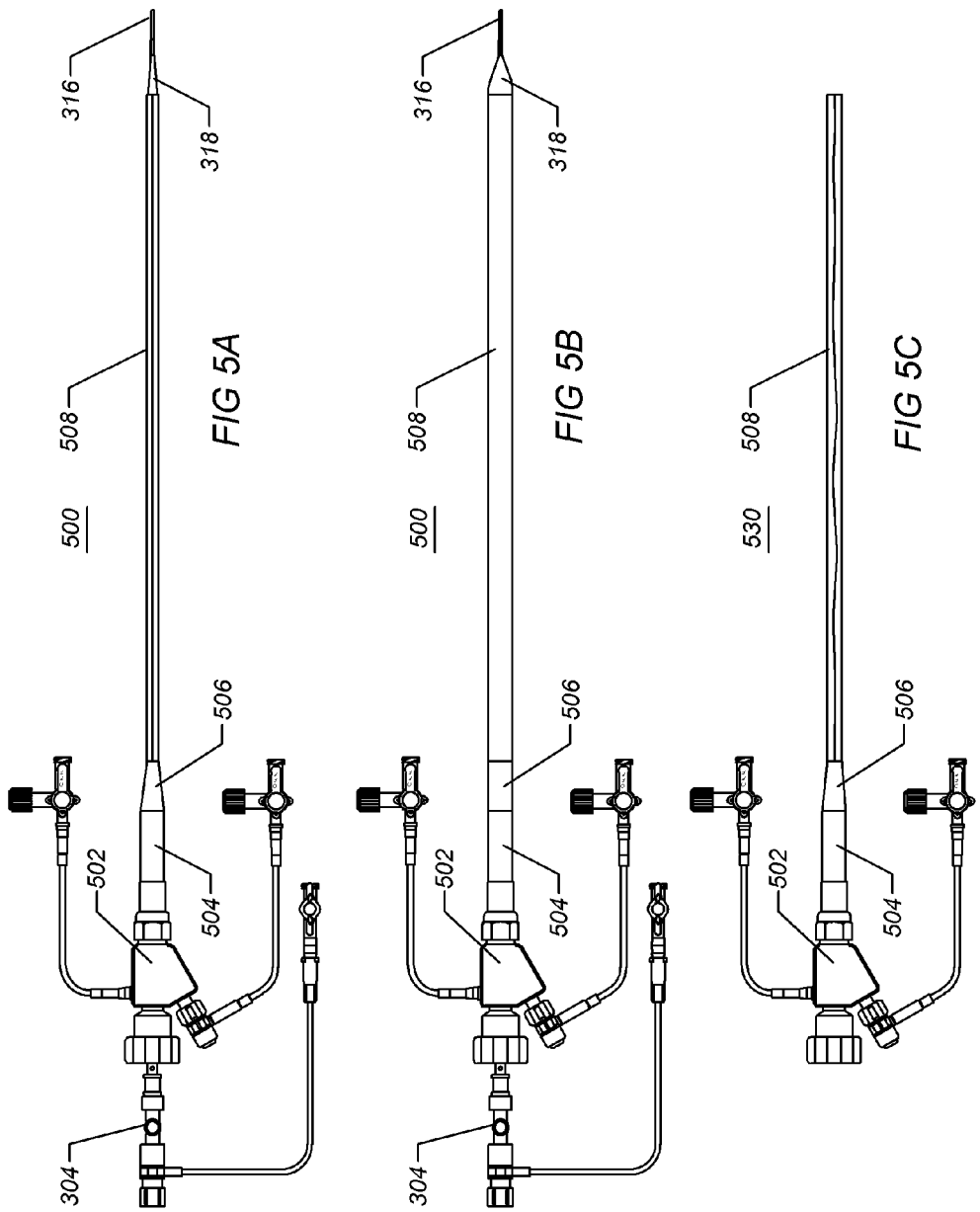

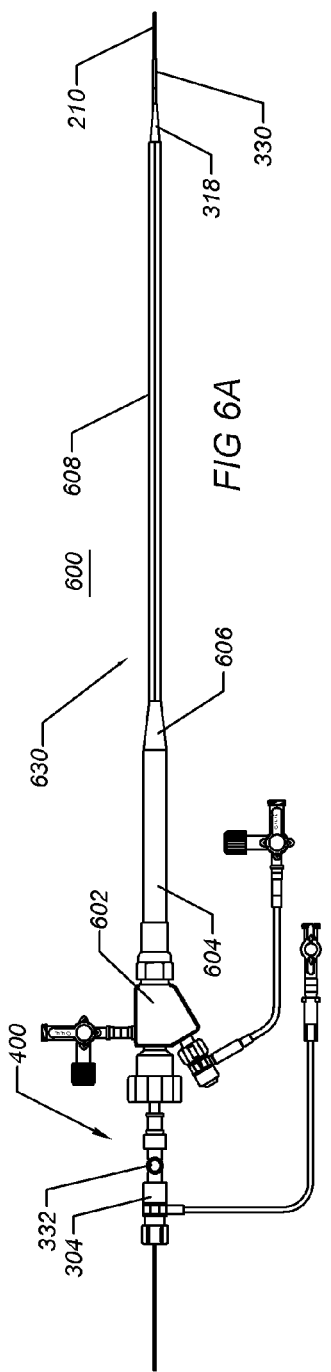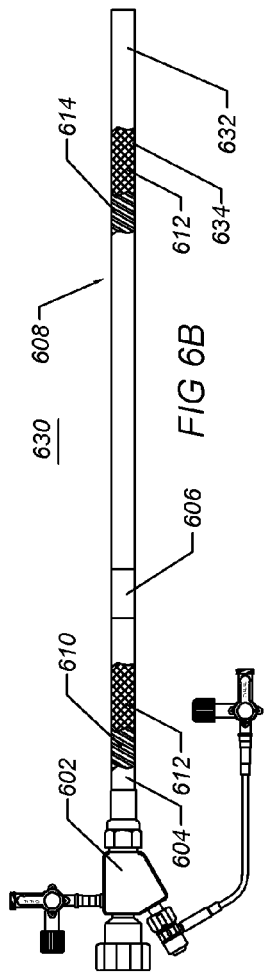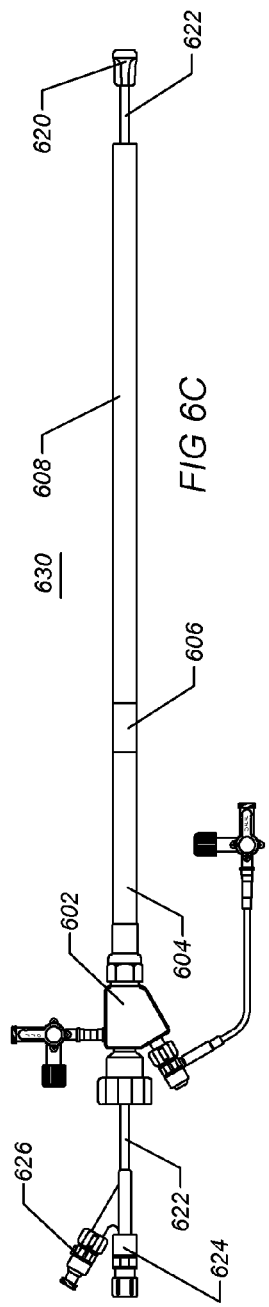

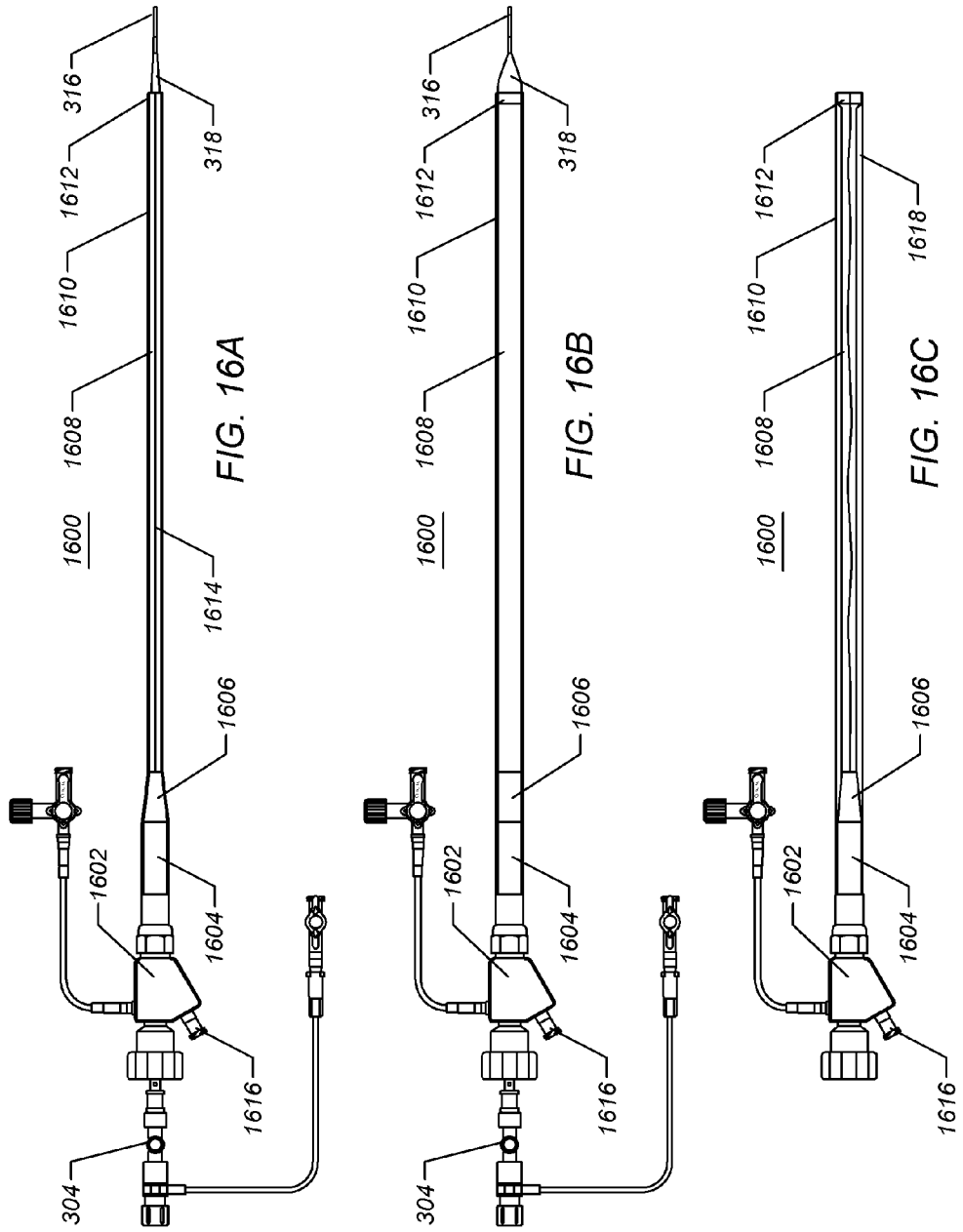

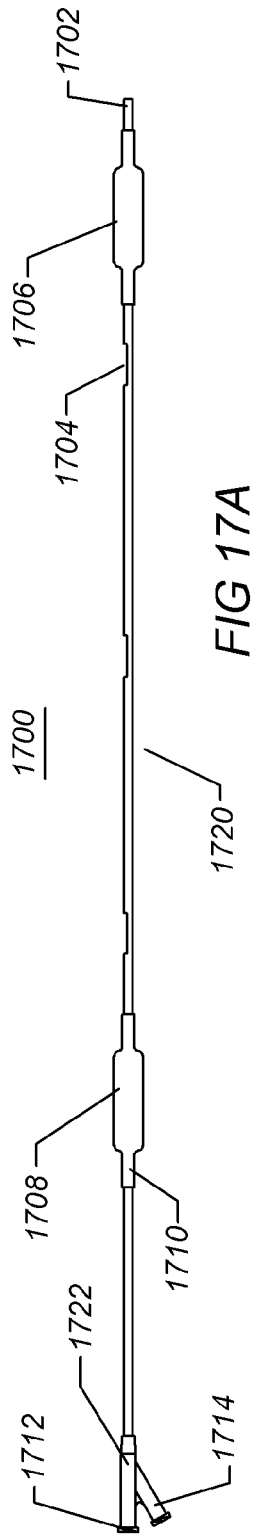
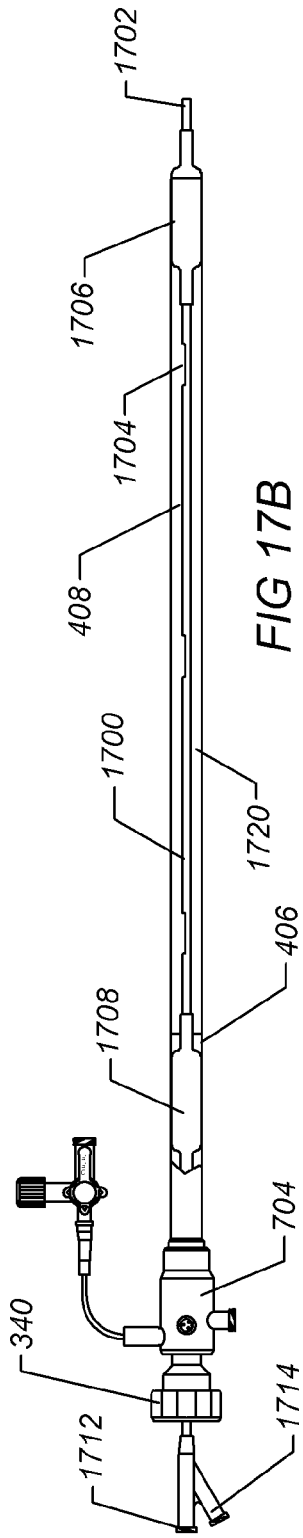
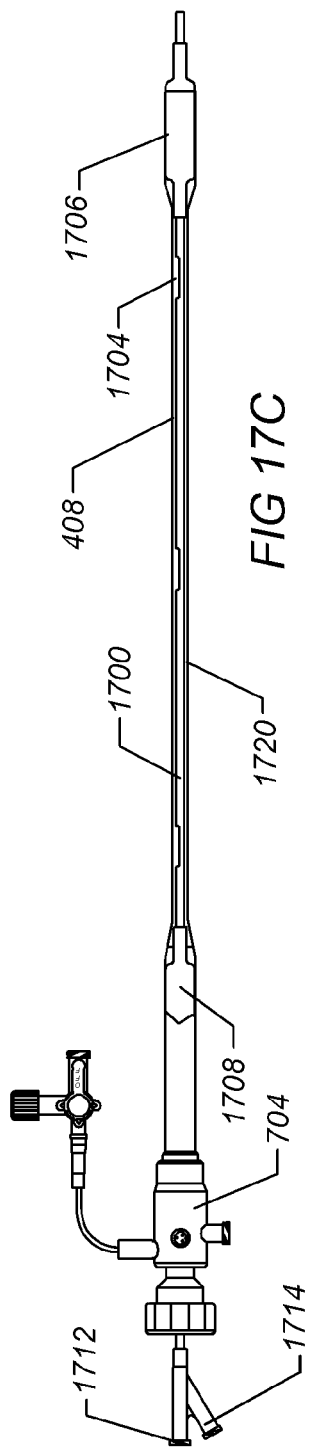
FIG 17A
FIG 17B
FIG 17C

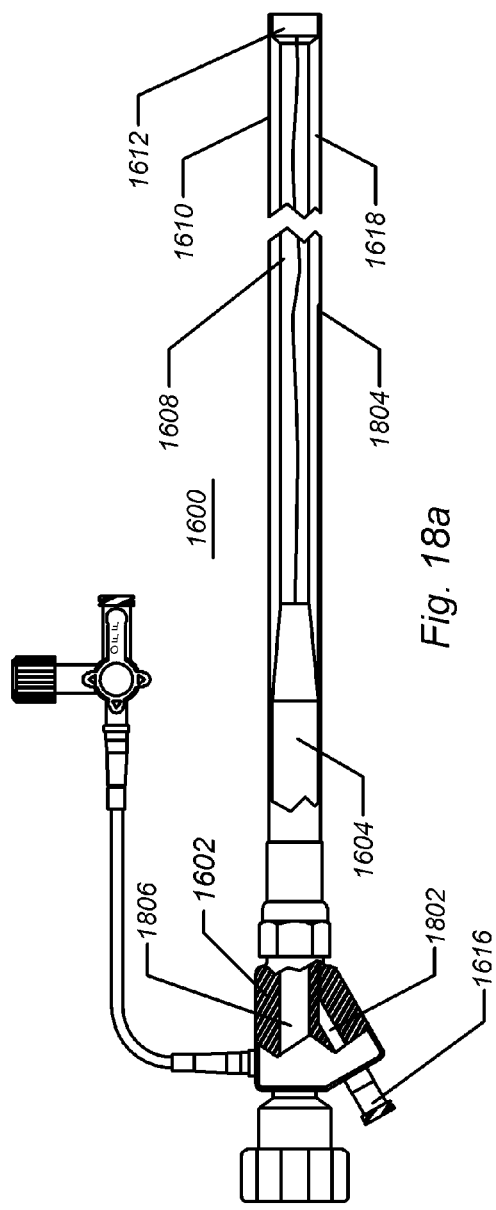
Fig. 18a
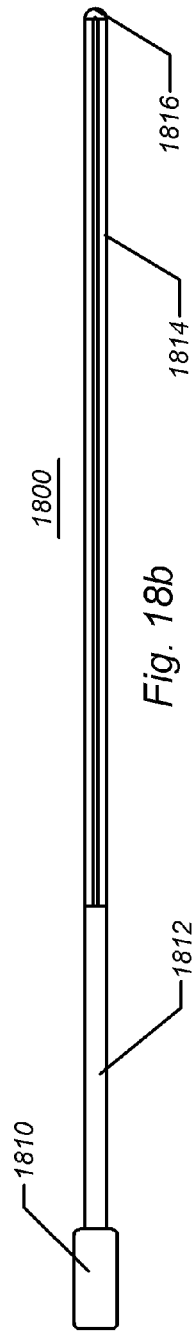
Fig. 18b
Fig. 18c
Fig. 18d

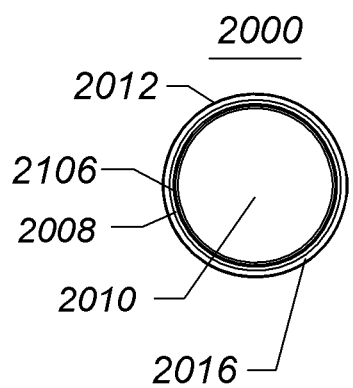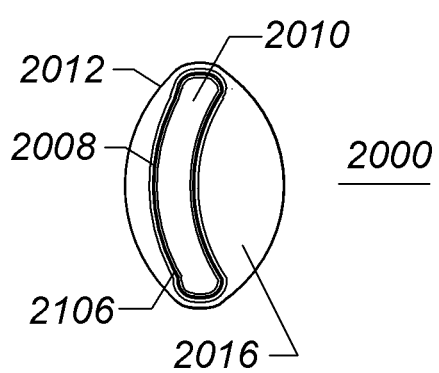
FIG. 27A    FIG. 27B
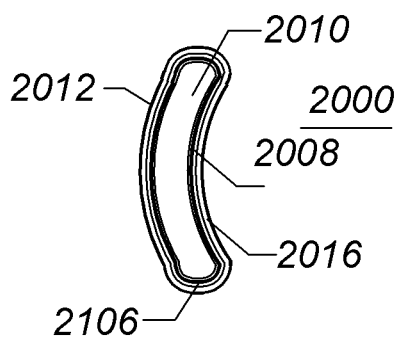
FIG. 27C

EXPANDABLE ILIAC SHEATH AND METHOD OF USE

PRIORITY CLAIM

This application claims the benefit of priority under U.S.C. §119 of U.S. Provisional Patent Application Ser. No. 61/326,567, entitled "Expandable Iliac Sheath and Method of Use," filed on Apr. 21, 2010, and this application is a continuation-in-part of International Patent Application No. PCT/US2009/044031, entitled "Expandable Iliac Sheath and Method of Use," filed on May 14, 2009, which is a continuation-in-part of U.S. patent application Ser. No. 12/258,233, entitled "Expandable Iliac Sheath and Method of Use," filed on Oct. 24, 2008, which claims the benefit of priority of U.S. Provisional Patent Application No. 61/127,619, filed May 14, 2008, entitled "Expandable Iliac Sheath and Method of Use" and this application is a continuation-in-part of U.S. patent application Ser. No. 12/258,233, entitled "Expandable Iliac Sheath and Method of Use," filed on Oct. 24, 2008, which claims the benefit of priority of U.S. Provisional Patent Application No. 61/127,619, filed May 14, 2008, entitled "Expandable Iliac Sheath and Method of Use." The contents of each of these applications are hereby incorporated by reference in their entireties.

BACKGROUND OF THE DISCLOSURE

1. Field of the Invention

The present inventions relate to medical devices for percutaneously accessing body lumens and, more particularly, to methods and devices for accessing the cardiovascular system.

2. Description of the Related Art

A wide variety of diagnostic or therapeutic procedures involve the introduction of a device into the vasculature through a percutaneous or open surgical incision at an access site. Such regions of the vasculature, preferred for access, include both the iliac, subclavian, and femoral arteries. A percutaneous technique commonly known for such vascular access is the Seldinger technique. The Seldinger technique involves using a hollow needle to puncture the skin and gain access to the selected artery or vein. A guidewire is next placed through the hollow needle into the selected region of vasculature. The guidewire may be advanced to a target location in the vasculature, which can be more than 100 cm away from the access site. The needle is removed and a tapered dilator with a sheath and a central lumen in the dilator is advanced over the guidewire into the vasculature. The dilator is next removed and a guide catheter is advanced through the sheath over the guidewire. The guide catheter can be advanced all the way, or part way, to the target site. The guide catheter, following, or without, removal of the guidewire can be used for directing therapeutic or diagnostic catheters to regions of the vasculature and central circulation, including external and internal structures of the heart. A general objective of access systems, which have been developed for this purpose, is to minimize the cross-sectional area of the access lumen, while maximizing the available space for the diagnostic or therapeutic catheter placement therethrough. These procedures are especially suited for coronary angioplasty, stent placement, cardiac valve replacement, stent-graft placement, cerebrovascular embolic coil placement, diagnostic cardiac catheterization, cardiac assist, and the like.

One type of cardiac procedure involves placement of a collapsible cardiac valve in either the aortic, tricuspid, or mitral position. Today, an aortic valve replacement procedure involves the steps of inserting a hollow needle, with a hemostasis valve affixed to the proximal end, into the femoral or iliac artery of a patient via a percutaneous puncture. A guidewire is next inserted through the hemostasis valve and the central lumen of the needle into the femoral or iliac artery. The guidewire is routed, under fluoroscopic control, cranially toward the heart, through the aortic arch, through the aortic valve and into the left ventricle. The hollow needle is removed from the patient leaving the guidewire in place. An introduction sheath, including a tapered tip central obturator or dilator having a hemostasis valve at the proximal end and further including a central guidewire lumen is routed over the guidewire, through the skin puncture, through the wall of the artery, and into the central lumen of the iliac artery or aorta. The central obturator or dilator is removed. A valve delivery catheter is next advanced over the guidewire and through the introduction sheath to the region of the aortic root. The aortic valve is deployed in the region of the aortic root such that the remnants of the original valve are outwardly dilated by the implant, which includes a valve and expandable support stent. The valve is seated firmly so as to become secured to the aortic valve remnant. The delivery catheter is next removed from the patient leaving the new valve in place. The sheath is next removed and hemostasis is established using standard techniques for a vessel puncture wound. Indications for percutaneous valve replacement include a stenotic or incompetent aortic valve and a contraindication to open surgical valve replacement.

Issues can arise, however, when the delivery catheter or sheath are removed from the patient. Withdrawal of large catheters and sheaths has been reported to cause disruption of vessel plaque during removal or pullback through the aorta, iliac and femoral arteries. This is especially problematic in very sick patients with significant vascular disease that involves plaque, mural thrombus, aneurysms, and other pathologies. The disruption of a region of plaque or thrombus can cause emboli to break free from the vessel wall, float downstream, and lodge within the lumen of smaller distal vessels, blocking blood flow, and resulting in ischemia and possibly tissue necrosis. Not only during withdrawal, but also during insertion, do issues arise with insertion of sheaths and catheters. In patients suffering from substantial cardiovascular disease, atheroma, thrombus, and other plaque can build up on the interior of the abdominal aorta, iliac arteries, and femoral arteries. These vessels can have their lumen diameters substantially reduced by these buildups and furthermore, the vessels can become highly tortuous. Thus, insertion of catheters, especially large diameter catheters and introducer sheaths can be difficult or impossible because of vessel stenosis or wall interference.

Suggested further reading related to the use of iliac or femoral introducers for large catheters includes Gawenda M, and Brunkwall J, Device-Related Problems of Thoracic Stent-Grafts, 1: *Zentralbl Chir.* 2007 June; 132(3):205-10, the entirety of which is hereby incorporated by reference herein.

It is desirable to protect the arteries, including the femoral and iliac arteries, from a delivery catheter and sheath during removal. A need remains, therefore, for improved access technology, which allows a large diameter catheter or sheath to be percutaneously or surgically introduced through the iliac, femoral, or subclavian arteries, and then be removed without causing further injury or complications to the patient.

SUMMARY OF THE INVENTIONS

One arrangement includes an introducer sheath having a first, smaller cross-sectional area and a second, larger cross-sectional area. In other arrangements, the introducer sheath can have a third, smaller cross-sectional area that may substantially be the same as the first, smaller cross-sectional area or intermediate the first, smaller cross-sectional area and the second, larger cross-sectional area. The introducer sheath can include a hub and a length of sheath tubing. The sheath tubing and the hub can form an axially elongate structure having a proximal end, a distal end, a wall, and a lumen extending from approximately the proximal end to the distal end. In certain embodiments, the sheath tubing can have a proximal section, a central section, and a distal section. The proximal section can be partially expandable, fully expandable, or completely non-expandable, diametrically. In some embodiments, the distal section can be expandable. The introducer sheath can be suitable for iliac access, femoral access, trans-femoral access, subclavian artery access, or aortic access.

The sheath can be used as an introducer for long guiding sheaths, other expandable sheaths, or catheter systems. The expandable sheath can have the clinical benefit of being able to radially dilate tissue, thus causing minimal tearing and tissue trauma. The expandable sheath can be used to assist with percutaneous vascular access procedures in that it can allow for a small diameter access to the femoral, iliac, or subclavian arteries that can then be expanded into a size large enough for introduction of large interventional, therapeutic, or diagnostic devices therethrough. Interventional cardiologists generally prefer to perform interventional procedures where the access is percutaneous and does not require a surgical cutdown. Should a surgical cutdown be required for access, a surgeon is generally brought in to perform the access. The expandable arterial access sheath can eliminate the need for a cutdown and the surgical support, reducing time, procedure cost, trauma to the patient, and improving patient outcomes.

In certain embodiments, the central section can be expandable. In some embodiments, the central section can include a polymeric wall with reinforcing elements that can maintain the cross-sectional shape of the central section prior to expansion, and after expansion. In some embodiments, the central section can include a polymeric wall that can be non-distensible but otherwise foldable and free from any reinforcing elements. In these non-reinforced embodiments, the central section can possess the properties of flexibility but can have minimal structure and thus, cannot maintain a cross-sectional shape. In some embodiments, the central section can include longitudinally disposed reinforcing elements that provide column strength and tensile strength but offer little or no cross-sectional shape retention.

In some embodiments, the distal section can include a polymeric wall with reinforcing elements that provide a degree of retention of cross-sectional shape. The distal section can include weak reinforcing elements that provide some control over the shape of the polymeric wall but can be easily deformed into a collapsed configuration upon exposure to external forces such as those imposed by a blood vessel wall. The distal section can include polymeric materials that can be plastically deformed and do not substantially spring back following dilation. In some embodiments, the distal end can be subject to remodeling by inflation of the expansion balloon under pressures ranging between 10 and 40 atmospheres.

In some embodiments, the distal end of the sheath can include a flared component that becomes larger in diameter as the sheath extends axially in the distal direction. The flared component can include a taper, or it can include a taper and a region of relatively constant diameter coupled to or integral to the tapered region at the most distal end. The flared component can be integral to the distal end of the expandable portion of the sheath, or it can be coupled thereto. The flared component can be expanded using a balloon dilator, it can be expanded using self-expansion modalities, or it can include self-expansion with balloon dilator assist. The self-expansion can be due to resilient spring forces, or due to shape memory forces generated by sheath reinforcement components fabricated from nitinol, or other shape memory materials. The flared configuration can facilitate re-capture or removal of instruments or implantable devices such as percutaneously delivered aortic heart valves. In an exemplary embodiment, the flared configuration can also facilitate removal of the natural aortic valve root, should excision of the aortic valve root be required. The expandable, flared region of the sheath can range in length between 1-cm and 10-cm, with a preferred range of 2-cm to 5-cm. In some embodiments, the flared region can use the same balloon as the rest of the distal expandable region for expansion. In some embodiments, the flared region can be expanded by a separate balloon.

In some embodiments, the proximal end of the sheath can include a hub incorporating one or more hemostasis-type valves. The hub can include a single catheter insertion port or can include a plurality of catheter insertion ports. Each catheter insertion port preferably includes hemostasis valves, stopcocks, or the like to prevent blood leakage from the catheter. The hub can further include one or more purge ports, which can operably couple to the internal lumen of the hub and can be terminated by stopcocks or other valves.

In some embodiments, the diametrically or radially expandable elements of the catheter can be configured as a tube having a plurality of longitudinal folds. The expandable regions or elements, located in the proximal section, distal section, or the center section of the sheath or catheter, can be creased into these folds and bent to form a first, smaller, folded cross-sectional area. The expandable regions or elements can be folded over a central dilator catheter including, for example, an angioplasty-type balloon, a catheter shaft, a balloon inflation port at the proximal end, a guidewire lumen, and the like. Upon selective inflation of the angioplasty-type, non-elastomeric, non-distensible, balloon by application of fluid pressure into an appropriate port on the proximal end of the dilator catheter, the expandable regions can unfold into a second, larger, cross-sectional shape. The central dilator catheter can be deflated and removed from the sheath to create a large cross-section center lumen suitable for the introduction of catheters, delivery catheters, implantable devices, or the like.

In some embodiments, the expandable introducer sheath includes a proximal, expandable section. The proximal expandable section includes a composite tubular structure fabricated from an inner polymeric layer of polyethylene, an outer polymeric layer of polyethylene, and a reinforcement layer sandwiched between the two polymer layers. The reinforcement layer can include a coil of flat, fully annealed, stainless steel wire with a width of about 0.010 inches, with a range of 0.005 to 0.025 inches, and a thickness of about 0.003 inches, with a range of 0.002 to 0.004 inches. The proximal, expandable region can be coupled to the proximal end to a non-expandable length of sheath tubing of the same or similar inside diameter, or it can be coupled directly to the sheath hub. The distal end of the proximal expandable region can be coupled to a central expandable region that includes inelastic polymeric materials. The central expandable region can include a membrane of polymers bonded, welded, or surrounding a braid, or other fabric reinforcing structure that provides a level of column strength and a level of tensile strength for the central expandable region. The distal end of the central expandable region can be coupled to a distal expandable region configured similarly to the proximal expandable region except that the distal expandable region can be somewhat weaker so that the distal expandable region can be easily collapsed following expansion.

In some embodiments, the sheath tubing can include a proximal region wherein a reinforcing layer of spring stainless steel ribbon can be wound into a coil with a width of about 0.005 to 0.025 inches and a thickness of about 0.002 to 0.004 inches. The coil spacing can range between 0.001 inches and 0.050 inches.

In another embodiment, the sheath can include a proximal non-expandable region and a distal expandable region. The distal expandable region can include between 10% and 95% of the catheter shaft length.

The distal, expandable region can include a reinforcing layer of malleable stainless steel ribbon or flat wire wound into a coil with similar dimensions as in the proximal region. The entire length, or a substantial portion thereof, can include an additional reinforcing layer, or layers, of braided material fabricated from materials such as, but not limited to, PEN, polyester, stainless steel, titanium, nitinol, cobalt nickel alloy, polyamide, polyimide, or the like. In some embodiments, the reinforcing structure, generally sandwiched between an outer and an inner layer of polymeric wall, can include an inner layer of polymer overlaid by a first reinforcing braid layer, overlaid by a coil reinforcement, finally overlaid with an outside layer of polymeric material. In another embodiment, the inner layer of polymeric material can be overlaid by the coil reinforcement, which can be overlaid by the braided reinforcement, which can be finally overlaid with the outside layer of polymeric material. In some embodiments, the inner layer of polymeric material can be overlaid by the braided layer, which can be overlaid by the coil winding, which can be overlaid by another layer of braid, which can be finally overlaid by the outer polymeric layer.

In some embodiments, the sheath dilator can be configured with a PET balloon coupled to a Hytrel shaft. The Hytrel shaft can include an inner and an outer tube concentrically disposed with an annulus between the two tubes. The distal end of the dilator balloon can be coupled to the inner Hytrel tubing. The proximal end of the dilator balloon can be larger in diameter and can be coupled to the outer Hytrel tubing in this embodiment. The outer Hytrel tubing can extend just inside the center volume of the dilator balloon and the annulus between the outer tube and the inner tube can be in fluid communication, operably connected to, the center volume of the dilator balloon. The annulus can be operably in fluid communication with an inflation port integral to, or coupled to, the dilator hub. In some embodiment, an outer polymer tube, such as the outer Hytrel tube of the preceding embodiment, can be omitted and the dilator balloon can include a proximal tail that can extend proximally to bond and seal within the dilator hub or sidearm. In some embodiments, the pressurization annulus for the balloon can reside between the dilator balloon and the inner polymer tube, the pressurization annulus being operably connected to an inflation port on the dilator hub. The interior of the inner dilator tube includes a guidewire lumen suitable for advancing the entire system over a guidewire suitable for aortic access. Such aortic access guidewires typically can be 0.035 or 0.038 inches in diameter and can be relatively stiff.

The sheath can be folded into one or more longitudinally oriented folds and wrapped around the dilator, with collapsed dilator balloon. The malleable elements in the proximal and distal expandable regions can maintain the configuration of the system in the collapsed state. An optional outer jacket, which can have attached, peel-away, tear-away, or removable before use configurations, can be used to encase part or all of the diametrically collapsed sheath tubing. In some embodiments, the sheath can further include a thin FEP, PFA, or PTFE tube over the outside of the sheath. This fluoropolymer outer covering need not be removed. The outer covering can function to protect a soft polyethylene sheath material from hard vascular deposits such as atheroma.

In some embodiments, the central region can include elastomeric polymer structure with an optional braid reinforcement that can permit the central region to simply expand diametrically from a first smaller diameter to a second larger diameter without the use of folds. An internal slip layer of PTFE, FEP, PFA, or other highly lubricious material can be used to facilitate passage of a catheter through the central region to prevent clinging. The internal slip layer can be the inner layer of the polymer sandwich within which the reinforcing coils or braids can be embedded.

Once the expandable introducer sheath has been advanced so that the distal end reaches just above the aortic bifurcation, the dilator is expanded at pressures of between 10 and 40 atmospheres, and preferably between 15 and 30 atmospheres. The dilator can next be deflated and removed from the central lumen of the sheath.

In some embodiments, the sheath can include a flexible shaft configured with an elastomeric outer membrane and a reinforcing layer configured as a braided structure that is capable of changing the diameter. The sheath can be inserted into a patient in a first, smaller cross-sectional configuration, preferably over a small diameter dilator or tapered obturator. The obturator or tapered dilator can next be removed and a hollow central dilator of large diameter can be inserted into the interior lumen of the sheath. Upon insertion of the large diameter, hollow central dilator into the flexible shaft of the sheath, the sheath can expand diametrically to a second, larger, cross-sectional area, diameter, or radius. One or more catheters can be inserted therethrough to reach a target site within the vasculature. Following completion of the procedure, the central dilator can be removed resulting in elastomeric contraction of the outer membrane to a first, smaller cross-sectional area. The sheath can next be removed from the patient in the first, smaller, cross-sectional area configuration. The sheath can be configured using principles and design elements as described in U.S. Pat. No. 7,309,334 by Gerard von Hoffmann, titled "Intracranial Aspiration Catheter", the entirety of which is hereby incorporated herein by reference.

The reinforcement of the expandable regions can include wire, preferably malleable wire. The wire can have a round cross-section, a rectangular cross-section, a ribbon-like cross-section, or the like. The malleable wire can be bent by a dilator balloon, tapered dilator, hollow dilator, or the like, into the second, larger cross-section and the strength of the malleable wire can substantially overcome any resilient spring-back imparted by the polymeric component of the sheath wall.

In some embodiments, the wire can have elastomeric properties or shape memory properties. These embodiments can utilize shape-memory wire, pseudoelastic wire, superelastic wire, elastomeric wire, or the like. The wire can be nitinol, stainless steel, cobalt nickel alloy, or the like. The wire, in the shape-memory configuration can have an austenite finish temperature of around 25 to 35 degrees centigrade, preferably between 28 and 32 degrees centigrade so that body temperature blood can cause the wire mesh to be biased to the larger, expanded configuration.

In some embodiments, the expandable region can include polymeric encapsulation of a braided or otherwise expandable shape memory reinforcing structure. The reinforcing elements or structure can have shape-memory characteristics. The sheath is inserted into the patient in the first, small cross-sectional area. The reinforcing elements can be maintained below the martensite start temperature so that the reinforcing elements can be substantially malleable, even at body temperature (approximately 37° C.). The sheath wall can next be dilated with the balloon dilator as described herein. The dilator can next be removed and the sheath can become host to therapeutic or diagnostic catheters, which can be inserted therethrough. Following removal of the catheters, electricity can be applied to lead wires at proximal end of the sheath. The electrical leads can be operably connected to heaters in the vicinity of the reinforcing elements, or the electrical leads can be operably connected to each end of the reinforcing elements. The electricity causes Ohmic or resistive heating of the reinforcing elements to above their austenite finish temperature. The reinforcing structure, having been shape-set in the small diameter configuration, can return to that small diameter configuration, bringing the entire expandable sheath wall down with it, to facilitate removal of the sheath from the patient. An austenite finish temperature of around 42° C. can be used in this application.

The dilator catheter can include an inner and outer member. The materials of the inner member and the outer member can include Hytrel, PEEK, composite, reinforced construction, polyester, polyurethane, polyethylene, or the like. The catheter hub can be fabricated from materials such as, but not limited to, polycarbonate, acrylonitrile butadiene styrene (ABS), polyurethane, polyvinyl chloride, and the like. The dilator balloon can be fabricated from stretch blow-molded polyester polyamide, polyamide, or polyester blends, using materials such as, for example, Eastman PET 9921 or similar.

In some embodiments, a coating is applied to the expandable areas to generate an inwardly biased, radially oriented contraction force. The expandable area can be forced to expand radially against the bias force of the coating. Once the radial expansion force is removed, the expandable area can remain biased radially inward toward the smallest diameter, to which it can travel unless prevented from doing so.

The system can include radiopacity enhancements to improve visualization under fluoroscopy. Radiopaque markers can be coupled to the distal end of the sheath to denote the distal end, the extents of the expandable region or regions, or even the orientation of the sheath. The radiopaque markers can include bands or windings of metal such as, but not limited to, tantalum, platinum, platinum iridium, gold, and the like.

In some embodiments of the sheath wall construction, an inner layer of polymer and an outer layer of polymer can sandwich a reinforcing layer. The reinforcing layer can be a coil of metal such as, but not limited to, titanium, stainless steel, cobalt nickel alloy, nitinol, tantalum, or the like. The coil can preferably be malleable, with little or no spring properties, and not exhibit any elastomeric tendencies. The coil can be fabricated from flat wire with a thickness of 0.001 to 0.010 inches and preferably 0.002 to 0.005 inches. The width of the flat wire can range from 0.005 to 0.050 inches and preferably from 0.008 to 0.025 inches. The spacing between the coils can, for example, range from substantially 0 to approximately 5 times the width of the coil wire. The coils can be fabricated from round stock, flat stock, or the like. The reinforcement can be sandwiched between the inner layer and the outer layer of polymeric material, wherein the inner and outer layers can be bonded or welded to each other through the space between the coils. The inner and outer polymeric layers can be fabricated from the same or different materials. Suitable materials for the inner and outer layers include, but are not limited to, polyurethane, silicone, Hytrel, PEEK, polyethylene, HDPE, LDPE, polyester, polyethylene blends, or the like. In some embodiments, a plastically deformable, malleable, or annealed, braid structure can also be used for reinforcement to beneficially eliminate the need for the malleable coil and permit a reduction in wall thickness while retaining the tensile strength and torqueability of the braid.

In some embodiments, the sheath shaft can include multiple regions of varying flexibility along the axial length of the shaft. In some embodiments, the catheter shaft can have at least two regions of different flexibility. In some embodiments, the catheter shaft can include three or more (with a practical upper limit of six) regions of different flexibility. In some embodiments, the sheath shaft flexibility can be reduced toward the proximal end of the catheter and increased moving toward the distal end of the catheter. Moving from the proximal to the distal end of the catheter shaft, the flexibility of a given discreet section can be greater than the flexibility of the region just proximal and adjacent to said discreet section. A sheath having a substantially collapsed, small diameter distal region can exhibit significantly increased flexibility in that area over the flexibility in non-expandable, or fully expanded, expandable regions. Such flexibility can be especially useful when traversing tortuous or curved anatomy such as the aortic arch. Following such traverse, the sheath can be expanded to create a stiffer, larger diameter structure. Such construction can be especially useful for the delivery catheter for an aortic valve, which needs to approach the aortic root from the anatomically distal (downstream) aspect.

Another embodiment includes a catheter configured to deliver a valve to the heart. In an embodiment, the delivery catheter for an aortic valve can be configured with an expanded inner diameter ranging from about 12 French to about 40 French, with a preferred range of about 16 French to 26 French. In an unexpanded configuration, the distal, unexpanded outside diameter of the delivery catheter for the aortic valve can range between about 6 French and 16 French. The length of the distal, expandable region can, in some embodiments, equal at least the arc length of the aortic arch and can range between about 15 cm and 40 cm. In some embodiments, the sheath can have a working length of about 9 to 55 cm with preferred working lengths ranging from about 15 to 45 cm. The general construction of the aortic valve delivery catheter can be as described in U.S. Provisional Patent Application Ser. No. 60/674,226, filed Apr. 22, 2005, titled Expandable Trans-Septal Sheath, the entirety of which is hereby incorporated herein by reference. In some embodiments, an expandable delivery sheath can be used to deliver a catheter, or a prosthesis, to the heart through the subclavian artery. In some embodiments, the sheath working length can be generally shorter than the working length of an iliac access sheath. In some embodiments anticipated herein, the valve prosthesis replacement can be delivered retrograde to the aortic valve root.

In some embodiments, the iliac, or iliofemoral, sheath can be configured to be inserted into the femoral or iliac arteries and can be routed so that the distal end is within the aorta. In some embodiments, the working length of the introducer sheath can be such that the sheath reaches just proximal to the aortic bifurcation. In some embodiments, the working length of the introducer can be such that the sheath can reach well into the descending abdominal aorta and can extend to a position approximately between the aortic bifurcation and the renal arteries, or just beyond. In some embodiments, the working length of the introducer sheath can range between about 20 and 55 cm with a preferred length of 25 to 45 cm. The expandable distal region can include nearly, or substantially, all of the sheath tubing, leaving only a small non-deformable or non-expandable region at the proximal end to facilitate attachment to the sheath hub.

In some embodiments a method of use can include an expandable iliac sheath which can be provided in an aseptic, or sterile, package and can be sterilized by ethylene oxide, gamma irradiation, electron beam irradiation, or the like. The patient can be prepared in the standard hospital fashion for surgery and can be appropriately draped. A percutaneous needlestick can be made into the iliac arteries using the Seldinger technique described earlier in this document. A guidewire can be advanced through the hollow 18-gauge needle and the needle can be removed. The percutaneous access site can optionally be dilated with an Amplatz dilator or similar device at this time. The introducer sheath, in the first, small cross-sectional configuration with the dilator, can be advanced over the guidewire and into the iliac artery where it can be advanced into the abdominal aorta. The introducer sheath can next be dilated to the second, larger cross-sectional configuration, using the pre-inserted dilator or by other suitable means. The dilator can next be removed and any hemostasis valves can be checked for closure at the proximal end of the sheath. Interventional catheters can next be advanced through the expandable introducer sheath and toward their anatomical target. Following completion of the procedure, the interventional catheters can be removed from the expandable iliac introducer sheath, again checking to ensure that there is no hemorrhage from the valves or ports at the proximal end of the sheath. The sheath can be removed from the patient in one of three ways. In some embodiments, the sheath can be simply withdrawn from the patient without collapsing the sheath. In some embodiments, the sheath can be withdrawn from the patient without actively collapsing the sheath but the sheath collapses slightly following removal of the interventional catheters to ease withdrawal. In some embodiments, the sheath can be actively reduced in diameter or cross-section and can then be withdrawn from the patient. Hemostasis can be maintained using standard hospital technique or by the application of a commercial percutaneous access hemorrhage control device.

Some embodiments of the sheath can cause sheath re-collapse, in the radial, diametric, or cross-sectional directions. In some embodiments, shape-memory nitinol can be heated to above body temperature to cause restoration to austenite finish temperature and return to a pre-set, collapsed shape. In some embodiments, the outer layer of the sheath can be separate from inner layers. The outer layer of the sheath can include substantially non-compliant material or it can include substantially semi-compliant materials, or a combination thereof. An inflation port at the proximal sheath hub can be operably connected to the potential space between the outer layer of the sheath and the inner layers. Pressurization of the potential space between the outer layer and the inner layers can preferentially coerce, crush, force, deform, collapse, re-fold, or otherwise move the inner layers inward to a greater degree. Following removal of the pressurization within the potential space, the collapsed sheath and the now flaccid outer layer can be removed from the patient with less potential to scrape or cause damage to the walls of the artery or blood vessel. In some embodiments, the outer layer can include two layers sealed to each other such that pressurization occurs between the double wall outer layer. These embodiments can be useful when it is difficult to seal the outer layer to the inner layers due to material incompatibilities. In other embodiments, the sheath can include an outer pressure jacket and a side-balloon disposed alongside the sheath tubing running substantially parallel to the longitudinal axis of the sheath tubing. Pressurization of the side-balloon can cause the sheath wall to collapse or re-fold due to the force generated between the outer pressure jacket and the deformable sheath tubing by the side-balloon. In some embodiments, the side-balloon can be folded in half lengthwise and stacked so that both balloon chambers provide force against the sheath tube when inflated. The folded side-balloon advantageously can function without the need for a distal seal, which can be difficult to create in the types of materials necessary for these balloons.

The main reasons for the malleable embodiments include control over cross-sectional shape, ability to embed the reinforcement in the polymer layers without needing to create some difficult-to-manufacture decoupling of the polymer and the reinforcement, the high strength of the sheath following placement, and prevention of lumen re-collapse caused by body tissue. The ability of this device to remodel to the desired shape to generate a superhighway for placement of implants and other medical devices is superior to anything available today. Furthermore, the device can provide a relatively smooth interior lumen, which can allow passage of instruments and implants of very large size without excessive binding or friction. No other sheath exists today that has these benefits. The malleable reinforcements embedded within the sheath can be configured to generate sufficient force that they can control and maintain the diameter of the radially collapsed, unexpanded sheath. The malleable reinforcements can be further configured to maintain the sheath in the open, radially expanded configuration, following dilation with a balloon or other dilator, residing within the sheath lumen. The structure of the malleable metal reinforcement can be sufficient to overcome, or dominate, any resilient or structural forces exerted by the polymeric components of the sheath tubing, which generally can surround, or encase, the reinforcement. The structure of the malleable metal reinforcement also can be sufficient to overcome any inwardly biased forces imposed by any tissue through which the sheath can be inserted, such as, for example, muscle mass and fascia lying between the skin and the femoral or iliac arteries.

In some embodiments, the sheath assembly can include a malleable reinforcement embedded within a polymeric sheath material which can form an axially elongate tube having a proximal end, a distal end, and a lumen extending therethrough. The sheath can further include a substantially non-distensible outer pressure jacket that surrounds the exterior of the polymeric sheath material but which can not be attached thereto. A secondary balloon can be provided, in the collapsed configuration, between the pressure jacket and the exterior of the polymeric sheath wall. Following expansion of the sheath by means of an internal dilator located within the primary lumen of the sheath and deflation of the dilator, the sheath can be used to introduce other medical instruments, catheters, and the like. At the conclusion of the procedure, or other desired point in the procedure, the secondary balloon can be inflated to compress the radially expanded sheath inward. The secondary balloon can be held against the sheath wall by the pressure jacket. Inflation of the secondary balloon can punch in one side of the sheath and can generate tension on the pressure jacket that causes the sheath to fold into a "U" shape. Deflation of the secondary balloon can now result in a sheath with a much-reduced cross-sectional profile that is easily removable from the patient. In some embodiments, the secondary balloon can be provided with a closed distal end, like a soda bottle, to minimize the chance of leakage. In some embodiments, the secondary balloon can be sealed to itself at the distal end using welding techniques, adhesives, crimping, fasteners, or the like. The proximal end of the secondary balloon can be coupled and operably connected to an inflation port or lumen. In some embodiments, the secondary balloon can be folded back on itself at the distal end such that the secondary balloon forms a double balloon that can be stacked radially to maximize the refolding tendency and to eliminate a distal balloon weld or seal that could potentially leak. In some embodiments, the secondary balloon can be positioned along and inside the longitudinal fold of the compressed primary sheath tube. The presence of the folded secondary balloon, or even slight inflation thereof can reduce any bleeding that occurs through the channel created by the fold between the interior of the patient blood vessel and the exterior region of the vessel or of the patient.

In some embodiments, where the sheath refolding can be generated by pressure buildup between the pressure jacket and the sheath itself, the distal bond can be reinforced by folding the pressure jacket over the distal end of the sheath, everting the pressure jacket distal end inside the sheath, and subsequent heat sealing or welding of the distal end of the pressure jacket to the sheath distal end. Such an everted pressure jacket distal end may benefit from a necking operation to reduce the diameter prior to eversion and welding. A high-pressure balloon such as one fabricated from PET, Nylon, or the like, can be used to iron out wrinkles on the interior of the distal end of the sheath prior to welding. The everted pressure jacket can, in some embodiments, be welded to the exterior of the main sheath tube, rather than the interior.

In some embodiments, a shim, such as a short tube fabricated from PET or other suitable polymer, can be inserted into the interior of the sheath to increase the strength and minimize the risk of blowout through the sheath polymer wall, which can be fabricated from Hytrel for example and which can generally be weaker than the PET pressure jacket but can be bonded thereto. The shim can have a length ranging between about 0.020 and 0.500 inches with a preferred range of about 0.050 inches to about 0.250 inches. Such reinforcements of the polymeric wall and pressure jacket at the distal end of the sheath can help prevent peeling apart of the welded layers and use the pressure to force the layers together, rather than apart.

In some embodiments, the inner layer of sheath material, which can be Hytrel 55D for example, can be brought forward past the distal end of the sheath, folded outward, and welded to the PET pressure jacket. The welding can be performed using radiofrequency heating, hot air heating (hot box), laser welding, a resistive heater, ultrasonic welding, or the like. Heating temperatures can range between about 300° F. and 600° F., depending on the tubing thicknesses, configurations, chemical makeup, and the like with temperatures of about 400° F. being suitable for welding PET to Hytrel. Expanding collets, tapered mandrels, exterior heat shrink tubing and other manufacturing aids can be used to compress the tubing and facilitate welding with the application of heat. Mandrels can be fabricated from PTFE or other fluoropolymers to provide for easy removal following the bonding process.

The proximal end of the pressure jacket can be routed into an annulus or lumen that can be operably connected to a collapse or refolding pressure port on the sheath hub. The collapse pressure port can be terminated with a female Luer lock or other suitable medical connector and can further include a valve such as a stopcock or one-way check valve to prevent fluid loss except when a male Luer can be inserted therein.

In some embodiments, an internal pressure jacket can be provided that can be coupled to the interior of the sheath polymeric tubing such that pressurization of the space between the internal pressure jacket and the sheath tubing causes the internal pressure jacket to collapse radially inward and the sheath tubing to expand radially outward. Following radial expansion of the sheath tubing, the space between the internal pressure jacket and the sheath tubing can be evacuated of fluid to pull the internal pressure jacket against the inside diameter of the sheath lumen and maximize the lumen for instrument and catheter passage. In this embodiment, the sheath can be radially expanded without the need for a separate, removable dilator. The same exterior pressure jacket or parallel secondary balloon can be used to re-collapse this design prior to removal from the patient.

For purposes of summarizing the invention, certain aspects, advantages and novel features of the invention are described herein. It is to be understood that not necessarily all such advantages may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein. These and other objects and advantages of the present invention will be more apparent from the following description taken in conjunction with the accompanying drawings.

BRIEF DESCRIPTION OF THE DRAWINGS

A general architecture that implements the various features of the invention will now be described with reference to the drawings. The drawings and the associated descriptions are provided to illustrate embodiments of the invention and not to limit the scope of the invention. Throughout the drawings, reference numbers are re-used to indicate correspondence between referenced elements.

FIG. 3A illustrates an expandable introducer sheath having three regions of expandability, in a radially collapsed configuration with a dilator catheter in place, according to an embodiment of the invention;

FIG. 3B illustrates the expandable introducer sheath of FIG. 1A in a radially expanded configuration and with the dilator catheter removed, according to an embodiment of the invention;

FIG. 4A illustrates a one-way expandable introducer sheath having a single area of expandability, in a first, unexpanded configuration with a dilator inserted therein, according to an embodiment of the invention;

FIG. 4B illustrates the one-way expandable introducer sheath of FIG. 4A in an expanded configuration with the dilator having been removed, according to an embodiment of the invention;

FIG. 4C illustrates a dilator capable of expanding the sheath, with the dilator balloon in an expanded configuration, according to an embodiment of the invention;

FIG. 5A illustrates a two-way expandable introducer sheath having a single area of expandability, in a first, unexpanded configuration, according to an embodiment of the invention;

FIG. 5B illustrates the two-way expandable introducer sheath of FIG. 5A in a second, expanded configuration, according to an embodiment of the invention;

FIG. 5C illustrates the two-way expandable introducer sheath of FIG. 5A following return to a third, actively collapsed configuration, according to an embodiment of the invention;

FIG. 6A illustrates an expandable introducer sheath and dilator, in a first, radially collapsed configuration, according to an embodiment of the invention;

FIG. 6B illustrates the expandable introducer sheath of FIG. 6A having been radially expanded and the dilator removed, according to an embodiment of the invention;

FIG. 6C illustrates the fully expanded introducer sheath of FIG. 6A with a prosthetic cardiac valve delivery catheter having advanced a prosthetic cardiac valve through the sheath, according to an embodiment of the invention;

FIG. 16a illustrates a short, expandable, re-collapsible iliofemoral introducer sheath and dilator in a first, radially collapsed configuration, according to an embodiment of the invention;

FIG. 16b illustrates the expandable, re-collapsible iliofemoral introducer of FIG. 16a in a second, radially expanded configuration with the inflated dilator still in place, according to an embodiment of the invention;

FIG. 16c illustrates the iliofemoral introducer of FIG. 16b with the dilator removed and the space between an outer jacket and the introducer sheath pressurized to collapse the introducer sheath distal tube to a third, radially collapsed configuration, according to an embodiment of the invention;

FIG. 17a illustrates a collapsing obturator for use with expandable introducer sheaths, according to an embodiment of the invention;

FIG. 17b illustrates the collapsing obturator of FIG. 17A having been inserted into a diametrically expanded introducer sheath, and then pressurized to expand two sealing balloons, according to an embodiment of the invention;

FIG. 17c illustrates the collapsing obturator of FIG. 17A within the introducer sheath with the two sealing balloons inflated and the region between the sealing balloons but outside the collapsing obturator depressurized to radially collapse the expandable introducer sheath tubing, according to an embodiment of the invention;

FIG. 18a illustrates an expanded view of the expandable, re-collapsible introducer of FIGS. 16a-16c showing the inflation and deflation lumen within the hub and outer jacket, according to an embodiment of the invention;

FIG. 18b illustrates a side view of a forming obturator configured to control the shape of the distal collapsible region of an introducer sheath, according to an embodiment of the invention;

FIG. 18c illustrates a cross-sectional view of a forming or collapsing obturator having a three-pronged profile, according to an embodiment of the invention;

FIG. 18d illustrates a cross-sectional view of a forming or collapsing obturator having a splayed U configuration, according to an embodiment of the invention;

FIG. 27A illustrates a cross-sectional end view of a distal, collapsible end of a sheath that is fully expanded, wherein the sheath includes a sheath wall and an outer pressure jacket, according to an embodiment of the invention;

FIG. 27B illustrates a cross-sectional end view of the distal, collapsible end of the sheath of FIG. 27A wherein the region between the outer pressure jacket and the sheath wall has been pressurized to collapse the sheath wall, according to an embodiment of the invention;

FIG. 27C illustrates a cross-sectional end view of the distal, collapsible end of the sheath of FIGS. 27A and 27B wherein the region between the outer pressure jacket and the sheath wall has been evacuated to collapse the outer pressure jacket and sheath exterior, according to an embodiment of the invention;

DETAILED DESCRIPTION OF THE PREFERRED EMBODIMENTS

As used herein, the terms proximal and distal refer to directions or positions along a longitudinal axis of a catheter or medical instrument. Proximal refers to the end of the catheter or medical instrument closest to the operator, while distal refers to the end of the catheter or medical instrument closest to the patient. For example, a first point is proximal to a second point if it is closer to the operator end of the catheter or medical instrument than the second point. However, the terms anatomically proximal and anatomically distal refer to orientations within the body. A point is more anatomically distal if it is further from the heart than a point described as anatomically proximal.

Figure 1:
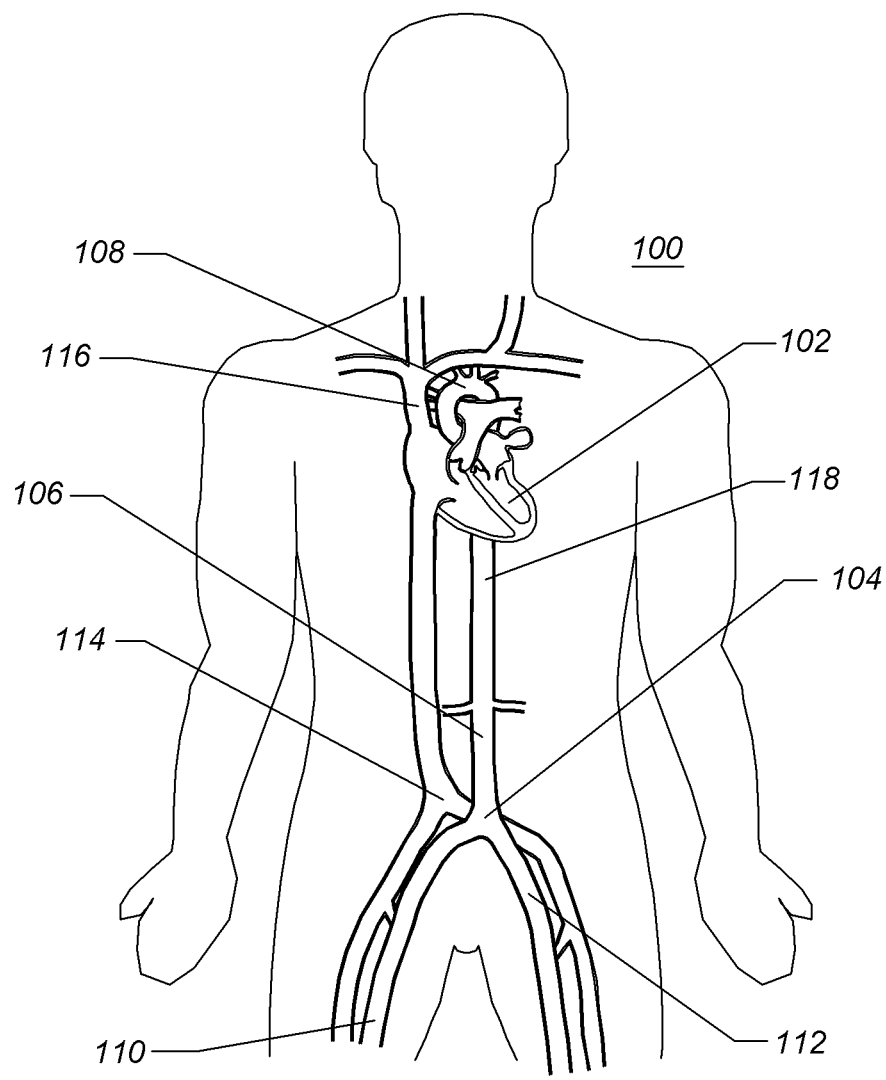
FIG. 1 is a front view schematic representation of the human circulatory system including the heart, the aorta, the iliac and femoral arteries, according to an embodiment of the invention.

FIG. 1 is a schematic frontal (anterior) illustration (looking posteriorly) of a human patient 100 that illustrates components of the central circulation. As shown, the central circulation generally includes a heart 102, an aortic bifurcation 104, a descending aorta 106, an aortic arch 108, an inferior vena cava 114, a superior vena cava 116, an iliac artery 112, a femoral artery 110, and a thoracic aorta 118. In this illustration, the left anatomical side of the body of the patient 100 is toward the right of the illustration. FIG. 1 primarily illustrates components of the central circulation.

Referring to FIG. 1, the heart 102 is a pump, the outlet of which is the aorta, including the aortic arch 108, the thoracic aorta 118, the descending aorta 106, and the aortic bifurcation 104, which include the primary artery in the systemic circulation. The circulatory system, which is operably connected to the heart 102 further includes the return, or venous, circulation. The venous circulation includes the superior vena cava 116 and the inferior vena cava 114, which return blood from the upper extremities and lower extremities, respectively. The iliac arteries 112 are operably connected to, and receive blood from, the aortic bifurcation 104. The femoral arteries 110, are operably connected to, and receive blood from, the iliac arteries 112. The veins, which terminate in the superior vena cava 116 and the inferior vena cava 114, carry blood from the tissues of the body back to the right heart, which then pumps the blood through the lungs and back into the left heart. Pressures within the venous circulation generally average 20 mm Hg or less. The arteries of the circulatory system carry oxygenated blood (not shown) from the left ventricle of the heart 102 to the tissues of the body 100. The pressures within the aorta undulate, with a modified triangle waveform, between diastolic pressures of around 80 mm Hg to a systolic pressure of around 120 mm Hg. A hypotensive person may have arterial pressure lower than 120/80 mm Hg and a hypertensive person may have arterial pressures higher than 120/80 mm Hg. Systolic arterial pressures of about 300 mm Hg, or greater, can occur in extremely hypertensive persons.

Figure 2:
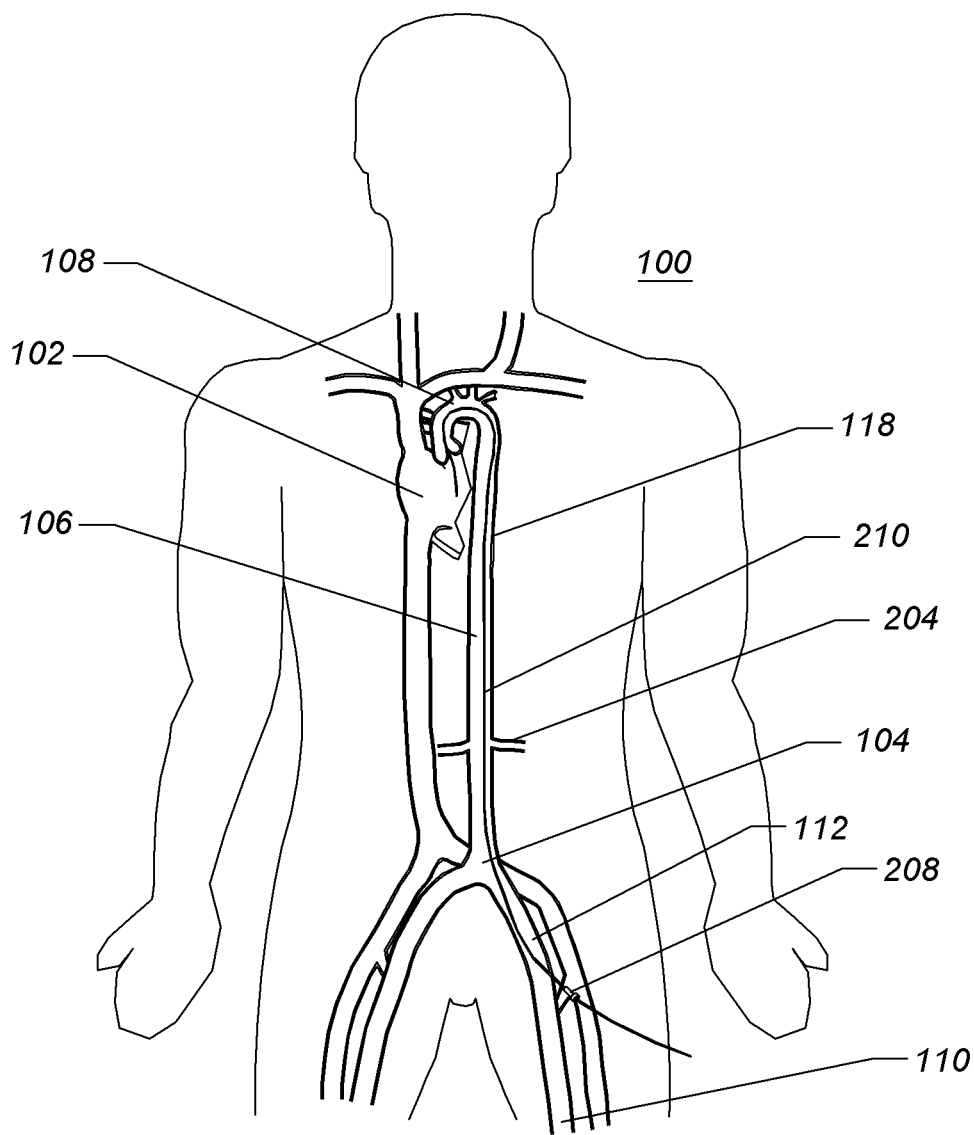
FIG. 2 is a front view schematic representation of the human circulatory system with a guidewire routed from the iliac artery into the aorta, according to an embodiment of the invention.

FIG. 2 is a schematic frontal illustration, looking posteriorly from the anterior side, of the patient 100. In this illustration, much of the right ventricle, left ventricle, and left atrium have been cut away to permit visibility of the thoracic aortic structure 118, which lies posterior to the heart 102. A hollow, 18-gauge needle 208 has been inserted into the left iliac artery 112 via a percutaneous puncture or incision. A guidewire 210 has been inserted through the hollow, 18 gauge needle 208 and routed, cranially, through the aortic bifurcation 104, up the descending aorta 106 past the renal arteries 204, through the thoracic aorta 118, and into the aortic arch 108. In this illustration, the left anatomical side of the patient 100 is toward the right. The guidewire 210 has been placed so that it can be used to track therapeutic or diagnostic catheters into a region of the thoracic aorta 118.

Referring to FIG. 2, the central arterial circulation, through which the guidewire 210 has been routed, may range from 60 to over 300 mm Hg depending on the level of hypertension or hypotension existent in the patient. By accessing the heart through the arterial circulation, the chance of hemorrhage from the catheter insertion site can be minimized by use of hemostasis valves built into any catheters, sheaths, hollow needles, or introducers 208 used on the patient. The guidewire 210 can generally be of sufficient length that a portion of it extends outside the body. Thus, the guidewire can be as long as, or longer than, twice the distance to the treatment site in the patient 100. The most commonly used guidewire diameter ranges from 0.032 inches to 0.038 inches or larger for these applications. Guidewires can be PTFE coated to improve lubricity and can have various types of tip configurations including, but not limited to, straight, "J", floppy tip, rigid tip, or the like. Access, in this illustration is gained through the iliac artery 112 but, if the catheters are small enough, the access can be gained through a femoral artery 110. As will be described in more detail below, in some embodiments, access can also be gained through the subclavian artery using a somewhat shorter device.

FIG. 3A illustrates one embodiment of an expandable iliac introduction sheath/dilator assembly 300. In the illustrated embodiment, the assembly 300 includes three distinct regions of expandability distributed along the length of the sheath. As will be explained below, the assembly may have more or less distinct regions of expandability. In some embodiments, the sheath/dilator assembly 300 can include a sheath hub 302 further including a Tuohy-Borst type hemostasis valve 340 (or any other type of suitable hemostasis valve), a dilator hub 304, a proximal non-expandable tubing region 306, a first transition zone 308, a proximal expandable region 310, a central expandable region 312, a distal expandable region 314, a second transition zone 320, a third transition zone 322, a dilator balloon 318, and a length of dilator catheter tubing 316.

Referring to FIG. 3A, the sheath hub 302 can be coupled to the proximal end of the non-expandable tubing region 306. The distal end of the non-expandable tubing region can be coupled to the proximal end of the proximal expandable region 310 by the first transition zone 308. The distal end of the proximal expandable region 310 can be coupled to the central expandable region 312 by the second transition zone 320. The distal end of the central expandable region 312 can be coupled to the proximal end of the distal expandable region 314 by the third transition zone 322. The dilator balloon 422 (FIG. 4C) can be bonded, welded, or otherwise coupled to the dilator catheter tubing 316 by balloon bonds (not shown) at both ends of the dilator balloon 318. In some embodiments, the dilator balloon 422 can be fully deflated and wrapped around the dilator catheter tubing 316 prior to insertion inside the sheath. The dilator hub 304 can be coupled to the proximal end of the dilator catheter tubing 316.

FIG. 3B illustrates the expandable introduction sheath 330 (in an expanded configuration), which can be part of the sheath/dilator system 300, but with the dilator removed. The introduction sheath 330 includes the sheath hub 302, further including the hemostasis valve 340, the proximal non-expandable tubing region 306, the first transition zone 308, the proximal expandable region 310, the central expandable region 312, the distal expandable region 314, the second transition zone 320, and the third transition zone 322.

Referring to FIG. 3B, the expandable introduction sheath 330 can be illustrated with the proximal expandable region 310, the first transition zone 308, the second transition zone 320, the central expandable region 312, the third transition zone 322, and the distal expandable region 314 all having been expanded radially, or diametrically, to a second, larger cross-sectional configuration. Malleable reinforcing structures (not shown), which will be described in more detail below, within the first transition zone 308, the proximal expandable region 310, and the distal expandable region 314 can maintain the sheath in the second, larger, cross-sectional configuration. Preferably, the malleable elements within the proximal expandable region 310 and the distal expandable region 314 can maintain sufficient strength to overcome resilient forces exerted by the polymeric tubing within which the malleable elements can be embedded, but can have insufficient strength to overcome the expansion forces of the dilator balloon 318 of FIG. 3A. The malleable reinforcing elements in the distal expandable region 314 can, in some embodiments, provide similar strength as those reinforcing elements in the proximal expandable region 310. In some embodiments, the distal expandable region 314 can include reinforcing elements that are less strong than those in the proximal expandable region 310. The reinforcing elements can include structures such as, but not limited to, spiral windings of flat or round wire, braided elements of polymeric strands, wire, a mesh structure similar to a stent, a slotted tube with overlapping longitudinally oriented slots, or the like.

The dilator balloon 318 can be fabricated from PET, PETG, polyamide, polyamide, or the like, with wall thickness ranging between 0.001 to 0.006 inches, and can be capable of containing an internal pressure of 10 to 30 atmospheres, or higher. The dilator balloon 318 can be generally filled with incompressible fluid such as, but not limited to, saline, radiographic contrast media, or the like by the operator, through a balloon inflation port integral to, or coupled to, the dilator hub 304.

In some embodiments, the central expandable region 312 can include reinforcing elements similar to those used in the proximal expandable region 310 and the distal expandable region 314. In some embodiments, the central expandable region 312, and the distal expandable region 314 can include shape-memory reinforcing elements that can be heated or cooled to generate austenite or martensite conditions, respectively, that further can be used to drive the sheath wall from one cross-sectional configuration to another.

FIG. 4A illustrates an embodiment of an expandable iliac introducer sheath/dilator assembly 400 having only one region of expandability. The expandable region 408 and the transition zone 406 can illustrated in a first, smaller cross-sectional configuration. The transition zone 406 can form a taper between the diametrically collapsed expandable region 408 and the larger proximal non-expandable region 404. The introducer sheath/dilator assembly 400 of the illustrated embodiment includes a sheath hub 402, a length of proximal non-expandable tubing 404, a transition zone 406, an expandable region 408, the dilator balloon 318, the length of dilator tubing 316, and the dilator hub 304.

Referring to FIG. 4A, the sheath hub 402 can be coupled to the proximal end of the proximal non-expandable tubing 404. The distal end of the proximal non-expandable tubing 404 can be coupled to the proximal end of the expandable region 408 by the transition zone 406. The dilator hub 304, dilator tubing 316, and dilator balloon 422 (FIG. 4C) can be assembled as described in FIG. 3A.

FIG. 4B illustrates the expandable introduction sheath 430, which can be part of the sheath/dilator system 400, but with the dilator removed. The expandable region 408 and the transition zone 406 have been fully expanded to the second, larger, cross-sectional configuration. The introduction sheath 430 includes the sheath hub 402, the proximal non-expandable tubing region 404, the first transition zone 406, and the expandable region 408.

FIG. 4C illustrates a sheath dilator 400 including a dilator shaft 420, the dilator hub 304, the dilator balloon 422, the distal fairing 318, and the sheath distal tubing 316. The dilator balloon 422 includes neck down regions and the dilator balloon can be coupled to the dilator shaft 420 or the dilator hub 304 at the proximal neck down region and to the sheath distal tubing 316 at the distal neck down region using adhesives, welding, or a combination thereof. The dilator balloon 422 can be an angioplasty type balloon fabricated from material such as, but not limited to, PET, polyimide, polyamide, reinforced polymers, or the like. The dilator balloon 422 can be configured to generate pressures ranging up to 25 or 30 atmospheres when filled with pressurized liquids such as, but not limited to, radiopaque dye contrast media, saline, Ringer's lactate, or the like. The dilator balloon 422 includes a flat length at least as long as the combined length of the sheath expandable distal region 408 and the transition zone 406, and can preferably be somewhat longer to facilitate manufacturability and reliability. The dilator balloon 422 can include an inflated diameter approximately equal to or slightly greater than that of the fully expanded distal region 408 of the sheath. The balloon 422 can include wall thicknesses ranging from 0.0005 to 0.005 inches and more preferably ranging between 0.0007 and 0.002 inches. Note that the distal fairing 318, which can be beneficially fabricated from soft elastomeric materials, can expand and fold distally off the shoulders of the balloon 422 such that when the balloon 422 is deflated, the fairing 318 can return to a small diameter that can be withdrawn proximally through the lumen of the sheath 430.

FIG. 5A illustrates an embodiment of a two-way expandable sheath dilator assembly 500 capable of being radially expanded and then radially constricted prior to removal from the patient. The sheath dilator assembly 500 includes the dilator hub 304, the dilator balloon 422, the length of dilator tubing 316, the sheath hub 502, the proximal sheath tubing 504, the transition zone 506, and the expandable sheath region 508.

Referring to FIG. 5A, the sheath hub 502 can be coupled to the proximal end of the proximal sheath tubing 504. The distal end of the proximal sheath tubing 504 can be coupled to the proximal end of the expandable region 508 by the transition zone 506. The dilator hub 304, dilator tubing 316, and dilator balloon 318 can be assembled as described in FIG. 3A.

The expandable region 508, in the illustrated embodiment, can include shape memory elements (not shown) fabricated from nitinol, which can be configured with an austenite finish temperature in excess of body temperature (normally around 37 degrees centigrade). Thus, the expandable region 508 can be heated by application of electricity to generate resistive heating and temperature increase to above the austenite finish temperature. A suitable austenite finish temperature can range from 38 to 50 degrees centigrade. Such heating can be performed at the conclusion of the procedure, following removal of any therapeutic or diagnostic instruments from the center of the sheath. The sheath can generally be within the blood stream and not touching any vascular walls. Furthermore, flowing blood can disperse heat generated by the resistive heating elements so as to minimize localized heating damage effects to the body. The shape memory elements can be heat set to a collapsed, small diameter configuration to which they can be biased following application of resistive heating. The reinforcing structures can be configured as a braid, a spiral winding, a woven mesh, a slotted tube, or the like. The reinforcing structures can be heat set in a collapsed, or small, initial diameter configuration and then be cooled to below martensite finish temperature, at which point the reinforcing structures can be expanded for coating with a polymer or other suitable manufacturing process.

FIG. 5B illustrates the two-way expandable sheath dilator assembly 500 with the dilator balloon 318 fully inflated to expand the sheath radially, or diametrically, outward. The dilator balloon 318 can run the entire length and slightly beyond the extents of the expandable region 508. The sheath dilator assembly 500 further includes the expandable region 508, the transition zone 506, the proximal non-expandable sheath tubing 504, the sheath hub 502, and the length of dilator tubing 316.

FIG. 5C illustrates a two-way expandable sheath 530, which is the sheath/dilator assembly 500 following removal of the dilator. The two-way expandable sheath 530 includes the proximal tubing 504, the hub 502, the transition zone 506, and the expandable region 508. The expandable region 508 is illustrated radially collapsed following removal of the balloon dilator.

Referring to FIG. 5C, the expandable region 508 can re-collapse to a third, smaller cross-sectional configuration by application of heat to the shape-memory reinforcement embedded within the expandable region. The expandable region 508 can be made to uniformly compress to a smaller diameter, or it can be made to fold into any of a variety of cross-sectional patterns exhibited by a tube that is folded along longitudinally disposed folds. In some embodiments, where uniform reduction in cross-sectional shape is imparted, the reinforcement can include a braid that elongates longitudinally when reduced in diameter. The polymeric surround of the expandable region 508 can preferably be elastomeric and includes materials such as, but not limited to, polyurethane, thermoplastic elastomer, silicone elastomer, or the like. The interior of the wall of the expandable region can advantageously be coated with a layer of high lubricity and low friction to facilitate catheter or device introduction therethrough without hang-up.

In some embodiments, the expandable region 508 can be maintained with an open inner lumen if a hollow sleeve or dilator (not shown) is inserted therethrough, or if the expandable region 508 has at least some hoop strength gained by appropriate wall design or reinforcement within the wall. Referring to FIG. 5C, the hollow sleeve or dilator (not shown) can include a hollow axially elongate tube with a proximal end and a distal end. The tube can include structures and materials that impart flexibility to the hollow sleeve or dilator but the tube advantageously includes the properties of column strength and kink-resistance. The proximal end of the tube including the hollow sleeve or dilator can be coupled to a sleeve hub. The structure of the tube comprised by the hollow sleeve or dilator can preferably be very thin and can further include a single material, preferably polymeric, or it can include a built-up, composite structure with a reinforcing layer and a polymeric surround. The reinforcing layer can include a braid, weave, helical coil, slotted tube, or the like. In a preferred embodiment, the hollow sleeve or dilator tube can include polymeric surround materials such as, but not limited to, polyamide, polyamide, polyurethane, polyester, polyether ether ketone, Hytrel, or the like. The length of the hollow sleeve or dilator tube can be sufficient to extend from the proximal end of the sheath hub 502 to the distal end of the expandable region 508. The distal end of the hollow sleeve or dilator tube can include a bevel on the outer surface to assist with coercing the sheath expandable region 508 to expand from the first, smaller cross-sectional area to the second, larger cross-sectional area. The distal end of the hollow sleeve or dilator tube can further include shape-memory elements that can be bent radially inward at the distal end in their martensitic phase and then, upon exposure to body temperature blood, the shape-memory elements can expand radially outward to form a straight, non-inwardly beveled distal end. In some embodiments, an obturator can be provided which closely fits the inside diameter of the hollow sleeve or dilator tube and which includes a tapered distal end suitable for advancement into a body lumen, vessel, or expandable sheath tube. The hollow sleeve or dilator tube can be advanced into the expandable sheath as a unit. The obturator can include a hub at the proximal end that can releasably snap or connect to the distal end of the hollow sleeve or dilator tube hub. Once the composite structure is advanced completely into the expandable sheath, the obturator can be removed, revealing the large central lumen suitable for the introduction of catheters, instruments, implants, or the like.

FIG. 6A illustrates an embodiment of the iliac sheath system 600 including a dilator 400 further including a distal fairing 318, a main dilator tube 330, an optional outer dilator tube (not shown), a dilator balloon 422, a dilator hub 304 further including an inflation port 332, and a sheath 630 further including a proximal sheath tube 604, a transition zone 606, a distal sheath tube 608, and a sheath hub 602. A guidewire 210 can be slidably disposed within an inner lumen of the dilator 400.

Referring to FIG. 6A, the distal fairing 318 can be coupled to the main shaft 330 of the dilator 400 near the distal end. The distal fairing 318 can be fabricated from elastomeric materials such as, but not limited to, thermoplastic elastomer, silicone elastomer, polyurethane elastomer, Hytrel elastomer, or the like. A balloon (not shown) can reside with the flat length disposed along at least the entire distal sheath tube 608 and the transition zone 606. The balloon (not shown) can be coupled to the main shaft 330 of the dilator 400 and the interior of the balloon (not shown) can be operably connected to an annulus running between the main shaft 330 and an external shaft (not shown) or within a lumen of the main shaft 330. The annulus (not shown) or lumen (not shown) can operably extend between the inflation port 332 and a skive, scythe, or port opening into the interior of the balloon (not shown). The balloon (not shown) can preferably be an angioplasty-type non-elastomeric balloon fabricated from material such as, but not limited to, PET, PET copolymers, polyamide, polyimide, reinforced polymers, and the like. The balloon (not shown) can have a wall thickness that can range between approximately 0.0004 and 0.005 inches, and more preferably between 0.001 and 0.002 inches. The ends of the balloon (not shown) can be tapered inward to form shoulders (not shown) that can be bonded, welded, or otherwise coupled to the main shaft 330 at the distal end and either the main shaft 330 or an external shaft (not shown) at the proximal end. The dilator hub 304 can include an inflation port 332 that can be operably connected to the inflation lumen or annulus of the dilator 400. In some embodiments, the proximal end of the dilator balloon 422 (FIG. 4C) can extend proximally all the way to the dilator sidearm or hub 304. In some embodiments, fluid pressure applied to an inflation port on the dilator hub 304 can be operably connected to the annulus between the dilator balloon 422 and the catheter shaft, allowing balloon inflation fluid such as radiopaque dye contrast media, saline, or the like, to be routed into the balloon internal structure and causing the balloon to forcibly expand diametrically. This arrangement can result in a beneficial increase in rated balloon burst, or inflation, pressure. Rated balloon burst pressures in excess of about 25 to 30 atmospheres can be achieved with 99.9% reliability and 95% confidence.

The dilator 400 (FIG. 4C) can be slidably disposed within the central lumen of the sheath 630 and further includes an expandable dilator (not shown) such as, but not limited to, an angioplasty type balloon, malecot, reverse collet, or other device capable of expansion to approximately 0.2-mm (0.5 French), or greater, larger than the diameter of the sheath. The balloon (not shown) can be inflated through the inflation lumen within the catheter shaft, which can be operably connected, at the proximal end, to a dilator hub or inflation port. Following inflation, which expands the distal end of the sheath, the dilator expansion element, such as the balloon (not shown), can be deflated or collapsed, following which it can be removed from the sheath 630 along with the nose cone 318.

The sheath hub 602 can include ports that further include, or can be terminated by, hemostasis valves. The hemostasis valves can be configured to prevent hemorrhage from, or air intake into, the lumen of the sheath 630. The hemostasis valves can include between one and 5 elements to form a seal against nothing inserted into the valve, form a seal against a maximum diameter object inserted through the valve, and form a seal against anything of intermediate size inserted through the valve. The hemostasis valve elements can be fabricated from soft silicone or other elastomer. The hemostasis valve elements can be coated or impregnated with lubricious coatings such as silicone oil or hydrophilic layer. The hemostasis valve elements can include duckbill valves, pinhole valves, slit valves, X-slit valves, ring seals, or the like.

The distal sheath tubing 608 can be folded longitudinally in a carefully predetermined pattern including between one and four exterior fold edges, wherein the folds can extend all the way from the proximal end of the transition zone 606 to the distal end of the distal sheath tube 608. The distal fairing 318 can be configured to cover the distal exposed edge of the distal sheath tube 608 to provide a smooth taper against which the sheath system 600 can be advanced into the vasculature.

FIG. 6B illustrates the iliac sheath 630 following expansion of the distal region 608 and removal of the dilator 400 and the guidewire 316 of FIG. 6A. The proximal sheath tube 604, which can be coupled at the proximal end to the sheath hub 602, can include one or two layers of mesh reinforcement 612 and a spring-coil reinforcement 610. The distal sheath tube 608 and the transition zone 606 can further include a malleable coil 614 and, optionally, the mesh reinforcement 612. The entire sheath tube, which includes a central lumen (not shown), includes an approximately constant inner diameter along the entire length. The approximately constant diameter is beneficial in that objects of large diameter can be inserted and advanced completely from the proximal end and out the distal end of the sheath 630. The sheath 630 is illustrated in partial breakaway view to show the coil reinforcement layers 610 and 614 along with the mesh 610.

In some embodiments, an inner sheath layer 634 can be first laid down over a PTFE-coated stainless steel mandrel (not shown). The sheath inner layer 634 can be preferably fabricated from lubricious materials such as, but not limited to, polyethylene, HDPE, LDPE, blends of HDPE and LDPE, PTFE, FEP, PFA, Hytrel, Pebax, or the like. The sheath inner layer 634 can also be coated, on the inner surface, with friction retarding materials such as, but not limited to, silicone oil, polyurethane-based hydrophilic slip coating materials, or the like. The optional mesh layer 612 can next be applied over the inner layer 634. The coil reinforcement layers 610 and 614 can next be applied over the mesh 612. In some embodiments, a second layer of mesh can optionally be applied over the coil 614. The second layer of mesh can have different properties from the inner layer of mesh, including different filament diameter, filament count, number of picks, and filament density or angle. Finally, an outer layer 632 of polymeric material can be applied over the reinforcement, after which shrink tubing can be placed around the entire structure and can be heated to shrink, melt, fuse, and bond the inner layer to the outer layer while sandwiching the reinforcing layers therebetween. The sheath inner layer 634 can have a wall thickness ranging between about 0.001 and 0.010 inches with a preferred range of about 0.002 and 0.006 inches. The sheath outer layer 632 can have a wall thickness ranging between about 0.001 and 0.010 inches with a preferred range of about 0.001 to 0.006 inches.

The mesh 612 can be formed from a braid, weave, knit or other structure formed into a tubular cross-section. The mesh 612 can be fabricated from flat or round strands. The mesh 612 can be fabricated from polymers such as, but not limited to, polyethylene naphthalate (PEN), PET, polyamide, polyimide, or the like. The mesh 612 can also be fabricated from metals such as, but not limited to, malleable stainless steel, spring stainless steel, nitinol, titanium, cobalt nickel alloy, tantalum, gold, platinum, platinum alloy, and the like. The lateral size of the strands of the mesh 612 can range between 0.001 and 0.010 inches in at least one dimension. The number of ends of the mesh can range between 2 and 50.

The construction of the distal sheath tube 608 can include a coil of wire 614 with a wire diameter of 0.001 to 0.040 inches in diameter and preferably between 0.002 and 0.010 inches in diameter. The coil 614 can also include a ribbon wire or a flat wire that can be 0.001 to 0.010 inches in one dimension and 0.004 to 0.040 inches in the other dimension. Preferably, the flat wire can be 0.001 to 0.005 inches in the small dimension, generally oriented in the radial direction of the coil, and 0.005 to 0.020 inches in width, oriented perpendicular to the radial direction of the coil. The pitch of the coil 614, which is related to the spacing between coil turns, can range from about 0 to about 5 times the ribbon width or wire diameter. Preferably, some space exists between the coil turns to permit bonding between the outer layer 632 and the inner layer 634 so a preferred spacing can be between 0.5 and 4 times the width of the ribbon. The outer layer 632 of polymeric material can have a wall thickness of 0.001 to 0.020 inches and the inner layer 614 has a wall thickness of between 0.001 and 0.010 inches. The wire used to fabricate the coil 614 can be fabricated from annealed materials such as, but not limited to, gold, stainless steel, titanium, tantalum, nickel-titanium alloy, cobalt nickel alloy, or the like. The wire can preferably be fully annealed. The wires can also include polymers or non-metallic materials such as, but not limited to, PET, PEN, polyamide, polycarbonate, glass-filled polycarbonate, carbon fibers, or the like. The wires of the coil reinforcement can be advantageously coated with materials that have increased radiopacity to allow for improved visibility under fluoroscopy or X-ray visualization. The radiopaque coatings for the coil reinforcement may include gold, platinum, tantalum, platinum-iridium, or the like. The mechanical properties of the coil can be such that the coil is able to control the configuration of the fused inner layer 634 and the outer layer 632.

When the distal region 608 is folded (see description below with reference to FIGS. 14A and 14B) to form a small diameter, the polymeric layers 634, 632, which can have some memory, do not generate significant or substantial springback. The sheath wall can preferably be thin so that any forces it imparts to the tubular structure can be exceeded by those forces exerted by the malleable distal reinforcing layers 614, 632. Additionally, a peel away, slide away, or otherwise removable protective sleeve (not shown) can be useful, but not necessary, to maintain the collapsed sheath configuration.

FIG. 6C illustrates the sheath 630 having been expanded diametrically in a prior step, with a prosthetic heart valve delivery catheter 622 shaft inserted therethrough. A prosthetic heart valve 620 can be coupled to the delivery catheter shaft 622 near or at the distal end of the catheter shaft 622. The delivery catheter shaft 622 further includes a hub 624, which can be coupled to the proximal end of the delivery catheter shaft 622, and a balloon inflation sidearm port 626. The central port, at the proximal end of the hub, can preferably be terminated by, or includes, a hemostasis valve. The hemostasis valve can be configured to prevent hemorrhage from, or air intake into, the valve delivery catheter.

It should be appreciated that modifications thereof can be used to provide an expandable region of the catheter with an initial small cross-sectional diameter. By unfolding the distal region 1400, the diameter of the distal region is increased to a larger diameter. In the smaller folded configuration, the malleable structures described above can maintain the distal region in the smaller folded configuration. In some embodiments, an external structure can maintain the sheath in the folded configuration. In this smaller folded configuration it has been noted that the flexibility of the catheter (e.g., the ability of the catheter to navigate the aortic arch) can be increased. When the catheter is unfolded and expanded, the malleable structure can reform to the larger unfolded diameter and to the shape of the anatomy (e.g., the aortic arch) in which the sheath his placed. In the unfolded configuration, the malleable structures can provide hoop strength to maintain the patency of the lumen.

In some embodiments, the exterior of the sheath, and optionally the internal lumen of the sheath, can be coated with a lubricious coating including materials such as, but not limited to, silicone oil or a hydrophilic hydrogel including polyethylene glycol, polyether polyurethane, or the like. Other coatings can include antimicrobial coatings such as those fabricated from silver azide or anticoagulant coatings such as those including heparin.

In the illustrated embodiment of FIG. 6C, the prosthetic valve delivery catheter 622 can be configured to deliver the collapsed prosthetic valve 620 to an implantation site within the patient. Typical valves include aortic and mitral valve replacements. The prosthetic valve 620 further includes an expandable stent support and fixation elements. The valving element can be suspended within, or around, the expandable stent and can include between one and four leaflets fabricated from polyurethane, cross-linked pericardium, fixed natural porcine aortic roots, or homografts. The outside diameter of the collapsed prosthetic valve 620 can be such that the valve 620 can be slidably advanced through the lumen of the sheath 630. In some embodiments, the valve delivery catheter can include an external sleeve to retain the valve 620 in the smallest possible diameter during placement into the patient. The expandable stent support can be malleable and balloon expandable, self-expanding, or self expanding with balloon expansion augmentation.

Figure 7:
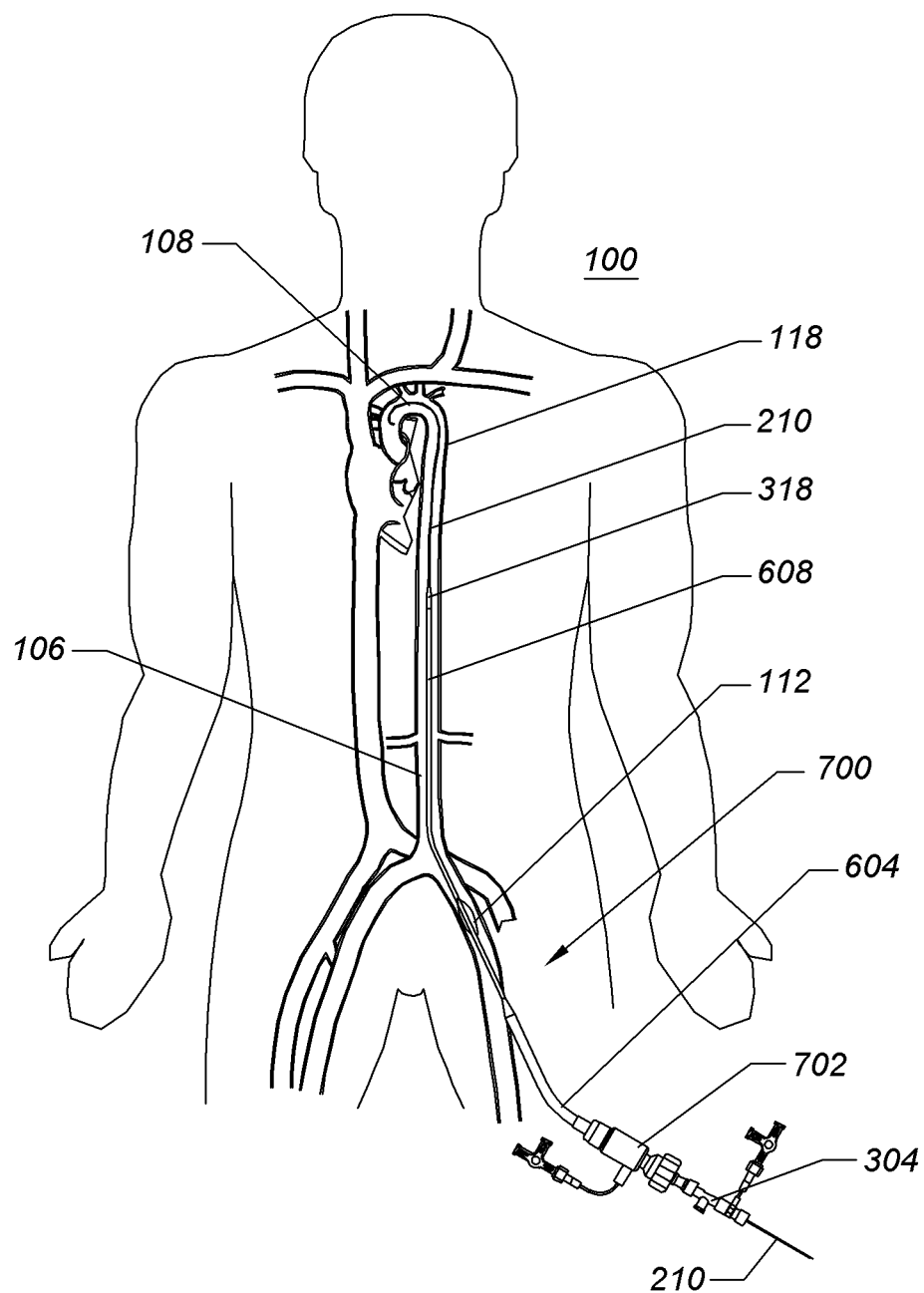
FIG. 7 illustrates an expandable introducer sheath advanced into the iliac artery of a patient in a first, radially collapsed configuration, according to an embodiment of the invention.

FIG. 7 illustrates an expandable iliac sheath 700 having been inserted into the femoral artery 112 of a patient 100. The expandable iliac sheath 700 includes the proximal sheath tube 604, the distal sheath tube 608, the sheath hub 702, a dilator further including a dilator hub 304, the dilator nose fairing 318, and a guidewire 210. The patient 100 further includes the descending aorta 106, and the aortic arch 108.

Referring to FIG. 7, the sheath hub 702 can be a single lumen hub with a large hemostasis valve and a purge port. The sheath hub 702 can be coupled to the proximal end of the proximal sheath tubing 604. In the illustrated embodiment, the distal end of the distal sheath tube 608 can be advanced at least past the aortic bifurcation and can be advanced as far as across the aortic arch 108 and just downstream of, or through, the aortic valve. The distal sheath tube 608 and the dilator expandable component (not shown), compressed within the distal sheath tube 608 are in the first, small diameter configuration to permit maximum flexibility and minimum profile, for negotiating the vasculature.

Figure 8:
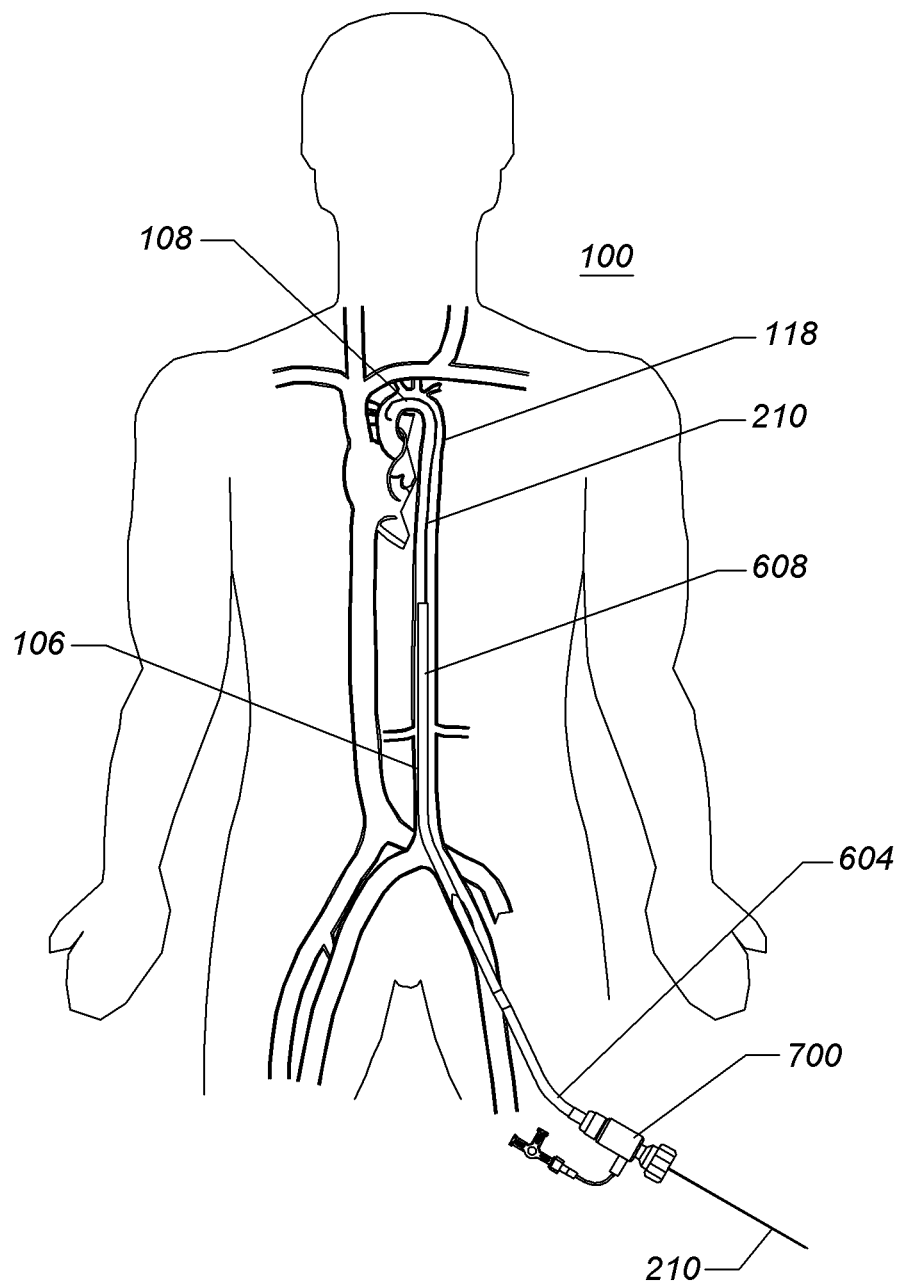
FIG. 8 illustrates an expandable introducer sheath having been dilated within the iliac artery of a patient, according to an embodiment of the invention.

FIG. 8 illustrates that the expandable iliac sheath 700 can have the distal tubing 608 diametrically expanded by the dilator, which can be removed to reveal the large, through working lumen. The expandable iliac sheath 700 includes the proximal sheath tube 604, the now dilated distal sheath tube 608, and a guidewire 210. The patient 100 further includes the thoracic aorta 118, the descending aorta 106, and the aortic arch 108.

Referring to FIG. 8, the guidewire 210 can remain in place or can be withdrawn at this time, if appropriate to the procedure. The expanded sheath can be inserted as shown or can be beneficially advanced so that the distal end is just downstream of the aortic valve.

Figure 9:
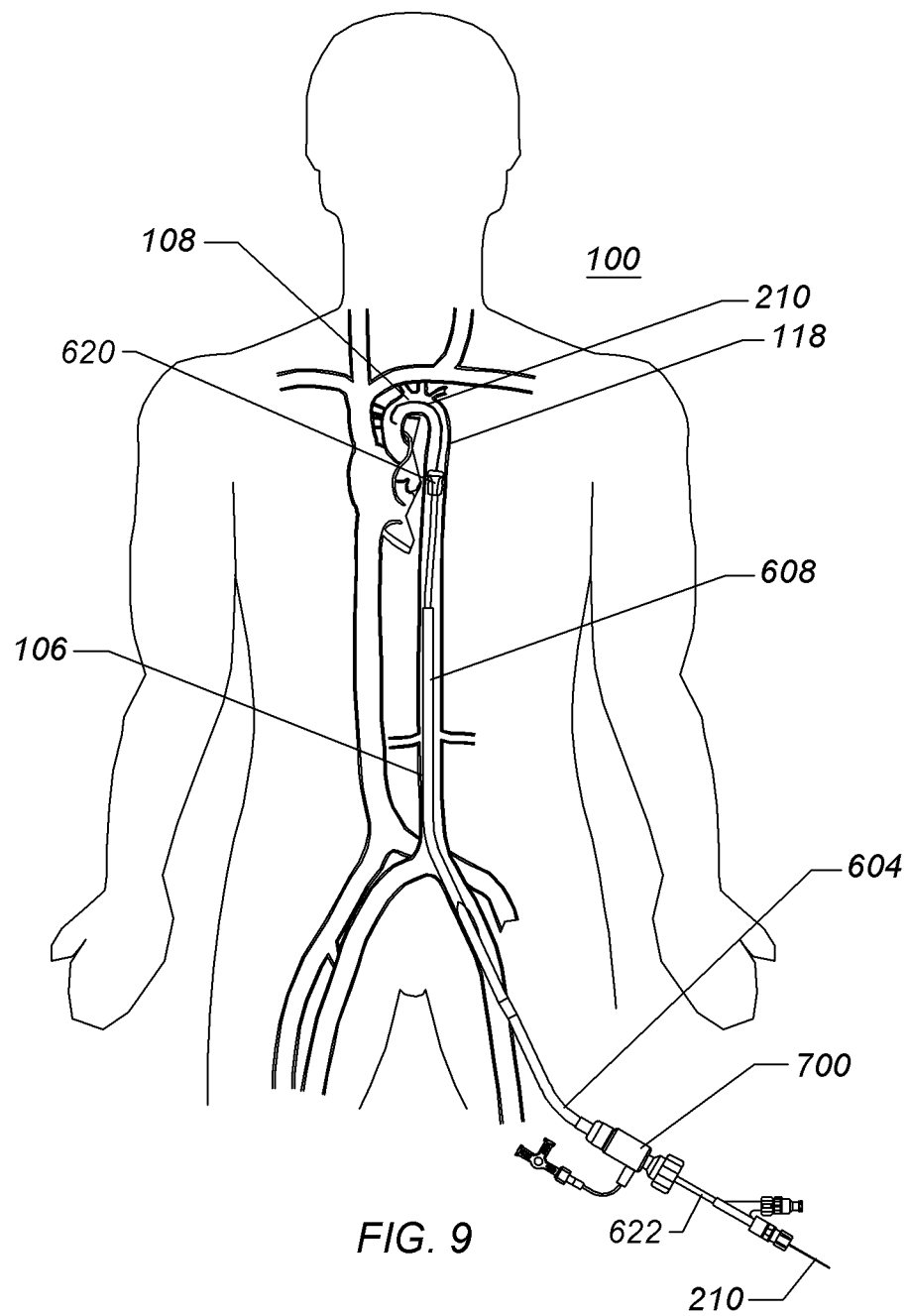
FIG. 9 illustrates a prosthetic aortic valve delivery catheter advanced through the expanded introducer sheath of FIG. 6B, according to an embodiment of the invention.

FIG. 9 illustrates the expandable iliac sheath 700 with an aortic valve delivery catheter 622 and prosthetic aortic valve 620 having been advanced therethrough. The guidewire 210 can remain in place but can be removed, if desired. The prosthetic aortic valve 620 can be advanced toward the natural aortic root (not shown) 1022 and can be implanted therein.

FIG. 9 illustrates an embodiment in which the distal end of the sheath is shown in the thoracic aorta 118 but is beneficially located in the aortic arch 108 or proximate the aortic valve root 1022 for ease of delivery of the aortic valve prosthesis 620. The aortic valve delivery catheter 622 can include a dilatation balloon to expand the aortic valve prosthesis 620, dilate the diseased natural aortic root 1022, and firmly implant the prosthesis 620 within the natural diseased aortic root 1022. Following implantation of the prosthesis 620, a release mechanism, including the catheter 622, can be activated to detach the prosthesis 620 so the catheter 622 and the sheath 700 can be removed from the patient. A hemostasis sheath (not shown) can be advanced into the incision in the iliac artery to minimize loss of blood and stabilize the patient during the immediate postoperative period. The hemostasis sheath (not shown) can include a catheter tube approximating the diameter of the proximal sheath tubing 604 along with a hemostasis valve to prevent unwanted blood loss.

The hemostasis sheath (not shown), the guidewire 210, and the sheath 700 can be provided in a kit, or packaged together for the convenience of the user. All components can be sterilized using ethylene oxide or radiation sterilization, the latter at dosages of, for example, about 25 to 40 kGray. The components of the kit can be packaged in a single aseptic or double aseptic packaging system.

Figure 10:
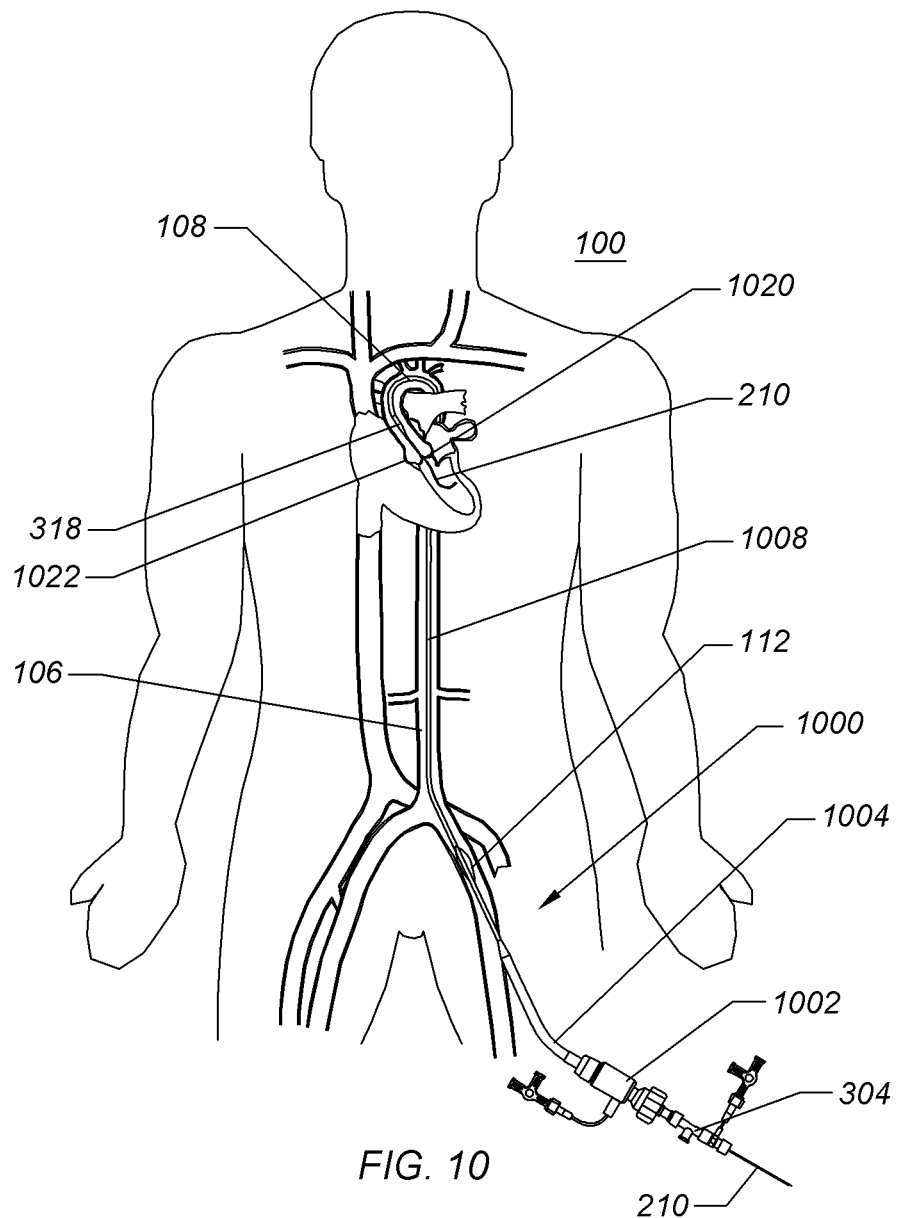
FIG. 10 illustrates a diametrically collapsed aortic sheath inserted into an iliac artery and then routed around the aortic arch and positioned within the aortic root, according to an embodiment of the invention.

FIG. 10 illustrates an aortic sheath 1000 inserted into an iliac artery and then routed, with the expandable distal end 1008 in the diametrically collapsed configuration, around the aortic arch 108 and positioned just distal to the aortic valve 1020. The natural aortic valve 1020 is situated within the aortic root 1022, the aortic root 1022 further including three sinuses of Valsalva. The heart is illustrated in partial cross-section. The guidewire 210 can extend through the aortic valve 1020 and into the left ventricle.

Referring to FIG. 10, the aortic sheath 1000 can be configured to reach from a femoral or iliac artery 112 access site to the left ventricle of the heart. The proximal non-expandable region 1004 can be maintained in position outside the patient 100 or it can be inserted into the femoral or iliac artery. The small diameter of the distal expandable region 1008 can result in a highly flexible configuration that is resistant to kinking because the internal lumen is filled with the dilator. This configuration can be routed around the aortic arch much more easily than another catheter having a larger diameter, similar to that of the proximal region of the catheter. The distal fairing, or nose cone 318, which can be coupled to the dilator, can be situated just distal to the aortic valve.

Figure 11:
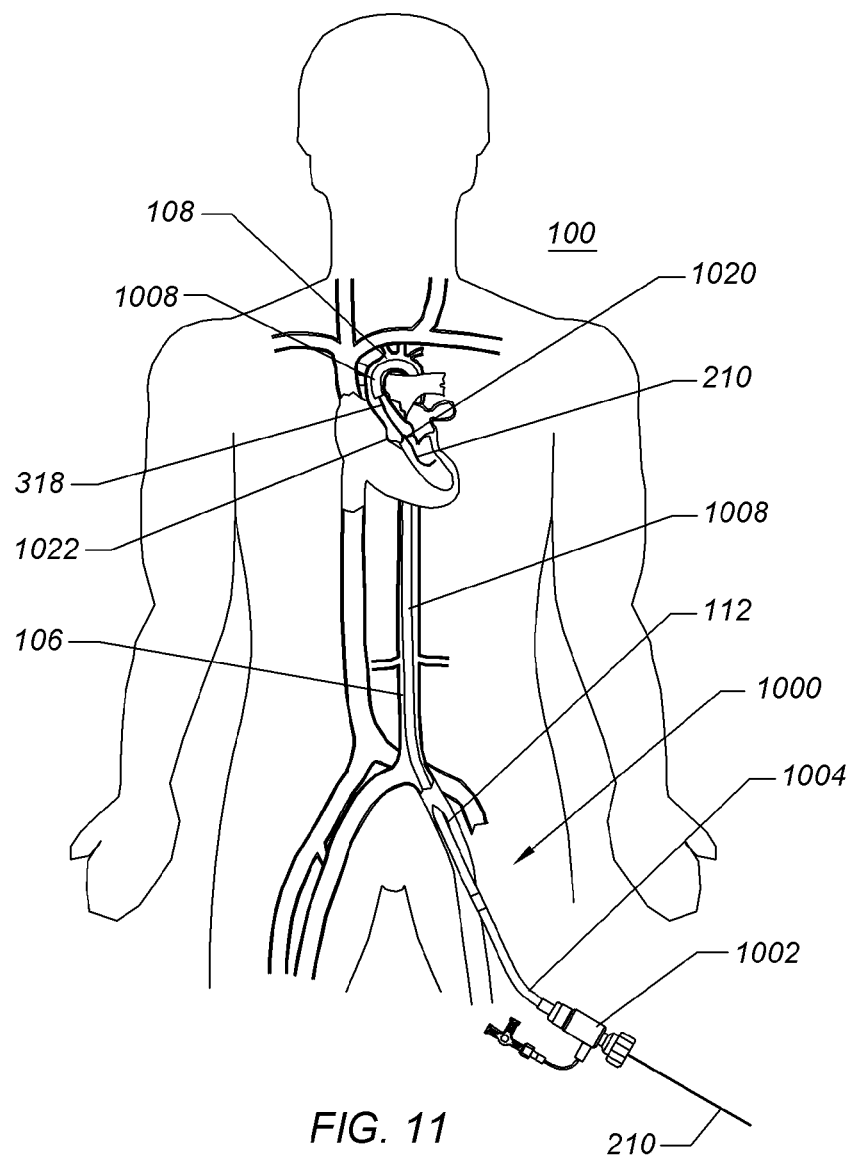
FIG. 11 illustrates the aortic sheath of FIG. 10 which has had an expandable distal region expanded by the dilator, following which the dilator has been removed, according to an embodiment of the invention.

FIG. 11 illustrates the patient 100 wherein the sheath 1000 has had the expandable distal region 1008 expanded by the dilator system, following which the dilator system 400 (Refer to FIG. 4C), further including the dilator hub 304, has been removed. The central lumen (not shown) of the sheath 1000 includes a relatively large, constant diameter from the distal end to the proximal end of the sheath hub 1002. The distal end of the sheath 1000 can be situated within the aortic outflow tract, proximate the aortic root, with the sheath 1000 having fully traversed the aorta and aortic arch 108. In some embodiments, the distal region 1008 can be routed through the aortic arch and then expanded to remodel the walls of the expandable distal portion 1008 of the sheath 1000. In the remodeled configuration, the distal expandable region 1008 can exhibit greater stiffness, reduced flexibility, greater diameter, and greater torqueability than the distal expandable region 1008 in the unexpanded configuration, as illustrated in FIG. 10. The remodeling generally is preferable to elastic deformation that can cause the distal region 1008 of the sheath to spring or bias itself straight, since the remodeling can result in a sheath that generally takes on the curve to which it is pre-set prior to expansion and to which the distal region 1008 is exposed during the expansion procedure. The remodeling condition can occur because balloon dilatation forces cause the plastic walls of the distal end 1008 of the sheath 1000 to plastically flow to their new configuration prior to removal of the dilator. The reinforcement within the distal, expandable region 1008 preferably does not substantially contribute to bending forces on the expanded distal section 1008.

Figure 12:
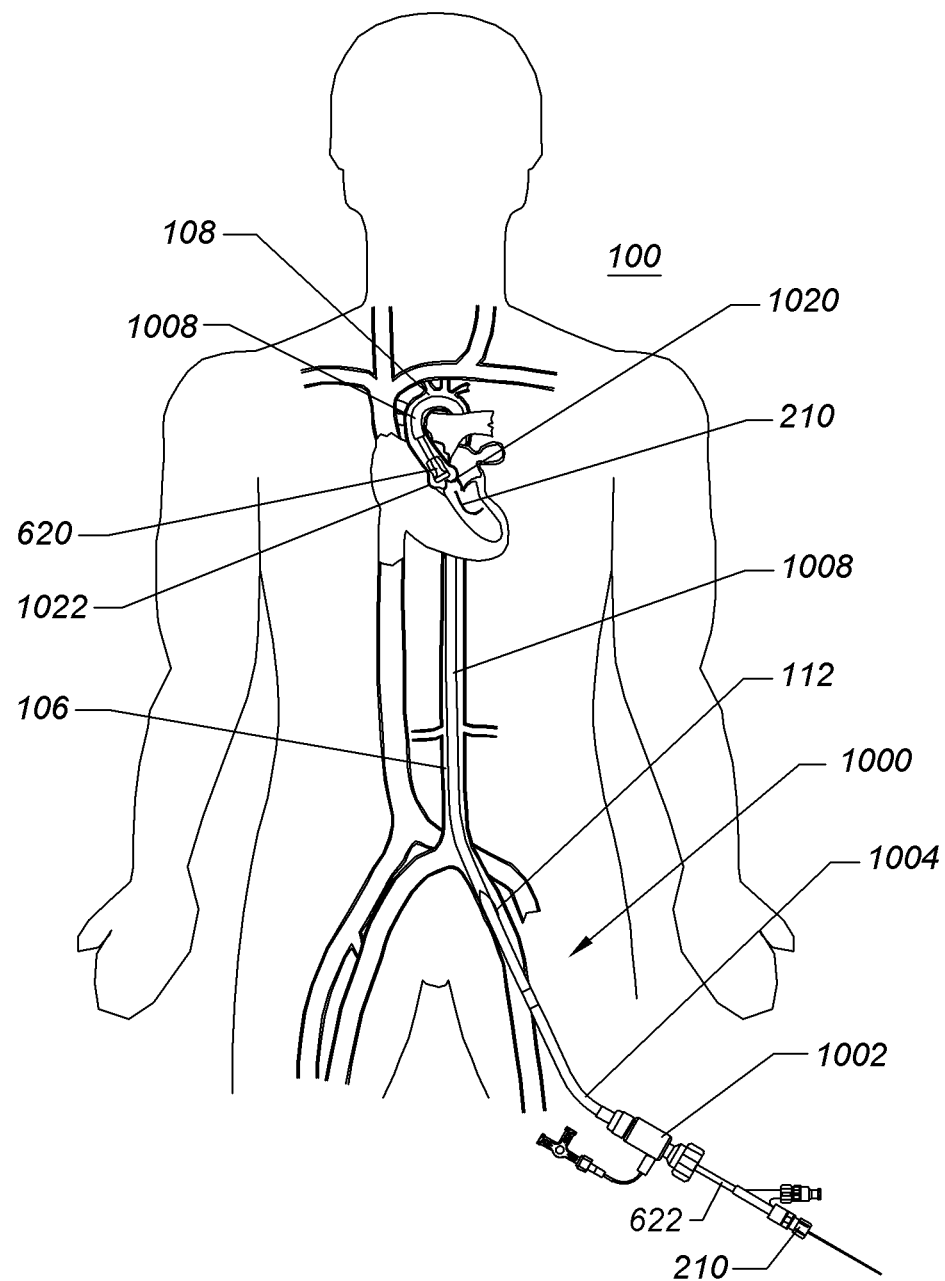
FIG. 12 illustrates a prosthetic aortic heart valve replacement being placed through the sheath of FIG. 10 by means of a catheter introducer, according to an embodiment of the invention.

FIG. 12 illustrates the patient 100 wherein a prosthetic aortic heart valve replacement 620 is placed through the sheath 1000 by means of a catheter valve introducer 622. The catheter valve introducer 622 can be placed through a hemostasis valve 1002 coupled at or near the proximal end of the sheath 1000. The sheath 1000 can facilitate introduction of the prosthetic valve 620 as well as the removal, should that become necessary. The guidewire 210 can remain in place as a safety wire or it can be removed during this part of the procedure. The distal expandable region 1008 of the sheath 1000 can be fully expanded, can be relatively rigid compared to the collapsed configuration as illustrated in FIG. 10, and can be less capable of being advanced through tortuous vasculature than when it is in the un-dilated state.

Figure 13:
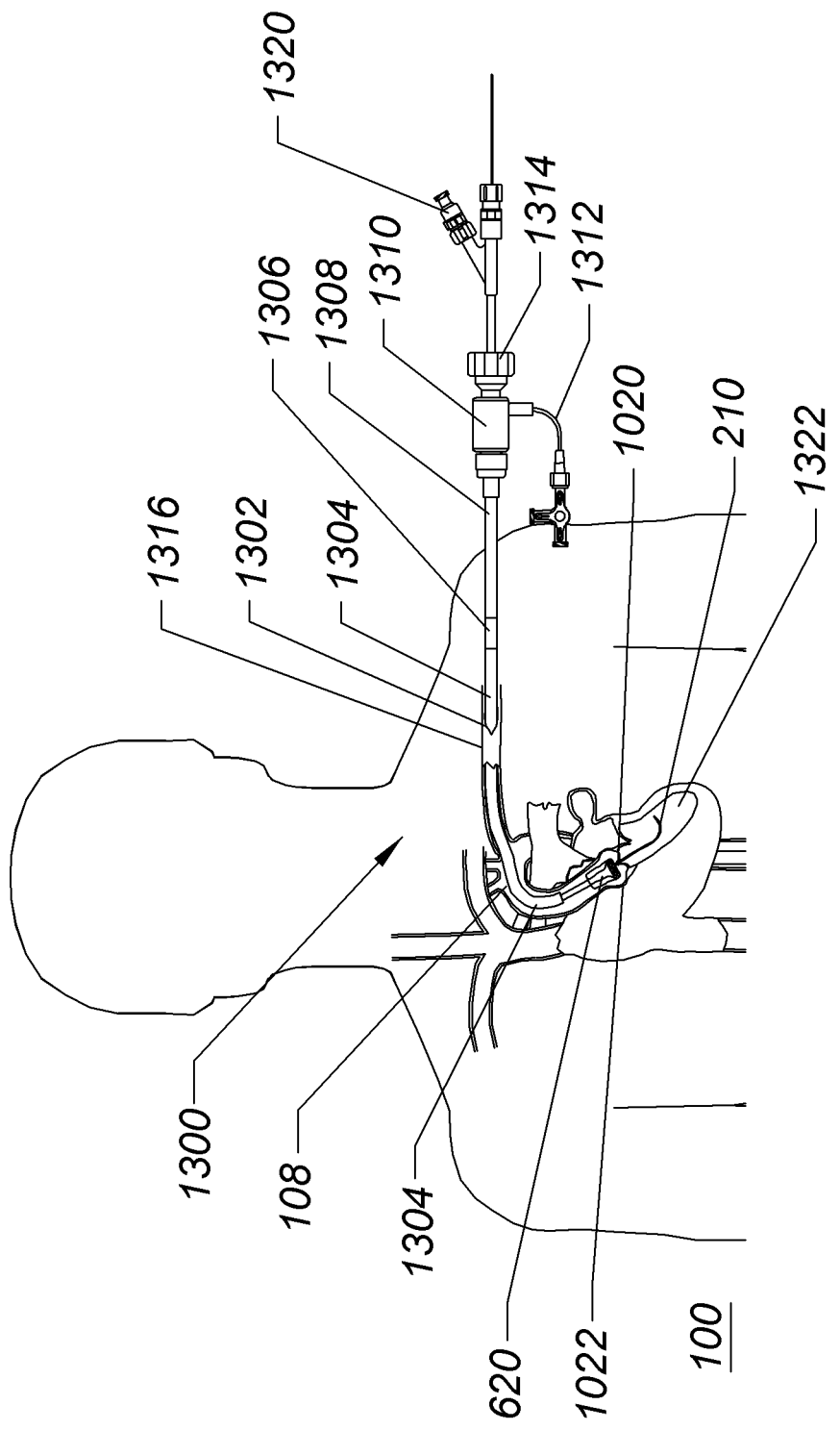
FIG. 13 illustrates a prosthetic aortic heart valve replacement being placed through a subclavian artery access sheath, according to an embodiment of the invention.

FIG. 13 illustrates an expandable arterial access sheath 1300 being used to access the arterial vasculature through the left subclavian artery 1316 of a human patient 100. The expandable arterial access sheath 1300 enters the subclavian artery 1316 at the arterial access site 1302. The sheath 1300 includes the expandable distal region 1304, the transition zone 1306, the proximal, non-expandable region 1308, the sheath hub 1310, and the sheath hemostasis valve 1314. The sheath 1300 can be used to guide a valve delivery catheter 1320 to the aortic outflow tract 1022 through the aortic arch 108 and proximate the natural aortic valve 1020. A guidewire 210 is illustrated passing through the central lumen (not shown) of the valve delivery catheter 1320 with the distal end of the guidewire 210 extending through the natural aortic valve 1020 and into the left ventricle 1322. The valve delivery catheter 1320 can be used to deliver, in retrograde fashion, a prosthetic aortic valve 620, which is in the diametrically collapsed, first configuration.

Referring to FIG. 13, the subclavian access configuration of the expandable arterial access sheath 1300 can be shorter than a trans-femoral device with a working length that can range between 25 and 50 cm. The same diameters and construction techniques used for other devices described herein can be suitable for use in the expandable subclavian access sheath 1300. It is generally advantageous that the expandable distal region 1304 is inserted into the arterial access site 1302 and advanced to a region just downstream of, or through, the natural, diseased or damaged aortic valve 1020. The transition zone 1306 and the proximal, non-expandable region can advantageously reside outside the body for the duration of the procedure such that no sheath axial translation can occur after the expandable distal region 1304 has been dilated or expanded.

Figure 14A:
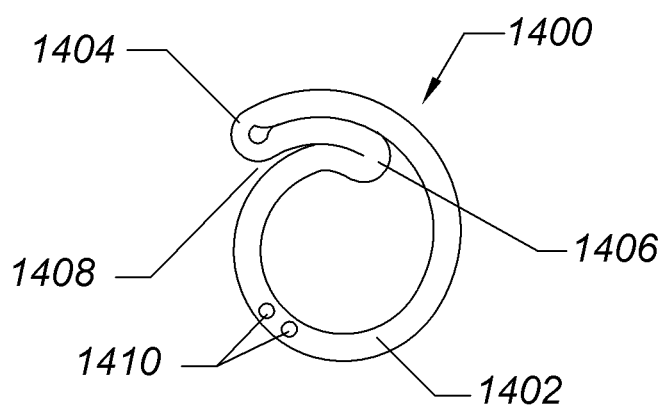
FIG. 14A illustrates a lateral cross-section of a distal region of an expandable arterial sheath including a single fold, according to an embodiment of the invention.

FIG. 14A illustrates a lateral cross-section view of a distal region 1400 of an expandable arterial sheath including a wall 1402, a single longitudinally extending fold 1408 further including an outside edge 1404 and an inside edge 1406, and a plurality of electrical conductors running axially through the wall 1402. With a small diameter distal section 1400 and a relatively thick wall 1402, a single fold 1408 is the one structure to create during manufacturing. The sheath wall 1402 further includes an optional electrical bus 1412 fabricated from stainless steel, silver, copper, or other conductor metal for use in transmitting electrical energy from the sheath hub (not shown) to distal regions of the sheath for purposes such as resistive heating, steering, or the like.

Figure 14B:
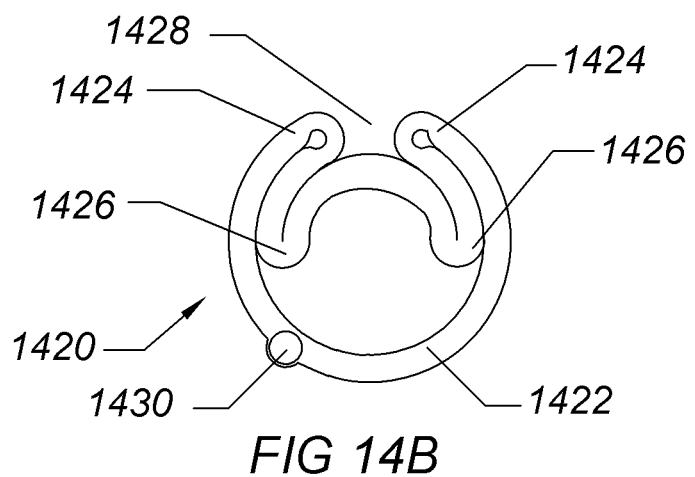
FIG. 14B illustrates a lateral cross-section of a distal region of an expandable arterial sheath including a double fold, according to an embodiment of the invention.

FIG. 14B illustrates another embodiment of a lateral cross-section of a distal region 1420 of an expandable arterial sheath including a wall 1422 further including a double longitudinally extending fold 1428. The double fold 1428 further includes two outside edges 1424 and two inside edges 1426 which form longitudinal creases in the wall 1422. When the diameter of the sheath increases, it can advantageously form a plurality of folds in the wall 1422. For a sheath having a fully expanded outside diameter ranging between 12 French and 30 French and with a wall thickness ranging between 1 and 2-French, a double fold, as illustrated in FIG. 14B can be preferred. A double fold, for example, can allow a 14 French outside diameter sheath to fold into a collapsed diameter of around 9 to 12 French. An 18-French outside diameter sheath having a 1 to 2-French wall thickness can be folded into a collapsed diameter of around 12 to 13 French using a double fold. The sheath wall 1422 further includes an optional balloon inflation lumen 1430 for use in transmitting fluidic pressure or energy from the sheath hub to distal regions of the sheath wherein a balloon may be coupled. The diameter of the balloon inflation lumen 1430 can range between 0.005 to 0.025 inches. In some embodiments, the number of folds can range in number between 3 and 10.

It should be appreciated in the embodiments described above that the longitudinal folds of FIGS. 14A and 14B or modifications thereof can be used to provide an expandable region of the catheter (see embodiments of FIGS. 3A-13) with an initial small cross-sectional diameter. By unfolding the distal region 1400, the diameter of the distal region can be increased to a larger diameter. In the smaller folded configuration, the malleable structures described above can maintain the distal region in the smaller folded configuration. In other embodiments, an external structure can maintain the sheath in the folded configuration. In this smaller folded configuration it has been noted that the flexibility of the catheter (e.g., the ability of the catheter to navigate the aortic arch) is increased. When the catheter is unfolded and expanded, the malleable structure can reform to the larger unfolded diameter and to the shape of the anatomy (e.g., the aortic arch) in which the sheath is placed. In the unfolded configuration, the malleable structures can provide hoop strength and maintain the patency of the lumen.

Figure 15:
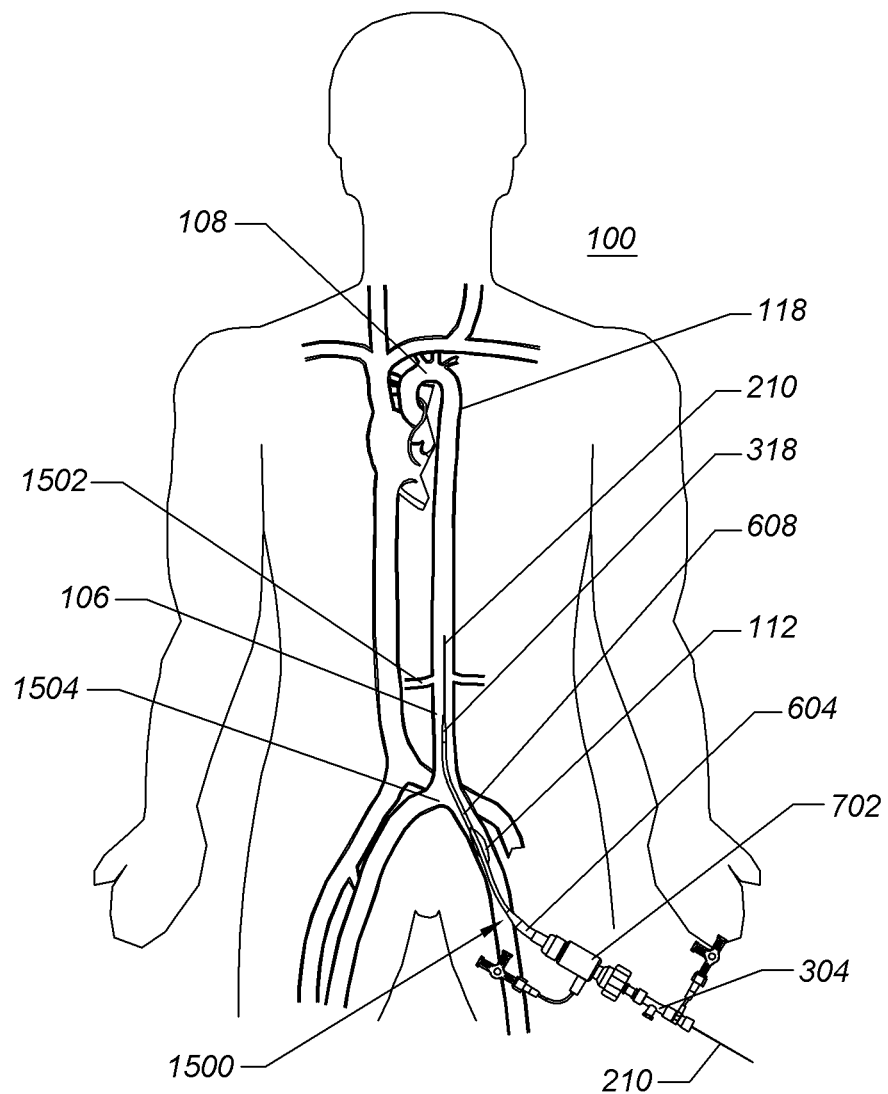
FIG. 15 illustrates a short, expandable iliofemoral introducer sheath advanced into the aorta just proximal to the aortic bifurcation in a patient in a first, radially collapsed configuration, according to an embodiment of the invention.

FIG. 15 illustrates a short, expandable iliofemoral introducer sheath 1500 advanced over a guidewire 210, through a percutaneous access site 112, into the abdominal aorta 106 just proximal to the aortic bifurcation 1504 in a patient 100 in the first, radially collapsed configuration. The iliofemoral introducer sheath 1500 includes a sheath hub 702, a short length of non-collapsible proximal sheath tubing 604, a distal collapsible region 608, a dilator 304, and a distal nose cone or fairing 318. In some embodiments, the distal fairing 318 can reside anatomically distal to the renal arteries 1502 but not be advanced as far as the aortic arch 108 or even the thoracic aorta 118.

The introducer sheath 1500 can be radially expanded by pressurizing the dilator 304 through a balloon inflation port on the dilator 304, in the distal region 608 such that the internal lumen of the distal region 608 can be similar to, or substantially the same as, that of the non-expandable proximal region 604. The dilator 304 can next be removed leaving the large internal lumen within the introducer sheath 1500 for placement of catheters into the aorta. Such catheters can include, but are not limited to, PTCA catheters, stent delivery catheters, prosthetic heart valve delivery catheters, abdominal aortic stent graft delivery catheters, thoracic aorta stent-graft delivery catheters, or the like.

FIG. 16a illustrates a short, expandable, re-collapsible iliofemoral introducer sheath and dilator system 1600 in the first, radially collapsed configuration. The re-collapsible introducer sheath 1600 includes a sheath hub 1602 further including a sheath collapse port 1616, a dilator 304 further including a dilator balloon 318 and a length of dilator tubing 316, a proximal, non-collapsible sheath tube 1604, a transition zone 1606, a distal collapsible region 1608 further including at least one longitudinal fold 1614, an outer pressurization jacket 1610 and an outer pressurization jacket to sheath bond 1612.

Referring to FIG. 16a, the sheath and dilator system 1600 can be similar to the device illustrated in FIG. 6 except for the presence of the external pressurization jacket 1610, which can be coupled and sealed to the sheath tubing 1604 and 1608 at the proximal and distal ends, respectively. A lumen (not shown) can operably connect the collapse port 1616 to the gap between the outer pressurization jacket 1610 and the sheath tubing 1608. The proximal end of the external pressurization jacket 1610 can preferably be coupled to the sheath tubing in the proximal non-collapsible region 1604 or the transition zone 1606. The external pressurization jacket 1610 can also be operably connected to, or coupled to the sheath hub 1602 such that an annulus lumen can exist between the inside of the jacket 1610 and the outside of the sheath tubing 1604, 1606 allowing pressurized fluid to flow to and from the gap between the jacket 1610 and the sheath tubing 1608, 1606. The pressurization jacket 1610 can be fabricated from foldable materials that can be substantially non-distensible or non-elastic such as, but not limited to, polyester, polyimide, polyamide, irradiated polyethylene, or the like. The wall thickness of the outer jacket 1610 can range between 0.0002 inches and 0.005 inches with a preferred wall thickness range of 0.004 and 0.0015 inches. Such structures for the pressurization jacket 1610 can be substantially size constrained or limited and do not expand excessively in their exterior dimensions.

In some embodiments, the outer jacket 1610 can include a double layer of material such as a double layer of polyester (PET) with wall thickness ranging between 0.0002 inches and 0.005 inches with a preferred wall thickness range of 0.004 and 0.0015 inches. The double layer is advantageous because it permits a strong pressure seal to be created in a situation where such a seal might not otherwise be possible given the dissimilar nature of the material of the outer jacket 1610 and the sheath tubing 1604, 1606, 1608. The sheath tubing 1604, 1606, 1608 also, preferably includes a malleable metal reinforcement layer embedded therein that can control the shape of the sheath tubing when not being moved by the dilator 304 or pressurization of the region interior to the outer jacket 1610. Pressurization of the collapse pressurization port 1616 can be performed using a syringe, PTCA inflation device, or the like at pressures ranging from about 1 to 30 atmospheres, preferably between about 4 to 12 atmospheres and most preferably at pressures ranging between about 6 to 10 atmospheres, using non-compressible fluids such as saline, water, or radiopaque contrast media.

FIG. 16b illustrates the expandable, re-collapsible iliofemoral introducer 1600 in a second, radially expanded configuration with the inflated dilator still in place. The outer jacket 1610 can be expanded and unfolded with the sheath tubing 1608, 1606 to approximate the maximum profile. The dilator 304 and the dilator balloon 318 remain in place within the sheath. The sheath tubing 1604, 1606, 1608 can retain a generally continuous profile and substantially continuous internal lumen (not shown) of substantially the same size throughout, although some minor distortions of the distal collapsible region 1608 can occur.

FIG. 16c illustrates the iliofemoral introducer 1600 with the dilator 304 (see FIG. 16b) removed and the space 1618 between an outer jacket 1610 and the introducer sheath 1608, 1606 pressurized through the port 1616, on the hub 1602, to collapse the introducer sheath distal tube 1608 to the third, radially collapsed configuration. The gap 1618 between the outer jacket 1610 and the sheath tubing 1608 is visible in this illustration. The transition zone 1606 can taper to the smaller diameter of the collapsed distal, collapsible region 1608. Following completion of this collapsing step by pressurization, the fluid can be withdrawn from the gap 1618 and can thus cause the outer jacket 1610 to become flaccid and at least partially collapse, thus facilitating removal of the now smaller diameter sheath system 1600 from a patient.

FIG. 17a illustrates a collapsing obturator 1700 for use with expandable introducer sheaths. The collapsing obturator 1700 includes a length of obturator tubing 1702, a hub 1722 further including an evacuation port 1712, and a sealing balloon inflation port 1714, a proximal sealing balloon 1708 having a plurality of balloon bonds 1710, a distal sealing balloon 1706 including a plurality of balloon bonds 1710, a plurality of evacuation vents 1704 and an inter-balloon evacuation region 1720.

Referring to FIG. 17a, the sealing balloons 1706 and 1708 can be elastomeric balloons fabricated from materials such as, but not limited to, polyurethane, latex, silicone elastomer, thermoplastic elastomer, or the like, or they can be substantially inelastic balloons such as those fabricated from materials such as, but not limited to, polyolefin, irradiated polyethylene, polyester (PET), polyimide, polyamide, or the like. The proximal and distal sealing balloons 1708, 1706, respectively, can further be coated with conformable materials to improve sealing between the inflated balloons 1708, 1706, and the inside wall of an inflated sheath tube. Such coating (not shown) can include the same materials used to fabricate the elastomeric balloons described herein. The coating can further include hydrogel, or other gel-type substance.

The obturator tubing 1702 can include a multi-lumen cross-section or can include an annular configuration having an inner tube and an outer tube with an annular lumen therebetween to operably transmit pressurized fluid to the interiors of the balloons 1706, 1708 as well as evacuating the inter-balloon region 1720 through the one or more vents 1704. The balloon pressurization port 1714 on the hub 1722 can be operably connected to a lumen and thereby to the interior of the sealing balloons 1706, 1708 by a pressurization vent or skive in the tubing wall 1702 under the region of the balloons 1706, 1708. The evacuation port 1712 can be operably connected to another, separate lumen within the tubing 1702, which can be further operably connected to the one or more vent ports 1704 skived or cut into the tubing 1702 to operably connect the evacuation lumen to the outside environment.

FIG. 17b illustrates the collapsing obturator 1700 having been inserted into a diametrically expanded introducer sheath further including the sheath hub 704, the transition zone tubing 406, and the distal sheath tubing 408, and then pressurized to expand the two sealing balloons 1708, 1706. The proximal sealing balloon 1708 can preferably reside within the proximal non-expandable region of a sheath while the distal sealing balloon 1706 can preferably reside as close as possible to the distal end of the sheath so as to provide some seal but permit the maximum amount of sheath collapse proximal thereto. The inter-balloon evacuation region 1720 can now define a sealed volume with the outer boundary being the inside surface of the expanded sheath distal tubing 408 and transition zone 406.

FIG. 17c illustrates the collapsing obturator 1700 within the introducer sheath with the two sealing balloons 1706, 1708 inflated, and the evacuation region 1720, between the sealing balloons but outside the collapsing obturator 1700, depressurized to radially collapse the distal expandable introducer sheath tubing 408. A partial vacuum can be drawn in the evacuation region 1720, by way of the evacuation port 1712, to collapse the outer sheath tubing 408. Following such deflation, the sealing balloons 1706, 1708 can be deflated and the system can be removed from a patient with less friction and potential for tissue trauma than a sheath that is removed, fully expanded, or never collapsed. Note that a portion of the distal most region of the sheath tubing 408 can remain expanded where the expanded sealing balloon 1706 was located during collapse. This short length of expanded sheath tubing 408 is easier and less traumatic to remove than a longer length of expanded sheath tubing 408. At the proximal end, the sealing balloon 1708 can reside within the transition zone 406 or the non-collapsible sheath tubing near the hub 704, which can be outside the patient and so this has no effect on sheath removal. The distal sealing balloon 1706 can function with a minimum of about 0.100 inches of seal.

FIG. 18a illustrates an expanded view of the expandable, re-collapsible introducer 1600 showing the inflation and deflation lumen within a hub 1602 and outer jacket 1610. The introducer 1600 includes the sheath hub 1602, further including a central lumen 1806, a collapsing port 1616, and a collapsing lumen 1802, a proximal non-expandable region 1604, a distal collapsible region 1608, the outer jacket 1610, a distal jacket to sheath bond 1612, an annular gap 1618, and a collapsing lumen reinforcement 1804. The collapsing lumen reinforcement 1804 can be a tube further including a lumen that can be operably connected to the lumen 1802 within the hub 1602, or it can be a groove, heat welded into the proximal sheath tubing 1604, or the like. The reinforcement 1804 can be non-perforated or it can be perforated with one or more skives, windows, holes, or the like. The outer jacket 1610 can be a single layer or it can include a double layer that can be everted, adhesively adhered, or welded to itself at the distal end. The double layer outer jacket 1610 can have the advantage of providing a very strong bond and, thus improved inflation reliability, as well as the ability to completely collapse the collapsible sheath tubing 1608 substantially all the way to, and including, the distal end of the collapsible sheath distal tubing 1608.

FIG. 18b illustrates a forming obturator 1800 in side view configured to control the shape of the distal collapsible region 1608 of a sheath 1600. The forming obturator 1800 includes a handle 1810, a proximal portion 1812 having a substantially round cross-section, a distal forming region 1814, and a nose cone 1816. The round proximal portion 1812 can be configured to beneficially seal within a hemostasis valve of a sheath hub 1602. The handle 1810 can be configured for manual grasping by the operator. The forming obturator 1800 can preferably be fabricated from flexible materials that can bend within the sheath 1600 but yet retain some shape to help form the sheath distal region 1608 upon re-collapse. The forming obturator 1800 can be a single integral structure or the components can be coupled to one another. The forming obturator 1800 can be fabricated from materials such as, but not limited to, stainless steel, polyethylene, polypropylene, silicone elastomer, thermoplastic elastomer, polyurethane, polyacetal, or the like. The forming obturator 1800, in the forming region 1814 can include various cross-sectional shapes such as, but not limited to, a cross (as illustrated), a three-blade propeller, a U, a W, a V, or the like. The forming obturator 1800 can be configured to be removable and reinserted into a sheath 1600 prior to re-collapse. The forming obturator 1800 can further include a guidewire lumen (not shown) having a diameter of about 0.020 to 0.060 inches. The forming obturator 1800 can also be termed a collapsing obturator. The forming obturator 1800 can help prevent the formation of large, stiff wings in the distal collapsible region 1608 following re-collapse.

FIG. 18*c* illustrates a cross-sectional view of another embodiment of the forming region 1814' of a forming or collapsing obturator 1800 having a three-pronged profile.

FIG. 18*d* illustrates a cross-sectional view of another embodiment of the forming region 1814" of a forming or collapsing obturator 1800 having a splayed U configuration.

Figure 19:
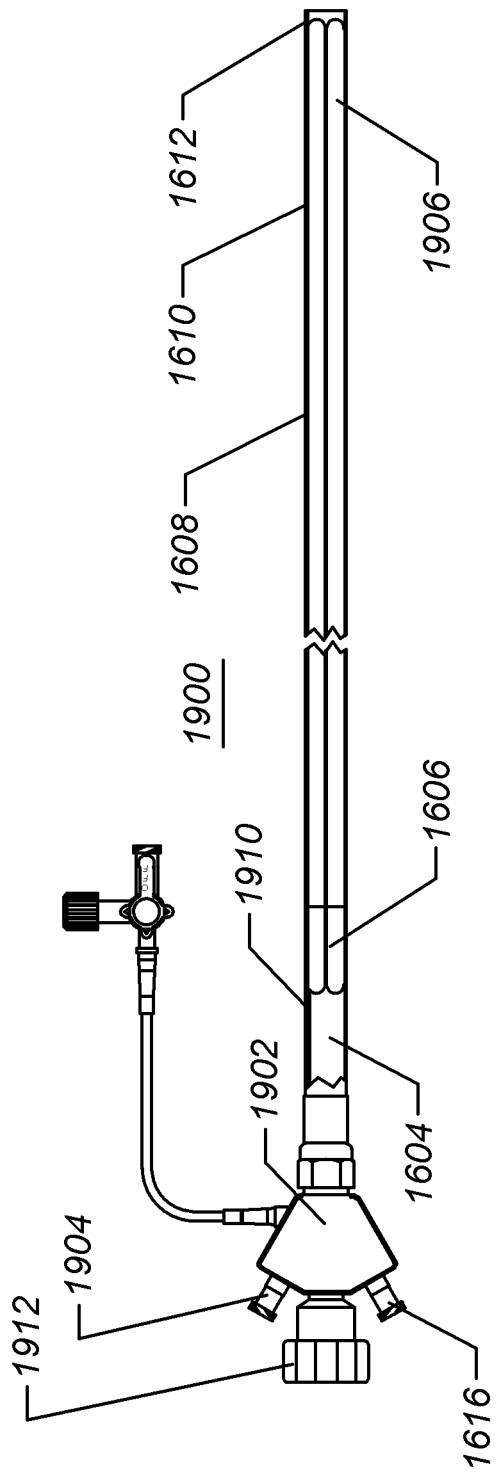
FIG. 19 illustrates an expandable, re-collapsible introducer that includes a non-removable self-expansion element in a radially expanded state, according to an embodiment of the invention

FIG. 19 illustrates an expandable, re-collapsible introducer 1900 that includes a non-removable self-expansion element. The re-collapsible introducer 1900 includes a hub 1902 further including a central port 1912 further including a hemostasis valve, an expansion sideport 1904, a collapse sideport 1616, a length of proximal sheath tubing 1604, a transition zone 1606, a collapsible distal tube 1608, an outer jacket 1610 having a distal weld 1612, and an internal, integral expansion dilator 1906.

Referring to FIG. 19, in which the introducer 1900 is shown in the expanded configuration, the components, except for the integral expansion dilator 1906 can be similar to the device illustrated in FIGS. 18 and 16*a*-16*c*. The integral expansion dilator 1906 can be an annular balloon fabricated from the same materials as those used in other dilators described herein. The integral expansion dilator 1906 can be operably coupled to the expansion sideport 1904 by a lumen (not shown) that can permit pressurized fluid to enter the integral expansion dilator 1906 from the expansion port 1904, when pressurized by an external inflation device, syringe, or the like. When deflated, the integral expansion dilator 1906 includes an annular central lumen capable of permitting catheters and other instrumentation to be inserted therethrough. The integral expansion dilator 1906 can be maintained depressurized and out of the way through the use of a stopcock (not shown) or other valve coupled to the expansion sideport 1904. Collapse of the system can be accomplished by pressurizing the collapse sideport 1616 to pressurize the gap between the outer jacket 1610 and the sheath tube 1608. This collapse can preferably be performed prior to sheath removal from the patient. This device can be repeatedly expanded and collapsed, as needed, as can the devices illustrated in FIGS. 18, 17*a*-17*c*, and 16*a*-16*c*.

Figure 20:
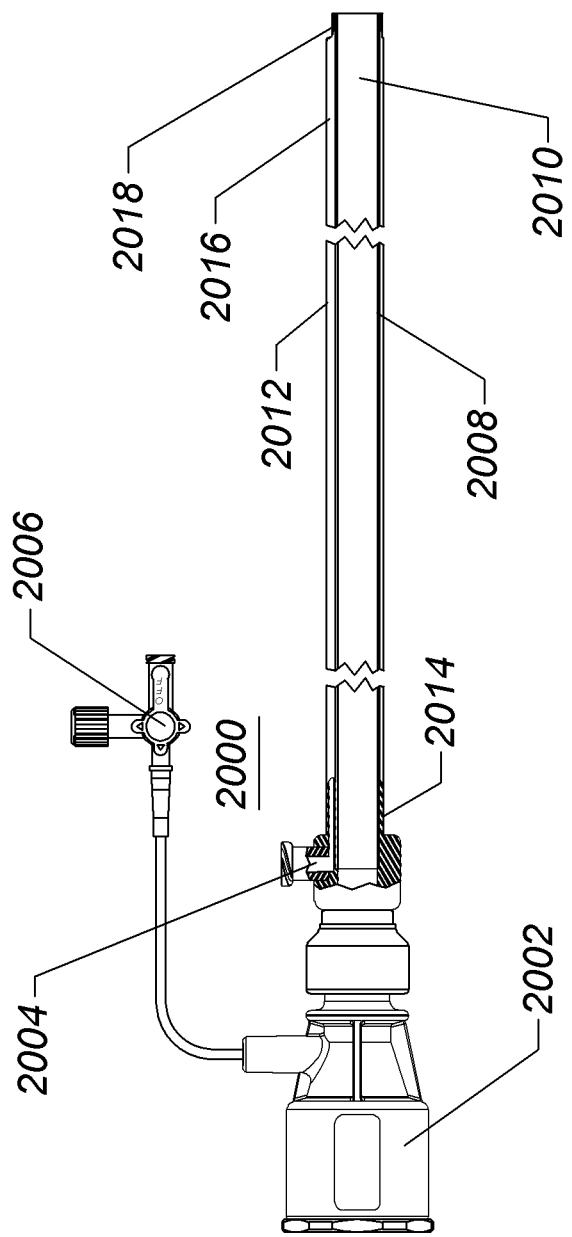
FIG. 20 illustrates a side view, with breakaway in regions distal to the sheath hub, of a re-collapsible introducer that includes an outer pressure jacket welded to the sheath wall at the distal end, according to an embodiment of the invention.

FIG. 20 illustrates a side view, with breakaway in regions distal to the sheath hub 2002, of a re-collapsible introducer 2000 including an outer pressure jacket 2012, a sheath wall 2008, the sheath hub 2002 further including a purge port 2006, a collapse port 2004, a proximal pressure jacket bond 2014, a distal pressure jacket bond 2018, a central sheath lumen 2010, and a pressure chamber 2016.

Referring to FIG. 20, the outer pressure jacket 2012 can be coupled, at the proximal end to the sheath wall 2008 or the sheath hub 2002 by the proximal pressure jacket bond 2014. The distal end of the outer pressure jacket 2012 can be coupled to the sheath wall 2008 by the distal pressure jacket bond 2018. The proximal and distal pressure jacket bonds, 2014 and 2018 respectively, can be heat welds, solvent bonds, adhesive bonds, ultrasonic welds, or the like. The outer pressure jacket 2012 can be fabricated from polyester (PET), or other high strength polymer such as, but not limited to, polyamide, polyimide, or the like. The thickness of the outer pressure jacket 2012 can range from about 0.0001 inches to about 0.002 inches and preferably between about 0.0002 to 0.001 inches. The sheath wall 2008 can be fabricated from polymeric materials such as, but not limited to, polyester, polyimide, polyethylene, polypropylene, Hytrel, Pebax, or the like. The sheath can further include outer and inner layers and reinforcing layers as described elsewhere within this specification. The collapse port 2004 can be operably coupled to the pressure chamber 2016 between the sheath wall 2008 and the pressure jacket 2012 such that fluid can communicate and be introduced or removed from the pressure chamber 2016 by way of the collapse port 2004. In the illustrated embodiment, the pressure chamber 2016 can surround the sheath wall 2008 and can be substantially coaxial thereto although at the proximal end, some distortion of this coaxial alignment may be required to form the proximal pressure jacket bond 2014. The distal pressure jacket bond 2018 in the illustrated embodiment can be coupled to the outside of the sheath tubing 2008 with no folding of the pressure jacket 2012.

Figure 21:
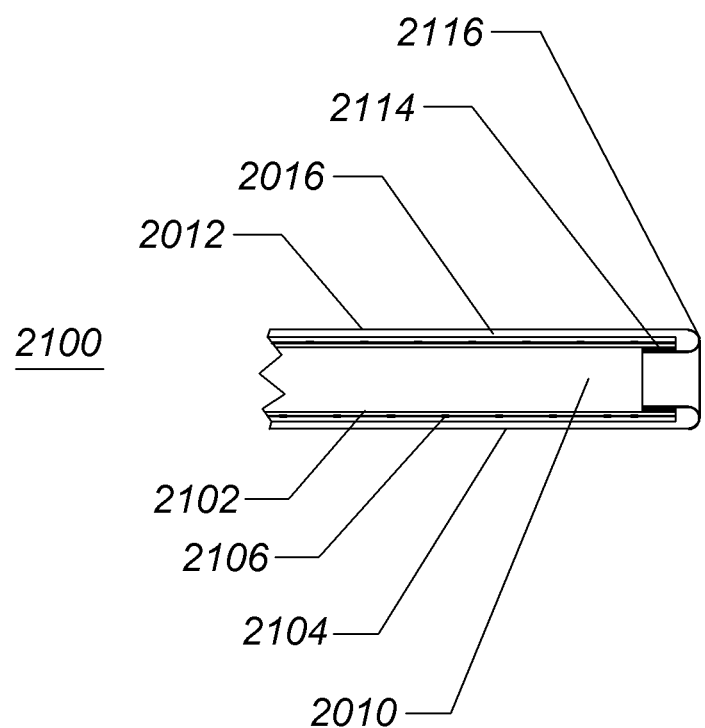
FIG. 21 illustrates a cross-sectional side view of a distal end of a re-collapsible introducer or sheath that includes an outer pressure jacket folded over the distal end of the sheath and welded to the interior of the sheath wall, according to an embodiment of the invention.

FIG. 21 illustrates a cross-sectional side view of the distal end of a re-collapsible introducer or sheath 2100 that includes the outer pressure jacket 2012, the pressure chamber 2016, the sheath central lumen 2010, a sheath inner wall 2102, a sheath outer wall 2104, a sheath reinforcement 2106, a distal pressure jacket bond 2114, and a distal pressure jacket fold 2116.

Referring to FIG. 21, the outer pressure jacket 2012 can be folded, at 2116, over the distal end of the sheath outer wall 2104 and sheath inner wall 2102 and welded or otherwise coupled to the interior of the sheath inner wall 2102. The sheath inner wall 2102 and the sheath outer wall 2104 can be fused or welded together with the sheath reinforcement 2106 embedded therein. In the illustrated embodiment, the sheath inner wall 2102 can be Hytrel 55D, the sheath outer wall can be Hytrel 40D, and the pressure jacket 2102 can be PET, however other polymers or hardnesses can be used to achieve material and bond compatibility. The sheath reinforcement can be a coil of 0.010 wide by 0.003 to 0.005 thick flat, annealed stainless steel wire although other metals, levels of annealing, and dimensions can be useful depending on the design of the sheath. Advantageously, the pressure jacket bond 2114 can allow pressure to be applied to the sheath wall structure 2102, 2104, 2106 all the way to the distal end to force collapse or refolding whereas the embodiment shown in FIG. 20 can include a bond region 2018 that may not be pressurized or collapsed completely. Another advantage of the construction of FIG. 21 is that pressure applied to the pressure chamber 2016 does not easily peel the bond 2114 away from the pressure jacket 2012 or the inner wall 2102.

Figure 22:
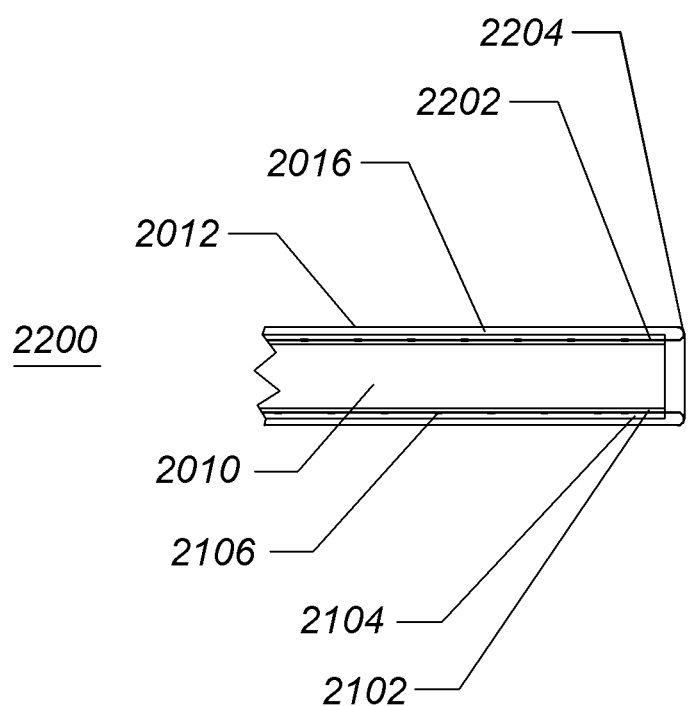
FIG. 22 illustrates a cross-sectional side view of a distal end of a re-collapsible introducer that includes an outer pressure jacket folded over the distal end of the sheath and welded between the inner and outer layers of the sheath wall, according to an embodiment of the invention.

FIG. 22 illustrates a cross-sectional side view of the distal end of a re-collapsible introducer or sheath 2200 that includes the outer pressure jacket 2012, the pressure chamber 2016, the sheath central lumen 2010, the sheath inner wall 2102, the sheath outer wall 2104, the sheath reinforcement 2106, a distal pressure jacket bond 2202, and a distal pressure jacket fold 2204.

Referring to FIG. 22, the outer pressure jacket 2012 can be folded, at 2204, over the distal end of the sheath outer wall 2104 and sheath inner wall 2102 and welded or otherwise coupled between the sheath inner wall 2102 and the sheath outer wall 2104. The sheath inner wall 2102 and the sheath outer wall 2104 can be fused or welded together with the sheath reinforcement 2106 embedded therein. An advantage of this construction of the pressure jacket bond 2202 is that pressure can be applied to the sheath wall structure 2102, 2104, 2106 all the way to the distal end to force collapse or refolding wherein the embodiment shown in FIG. 20 can include a bond region that cannot be pressurized or collapsed completely. Another advantage of the construction of FIG. 22 is that pressure applied to the pressure chamber 2016 does not easily peel the bond 2202 away from the pressure jacket 2012 or the sheath walls 2102 and 2104. The distal pressure jacket bond 2202 can be located distally to the distal extent of the sheath reinforcement 2106 in the illustrated embodiment, although some overlap may be beneficial.

Figure 23:
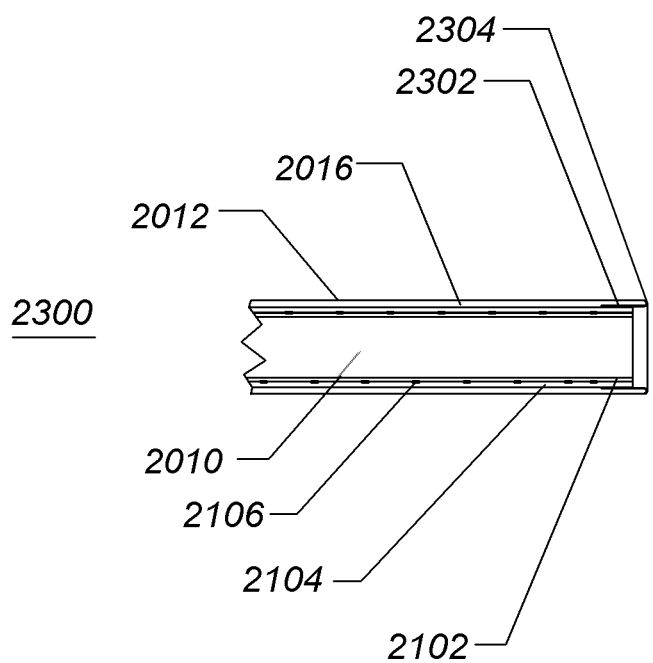
FIG. 23 illustrates a cross-sectional side view of a distal end of a re-collapsible introducer that includes an outer pressure jacket folded over the distal end of the sheath and welded to the exterior of the sheath wall, according to an embodiment of the invention.

FIG. 23 illustrates a cross-sectional side view of the distal end of a re-collapsible introducer or sheath 2300 that includes the outer pressure jacket 2012, the pressure chamber 2016, the sheath central lumen 2010, the sheath inner wall 2102, the sheath outer wall 2104, the sheath reinforcement 2106, a distal pressure jacket bond 2302, and a distal pressure jacket fold 2304.

Referring to FIG. 23, the outer pressure jacket 2012 can be folded, at 2304, distal to the distal end of the sheath outer wall 2104 and sheath inner wall 2102 and welded or otherwise coupled to the sheath outer wall 2104. Advantageously, the pressure jacket bond 2302 can allow pressure to be applied to the sheath wall structure 2102, 2104, 2106 all the way to, and beyond, the distal end to force collapse or refolding, whereas the embodiment shown in FIG. 20 can include the bond region 2018 that may not be pressurized or collapsed completely. Another advantage of the construction of FIG. 23 is that pressure applied to the pressure chamber 2016 does not easily peel the bond 2302 away from the pressure jacket 2012 or the sheath wall 2104. The distal pressure jacket fold 2304 can be created by forming the distal pressure jacket bond 2302 and then everting the pressure jacket 2012 proximally and pulling the pressure jacket over the outer sheath wall 2104. Similar construction techniques can be used in the embodiments shown in FIGS. 21 and 22.

Figure 24:
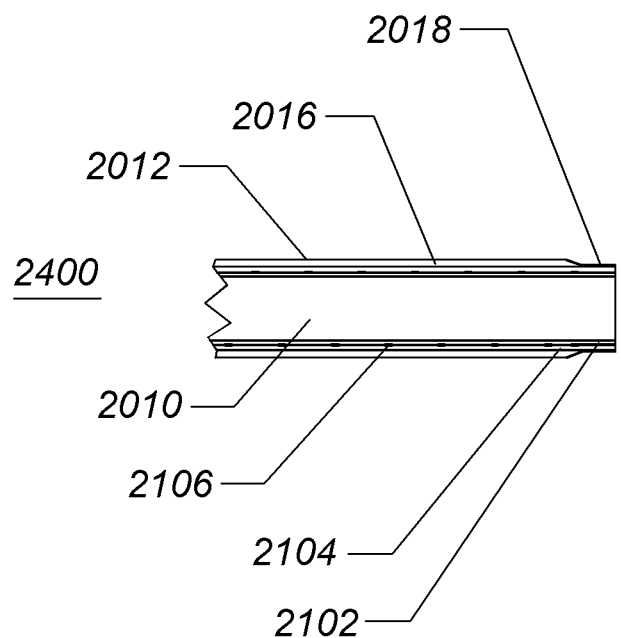
FIG. 24 illustrates a cross-sectional side view of the distal end of the re-collapsible introducer of FIG. 20, detailing how the outer pressure jacket is welded to the exterior of the sheath wall, according to an embodiment of the invention.

FIG. 24 illustrates a cross-sectional side view of the distal end of the re-collapsible introducer of FIG. 20, detailing how the outer pressure jacket 2012 can be welded to the exterior of the sheath wall 2008. The sheath 2000 includes the pressure jacket 2012, the pressure chamber 2016, the sheath central lumen 2010, the sheath inner wall 2102, the sheath outer wall 2104, the sheath reinforcement 2106, and the distal pressure jacket bond 2018.

Referring to FIG. 24, the pressure chamber 2016 does not extend all the way to the distal end of the sheath. This construction can be somewhat simpler than that of FIGS. 21-23 but can result in reduced strength of the distal pressure jacket bond 2018 due to peeling of the pressure jacket from the sheath outer wall 2104 when the pressure chamber 2016 is pressurized with fluid such as, but not limited to, saline, radiopaque contrast media, a combination thereof, or the like. Pressurization beneficial to collapse the sheath wall 2008 can range from about 1 to about 20 atmospheres with a preferred range of about 2 to about 10 atmospheres.

Figure 25A:
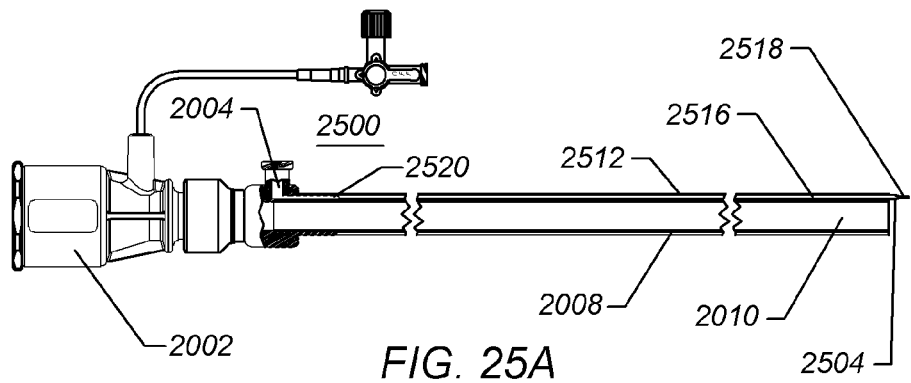
FIG. 25A illustrates a cross-sectional side view of a re-collapsible introducer that includes a side balloon sandwiched between the sheath wall and an outer pressure jacket with the sheath fully expanded, according to an embodiment of the invention.

FIG. 25A illustrates a cross-sectional partial breakaway side view of a re-collapsible introducer 2500, including an uninflated side collapse balloon 2504, further including a distal collapse balloon bond 2518 and a pressure chamber 2516, sandwiched between the sheath wall 2008 and an outer pressure jacket 2512, with the sheath wall 2008 fully expanded. The introducer 2500 also includes the sheath hub 2002, the sheath central lumen 2010, the collapse port 2004, a proximal non-expandable region 2510, and a transition zone 2502.

Referring to FIG. 25A, the sheath central lumen 2010 can be in the fully expanded maximum size configuration suitable for introduction or withdrawal of instrumentation such as catheters, heart valves, stent-grafts, or the like, therethrough. The pressure chamber 2516 can be operably and fluidically connected to the collapse port 2004. The pressure jacket 2512 can be open at the distal end or it can be closed. The pressure jacket 2512 can be coupled to the sheath wall 2008 at the distal end or at locations along the length to facilitate reduction in size when the sheath wall 2008 and the side collapse balloon 2504 is evacuated.

Figure 25B:
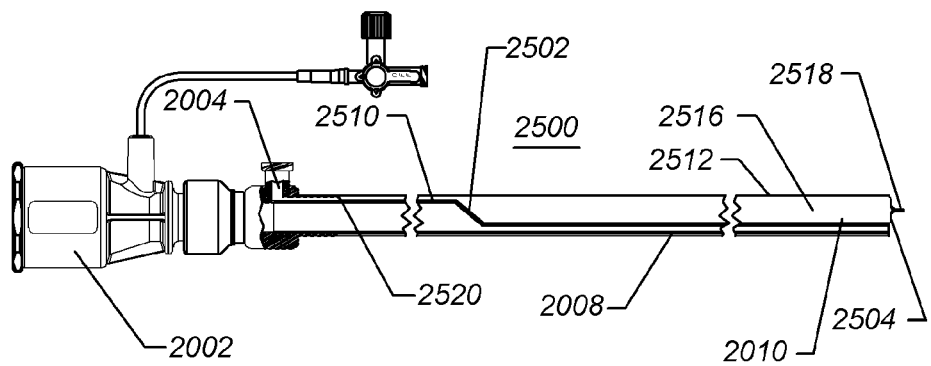
FIG. 25B illustrates a cross-sectional side view of the re-collapsible introducer of FIG. 25A wherein the side balloon has been expanded under pressure, forcing the sheath wall to collapse away from the outer pressure jacket, according to an embodiment of the invention.

FIG. 25B illustrates a cross-sectional partial breakaway side view of the re-collapsible introducer 2500 of FIG. 25A with the side collapse balloon 2504 in the expanded, pressurized state. The introducer 2500 includes the inflated side collapse balloon 2504 further including the distal collapse balloon bond 2518 and the pressure chamber 2516, sandwiched between the sheath wall 2008 and the outer pressure jacket 2512 with the sheath wall 2008 now collapsed in the region distal to the transition zone 2502.

Referring to FIG. 25B, expansion of the side balloon 2504 can force the sheath wall 2008 to fold and compress away from the outer pressure jacket 2512. The proximal non-expandable region 2510 can also be non-collapsible and does not deform upon application of pressure within the pressure chamber 2516. The side balloon 2504 need be disposed only in the region where the sheath 2500 is collapsible, that is, distal to the transition zone 2502. The side balloon 2504 can be operably connected to the collapse port 2004 with a length of tubing or an annulus, or the side balloon 2504 can extend all the way to the proximal side balloon bond 2520. An advantage of this type of collapse mechanism rather than that illustrated in FIG. 20 can be that the sheath wall 2008 is compressed into a "U" shape with a smaller overall cross-sectional profile rather than a more flattened shape.

Figure 25C:
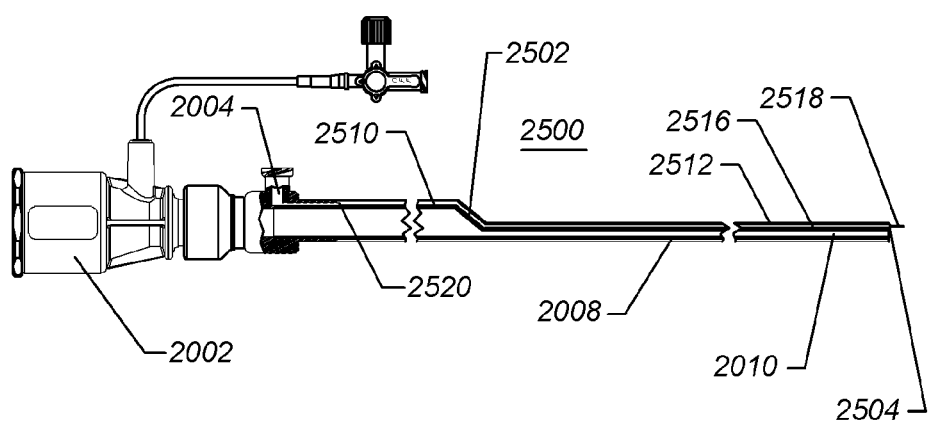
FIG. 25C illustrates a cross-sectional side view of the re-collapsible introducer of FIG. 25B wherein the side balloon has been evacuated thus drawing down the exterior of the side balloon and the pressure jacket to form a low-profile sheath, according to an embodiment of the invention.

FIG. 25C illustrates a cross-sectional side view of the re-collapsible introducer 2500 of FIG. 25B wherein the side balloon 2504 can be evacuated thus drawing down the exterior of the side balloon 2504 and the pressure jacket 2512 toward the collapsed sheath wall 2008 to form a low-profile sheath suitable for removal from a patient's vasculature. The introducer 2500 includes the inflated side collapse balloon 2504 further including the distal collapse balloon bond 2518 and the pressure chamber 2516, sandwiched between the sheath wall 2008 and the outer pressure jacket 2512, with the sheath wall 2008 now collapsed in the region distal to the transition zone 2502.

Figure 26A:
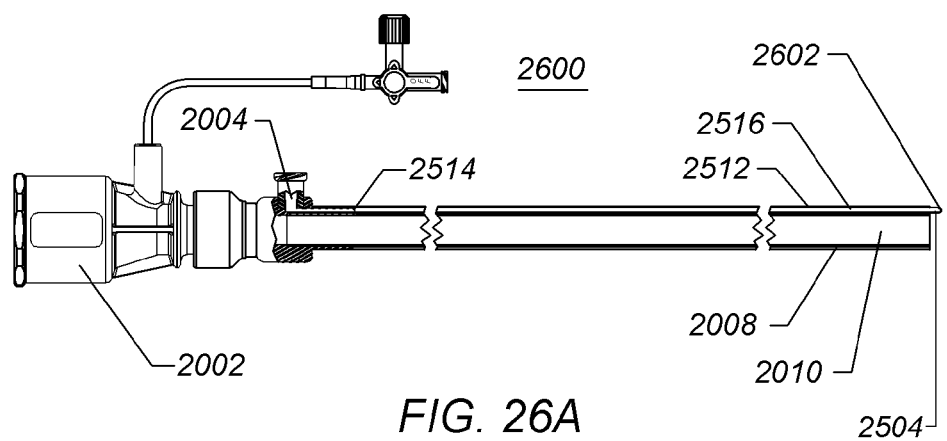
FIG. 26A illustrates a cross-sectional side view of a re-collapsible introducer wherein the side balloon is formed continuously, without a weld or bond at a distal end, according to an embodiment of the invention.

FIG. 26A illustrates a cross-sectional side view of a re-collapsible introducer 2600 wherein the side collapse balloon 2504 can be formed continuously, without a weld or bond at the distal end. The introducer 2600 includes the sheath hub and the uninflated side collapse balloon 2504. The side collapse balloon 2504 further includes a distal collapse balloon closed end 2602 and a pressure chamber 2516, which can be sandwiched between the sheath wall 2008 and the outer pressure jacket 2512, with the sheath wall 2008 fully expanded. The introducer 2600 also includes the sheath hub 2002, the sheath central lumen 2010, and the collapse port 2004.

Referring to FIG. 26A, the illustrated embodiment can be similar to that shown in FIGS. 25A through 25C, however, the side collapse balloon 2504 can have the closed distal end 2602 rather than a weld or bond at the distal end. The side collapse balloon 2504 can extend substantially even with or beyond the distal end of the sheath tubing wall 2008. This type of closed distal end 2602 can be fabricated using stretch blow molding to expand a billet, or pre-form, that can be closed at the distal end.

Figure 26B:
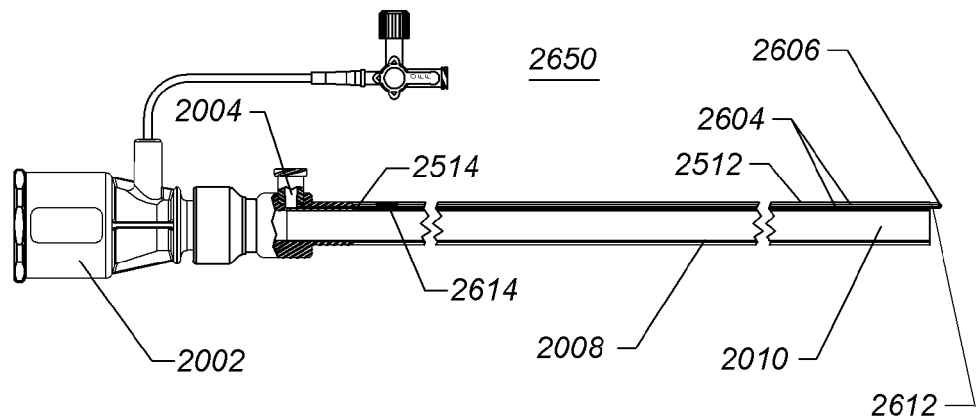
FIG. 26B illustrates a cross-sectional side view of a re-collapsible introducer wherein the side balloon has been folded over at the distal end of the sheath to form a double balloon stacked radially away from the axis of the sheath, according to an embodiment of the invention.

FIG. 26B illustrates a cross-sectional side view of a re-collapsible introducer 2650 wherein the side collapse balloon 2612 can be twice as long as the expandable part of the sheath wall 2008 and can include a fold 2606 at the distal end of the sheath to form a double balloon 2612 stacked radially away from the axis of the sheath. The double balloon 2612 can be coupled at the proximal end to the sheath tubing 2008 or the sheath hub 2002. One of the two proximal ends of the double balloon 2612 can be closed with seal 2614 to prevent fluid escape and the other proximal end seal 2514 can be coupled and operably connected to the collapse port 2004 by adhesive welding, heat welding, ultrasonic welding, or the like. Fluid injected or withdrawn through the collapse port 2004 can enter or leave the double pressure chamber 2604. The pressure jacket can surround the sheath wall 2008 and the double balloon 2612 and can be coupled to any structures that are convenient using adhesives, mechanical fixation, or the like. Expansion of the double balloon can compress the sheath wall 2008 and can beneficially provide more precise shape control of the collapsed sheath wall 2008 as well as eliminate the seal at the distal end of the collapse side balloon 2504 of FIGS. 25A-C.

FIG. 27A illustrates a cross-sectional end view of the distal, collapsible end of the sheath 2000, as illustrated in FIG. 20, that is fully expanded. The sheath includes the sheath wall 2008, the outer pressure jacket 2012, the pressure chamber 2016, the malleable reinforcement 2106, and the sheath central lumen 2010.

FIG. 27B illustrates a cross-sectional end view of the distal, collapsible end of the sheath 2000 of FIG. 27A, wherein the pressure chamber or region 2016 between the outer pressure jacket 2012 and the sheath wall 2008 has been pressurized to collapse the sheath wall 2008 and the malleable reinforcement 2106. The shape of the cross-section can be a flattened, curved structure that can be larger in a lateral dimension than the expanded sheath of FIG. 27A but can have lower overall contact with a blood vessel (not shown). The central sheath lumen 2010 can be distorted and collapsed.

FIG. 27C illustrates a cross-sectional end view of the distal, collapsible end of the sheath of FIG. 27A and 27B wherein the pressure chamber, or region 2016, between the outer pressure jacket 2012 and the sheath wall 2008 has been evacuated to collapse the outer pressure jacket 2012 and resultant sheath exterior.

Figure 28A:
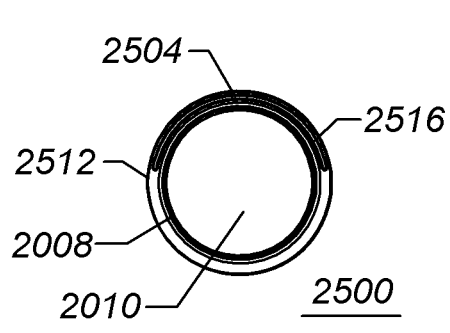
FIG. 28A illustrates a cross-sectional end view of a distal, collapsible end of a fully expanded sheath that includes a sheath wall, a side-balloon, and an outer pressure jacket, according to an embodiment of the invention.

FIG. 28A illustrates a cross-sectional end view of the distal, collapsible end of a fully expanded sheath 2500 that can include the sheath wall 2008, the side-balloon 2504 further including the pressure chamber 2516, the central lumen 2010, and the outer pressure jacket 2512. The sheath wall 2008 can be fully expanded revealing a maximum sized sheath central lumen 2010. The side balloon 2504, sandwiched between the pressure jacket 2512 and the sheath wall 2008 on one side, can be collapsed and can include a minimized pressure chamber 2516. In some embodiments, one side balloon 2504 can be used. In some embodiments, up to four side balloons 2504 or more can be used.

Figure 28B:
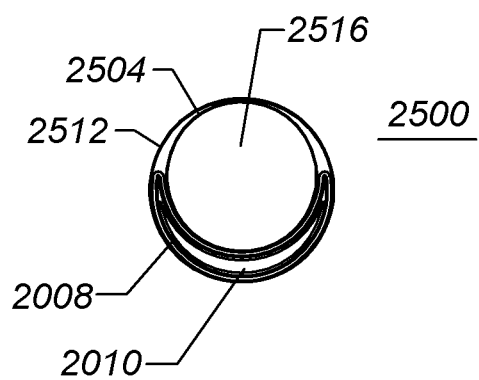
FIG. 28B illustrates a cross-sectional end view of the distal, collapsible end of the sheath of FIG. 28A, wherein the side-balloon has been pressurized and expanded to collapse the sheath wall, according to an embodiment of the invention.

FIG. 28B illustrates a cross-sectional end view of the distal, collapsible end of the sheath 2500 of FIG. 28A, wherein the pressure chamber 2516 of the side-balloon 2504 is pressurized and expanded to collapse the sheath wall 2008 away from the pressure jacket 2512, and into an arcuate or "U" shape with a smaller cross-sectional area than illustrated in FIG. 28A.

Figure 28C:
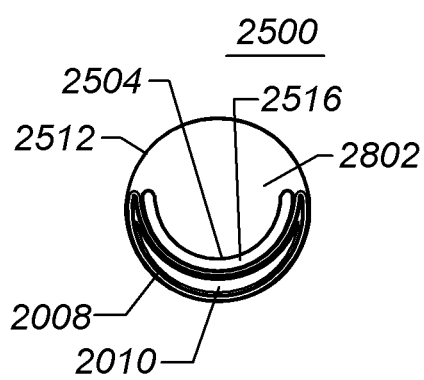
FIG. 28C illustrates a cross-sectional end view of the distal, collapsible end of the sheath of FIGS. 28A and 28B, wherein the side-balloon has been evacuated and collapsed, according to an embodiment of the invention.

FIG. 28C illustrates a cross-sectional end view of the distal, collapsible end of the sheath 2500 of FIGS. 28A and 28B, wherein the pressure chamber 2516 within the side-balloon 2504 has been evacuated and collapsed against the sheath wall 2008. The pressure jacket 2512 can remain large and the region 2802 between the pressure jacket 2512 and the sheath wall 2008 can remain large. In some embodiments, adhesives, welds, fasteners, or the like can be used to maintain the pressure jacket 2512 adjacent to the sheath wall 2008.

Figure 28D:
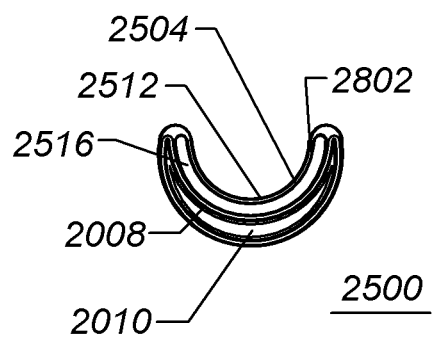
FIG. 28D illustrates a cross-sectional end view of the distal, collapsible end of the sheath of FIG. 28C, wherein the region between the side-balloon and the pressure jacket has been evacuated causing the pressure jacket to collapse, according to an embodiment of the invention.

FIG. 28D illustrates a cross-sectional end view of the distal, collapsible end of the sheath 2500 of FIG. 28C, wherein the region 2802 between the side-balloon 2504 and the pressure jacket 2512 has been evacuated, causing the pressure jacket 2512 to collapse against the side balloon 2504, thus minimizing the profile of the system.

Figure 29:
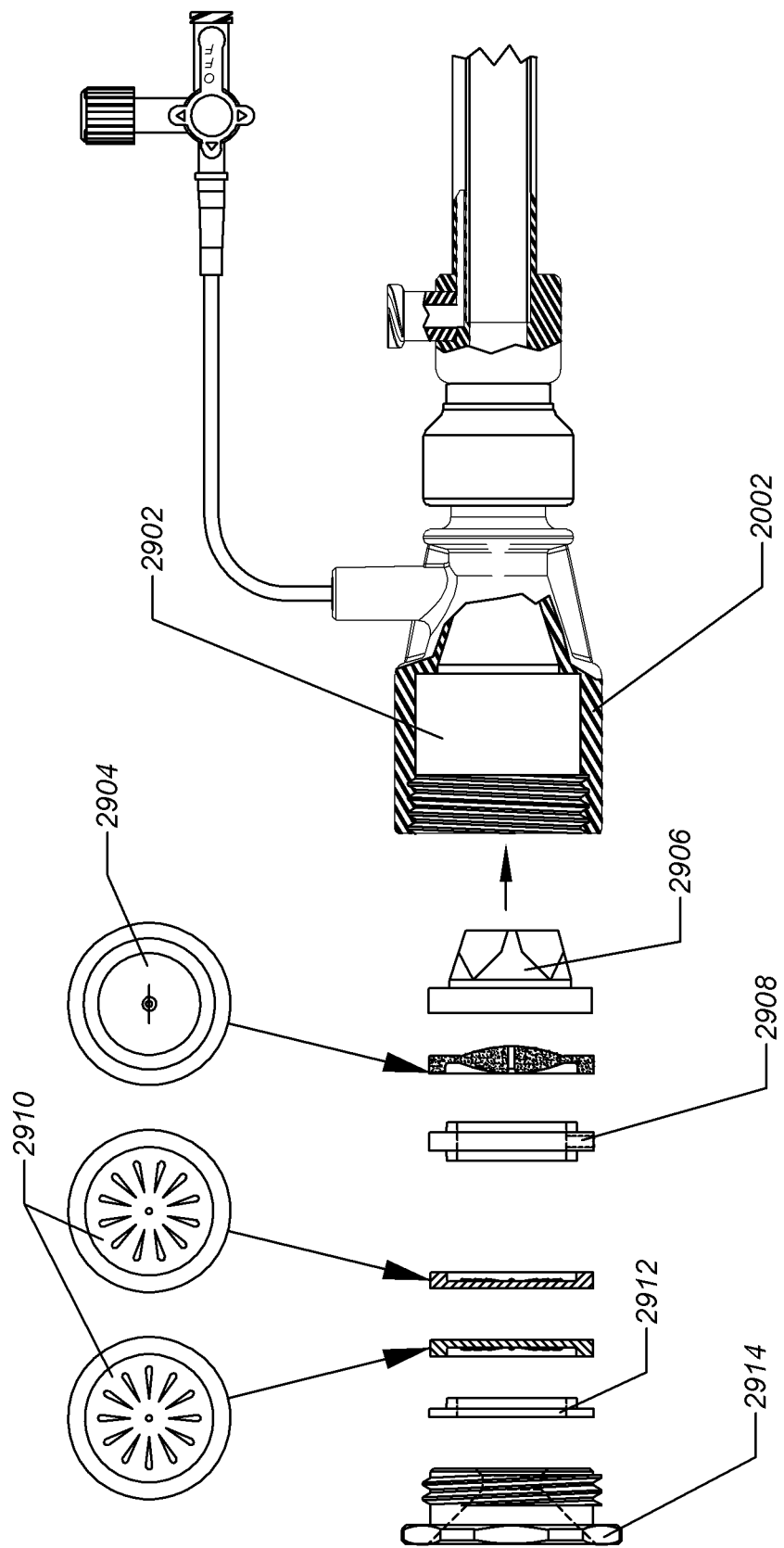
FIG. 29 illustrates a cross-sectional exploded side view of a sheath hub and the internal components that provide for hemostasis during and following introduction of catheters or instruments therethrough, according to an embodiment of the invention.

FIG. 29 illustrates a partial breakaway side view of a sheath hub 2002 and the internal components that can provide for hemostasis during and following introduction of catheters or instruments therethrough. The sheath hub 2002 can include a hub cavity 2902, a hub cap 2914, a thin spacer 2912, a plurality of pinhole valves 2910, a wide spacer 2908, a pinhole slit disc 2904, and a cross-slit valve 2906.

Referring to FIG. 29, the sheath hub 2002 can be fabricated from substantially rigid materials such as, but not limited to, polycarbonate, polysulfone, ABS, or the like. The pinhole valves 2910, the cross slit valve 2906, and the pinhole slit disc 2904 can be fabricated from elastomeric polymers such as, but not limited to, silicone elastomer, latex, polyester elastomers, nylon elastomers, polyurethane elastomers, or the like. Hardness ranges for the elastomers can range between about 10 A and 65 A, with a preferred range of about 30 A and 50 A. In some embodiments, the pinhole valves 2901 can be separated from the pinhole slit valve 2904 by the wide spacer 2908. The thin spacer 2912 can serve as a washer to prevent distortion of the elastomeric pinhole valves 2910, when the hub cap 2914 can be threaded into place at the proximal end of the sheath hub 2002.

The cross-slit valve 2906 can serve to close off the system from blood leakage at systemic arterial pressures when nothing is inserted through the system. The pinhole slit valve or disc 2904 can close against and provide hemostasis for a guidewire having a diameter of about 0.010 to about 0.040 inches diameter following removal of large catheters (up to 26 French or larger). The pinhole valves 2910 can seal against blood leakage prior to a catheter having been introduced through the system. The pinhole valves 2910 can include a central hole having a diameter of about 0.010 to about 0.030 inches with a preferred range of about 0.018 to 0.025 inches diameter. The pinhole valves 2910 can also serve to center a guidewire (not shown) so that it remains properly aligned within the hole at the center of the pinhole slit disc 2904. The slit in the pinhole slit valve 2904 can have no width, but can have a length ranging from about 2 mm to about 15 mm.

The internal components of the sheath hub 2002 can be assembled with substantially no longitudinal distance between each part to maximize stability and controllability of the valve seal. The pinhole slit valve 2904, in the illustrated embodiment can include a double convex center with the center thickness dimension greater than the thickness dimension at a more radially outward location, excluding the mounting flange on the extreme exterior of the pinhole slit valve 2904. The central hole, having a diameter of about 0.020 to 0.035 inches, can beneficially include a fillet or chamfer on the proximal side to facilitate inserting guidewires and catheters therethrough. In some embodiments, it may be beneficial to fabricate the pinhole valves 2910 from different hardness materials. For example, the more distal pinhole vale 2910 can have a hardness of 50 A while the proximal pinhole valve 2910 can have a hardness of 35 A. This latter embodiment can provide for improved seal following long-term placement of a dilator through the valve relative to a system using only 35 A pinhole valves 2910.

The hub cap 2914 can include a central orifice that can taper inward as the cap 2914 extends distally to help guide catheters inserted therethrough toward the center. The central hole can further provide limitation to prevent too large a catheter from being inserted therethrough.

Figure 30:
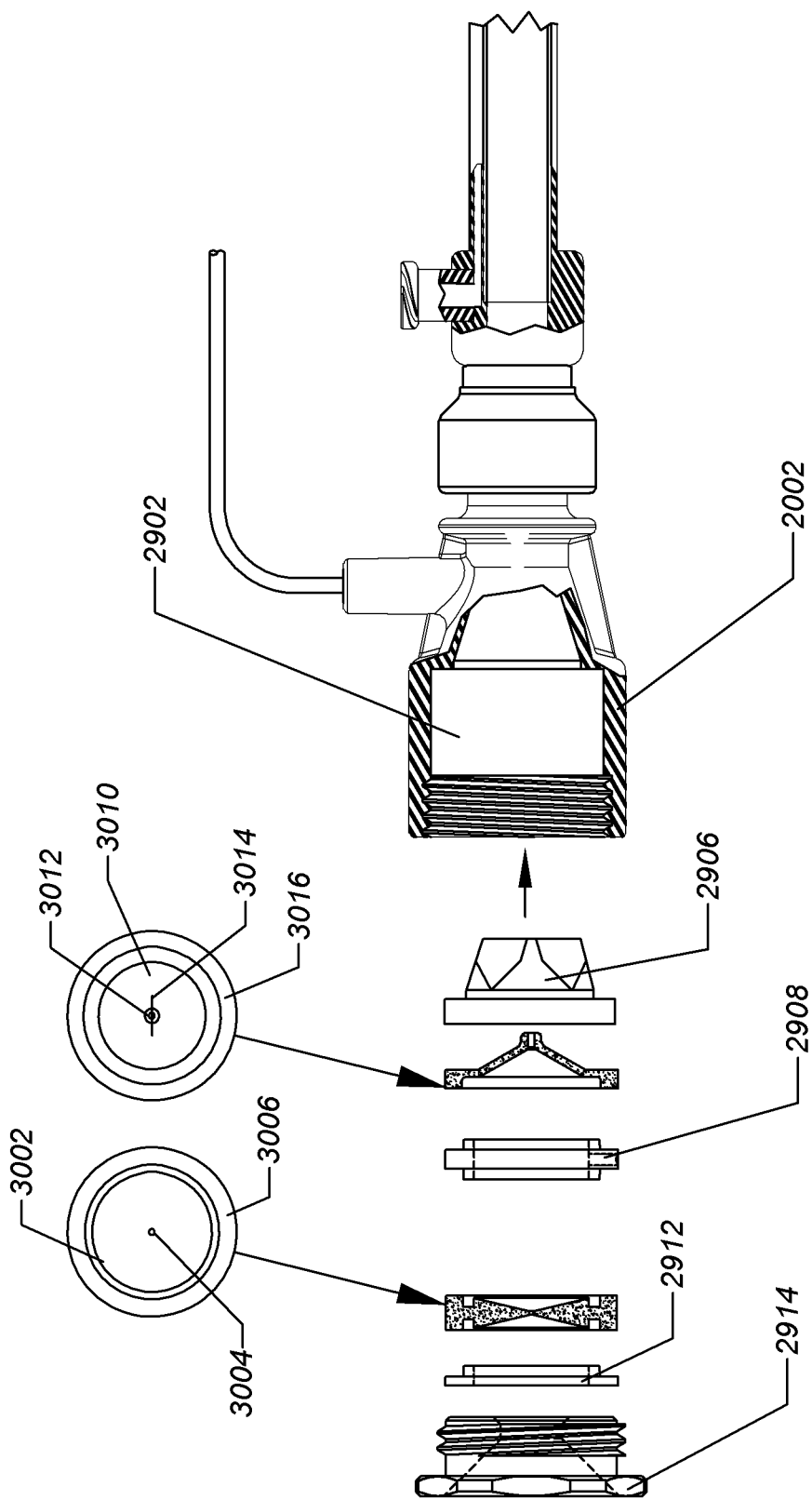
FIG. 30 illustrates cross-sectional exploded side views of alternative embodiments of the components within the sheath hub, according to an embodiment of the invention.

FIG. 30 illustrates cross-sectional side views of alternative embodiments of the components within the sheath hub 2002. The sheath hub 2002 can include the hub cavity 2902, which can be an axially elongate inner void defined by the walls of the sheath hub 202. FIG. 30 differs from FIG. 29 in that the pinhole valves 2910 and the pinhole slit valve 2904 can be replaced with alternate valve mechanisms. The 2910 pinhole valves, of which there can be two, can be replaced by a single double convex elastomeric valve 3002. The double convex elastomeric valve can include the central orifice 3004 and the outside flange 3006. The pinhole slit valve 2904 can be replaced by a conical taper valve 3010 further including a central orifice 3012, a slit 3014, and an exterior flange 3016. Both valves 3002 and 3010 can be fabricated from the same materials as used in fabricating the elastomeric valves of FIG. 29. The double convex elastomeric valve orifice 3004 can have a diameter of about 0.010 to 0.035 inches. The conical valve 3010 includes a similar diameter central hole 3012 as that of the double convex valve 3002. These valves can feature tapers to guide catheters therethrough and substantial material masses to control the size of the central orifices. The components 3002 and 3010 can be sandwiched tightly within the valve body 2002 with little or no axial spacing therebetweeen. The use of the double convex valve 3002 or the conical pinhole slit valve 3010 can be interchanged or mixed to maximize sheath hub function.

It should be noted that certain objects and advantages of the invention have been described above for the purpose of describing the invention and the advantages achieved over the prior art. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

Moreover, although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. For example, it can be contemplated that various combination or subcombinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the claims that follow.

What is claimed is:

1. An intra-aortic catheter, comprising:
    a first elongate member comprising a proximal portion, a collapsible distal portion, and a lumen extending through the proximal portion and the collapsible distal portion;
    a second elongate member comprising a proximal end, a distal end, and a lumen between the proximal end and the distal end, the lumen of the second elongate member comprising a chamber, the collapsible distal portion of the first elongate member positioned within the lumen of the second elongate member; and
    a dilator positioned within the lumen of the first elongate member, the dilator configured to expand the collapsible distal portion of the first elongate member from a first, collapsed cross-sectional configuration to a second, expanded cross-sectional configuration;
    wherein the chamber of the second elongate member is configured to, when pressurized, collapse the collapsible distal portion of the first elongate member from the second, expanded cross-sectional configuration to a third, collapsed cross-sectional configuration, the collapsible distal portion of the first elongate member having an outer diameter smaller in the third, collapsed cross-sectional configuration than in the second, expanded cross-sectional configuration.

2. The catheter of claim 1, wherein at least a portion of the collapsible distal portion of the first elongate member is positioned adjacent to the chamber of the second elongate member.

3. The catheter of claim 1, wherein at least a portion of the collapsible distal portion of the first elongate member is positioned within the chamber of the second elongate member.

4. The catheter of claim 3, wherein the distal end of the second elongate member is bonded to the collapsible distal portion of the first elongate member.

5. The catheter of claim 4, wherein the distal end of the second elongate member is folded over a distal end of the first elongate member and coupled to an inner surface of the first elongate member.

6. The catheter of claim 4, wherein the distal end of the second elongate member is folded over a distal end of the first elongate member and coupled between an inner surface and outer surface of the first elongate member.

7. The catheter of claim 4, wherein the proximal end of the second elongate member is bonded to the proximal portion of the first elongate member.

8. The catheter of claim 1, wherein the collapsible distal portion comprises one or more longitudinal folds when in the first, collapsed cross-sectional configuration.

9. The catheter of claim 8, wherein the one or more longitudinal folds comprise two outside edges and two inside edges which form longitudinal creases.

10. The catheter of claim 1, wherein the first elongate member further comprises a malleable reinforcement embedded in at least a portion of the collapsible distal portion.

11. The catheter of claim 10, wherein the malleable reinforcement is configured to:
    reform in response to expansion of the dilator;
    reform in response to pressurization of the chamber of the second elongate member; and
    maintain the collapsible distal portion in each of the first, collapsed cross-sectional configuration, the second, enlarged cross-sectional configuration, and the third, collapsed cross-sectional configuration.

12. The catheter of claim 11, wherein the malleable reinforcement is a metal coil.

13. The catheter of claim 1, wherein the first, collapsed cross-sectional configuration and the third, collapsed cross-sectional configuration have a substantially similar diameter.

14. The catheter of claim 1, wherein the dilator comprises a balloon dilator.

15. The catheter of claim 1, wherein the first elongate member further comprises a sheath hub at a proximal end of the first elongate member, the sheath hub comprising a port operably connected to the chamber of the second elongate member.

16. The catheter of claim 15, wherein the dilator comprises a dilator hub at a proximal end of the dilator, the dilator hub releasably coupled to the sheath hub.

17. The catheter of claim 1, wherein the dilator comprises a distal fairing configured to cover a distal edge of the first elongate member.

18. An intra-aortic catheter, comprising:
a first elongate member comprising a lumen;
a second elongate member comprising one or more vents and a distal balloon positioned distal to the one or more vents; and
a hub comprising a first port and a second port;
wherein the second elongate member is configured to be positioned within the lumen of the first elongate member;
wherein the distal balloon is configured, when expanded, to form a seal with an inside surface of the first elongate member such that a gap is created in the lumen of the first elongate member between an inner surface of the first elongate member and an outer surface of the second elongate member, the gap positioned proximal to the distal balloon; and
wherein the first port is operably connected to the one or more vents to evacuate the gap to deflate the first elongate member, and the second port is operably connected to the distal balloon to allow the distal balloon to remain substantially expanded when the gap is being evacuated.

19. The catheter of claim 18, wherein the second elongate member further comprises a proximal balloon positioned proximal to the one or more vents, wherein the proximal balloon is configured, when expanded, to form a seal with an inside surface of the first elongate member proximal to the gap.

* * * * *